US008226960B2

(12) United States Patent
Masignani et al.

(10) Patent No.: US 8,226,960 B2
(45) Date of Patent: Jul. 24, 2012

(54) CHIMERIC, HYBRID AND TANDEM POLYPEPTIDES OF MENINGOCOCCAL NMB1870

(75) Inventors: Vega Masignani, Siena (IT); Maria Scarselli, Siena (IT); Rino Rappuoli, Siena (IT); Mariagrazia Pizza, Siena (IT); Marzia Monica Giuliani, Siena (IT)

(73) Assignee: Novartis AG, Basel (CH)

( * ) Notice: Subject to any disclaimer, the term of this patent is extended or adjusted under 35 U.S.C. 154(b) by 849 days.

(21) Appl. No.: 12/085,413

(22) PCT Filed: Nov. 27, 2006

(86) PCT No.: PCT/IB2006/003876

§ 371 (c)(1),
(2), (4) Date: Jan. 26, 2009

(87) PCT Pub. No.: WO2007/060548

PCT Pub. Date: May 31, 2007

(65) Prior Publication Data

US 2011/0166323 A1 Jul. 7, 2011

(30) Foreign Application Priority Data

Nov. 25, 2005 (GB) .................................. 0524066.8

(51) Int. Cl.

| | |
|---|---|
| ***A61K 39/095*** | (2006.01) |
| ***C07H 21/04*** | (2006.01) |
| ***C12P 21/04*** | (2006.01) |
| ***C07K 14/00*** | (2006.01) |

(52) U.S. Cl. ............... 424/250.1; 424/234.1; 424/184.1; 530/350; 435/69.1; 435/69.5; 435/69.7; 536/23.5; 536/23.7

(58) Field of Classification Search ........................ None
See application file for complete search history.

(56) References Cited

U.S. PATENT DOCUMENTS 7,785,608 B2 * 8/2010 Zlotnick et al. ............ 424/249.1

FOREIGN PATENT DOCUMENTS

| | | |
|---|---|---|
| WO | WO 03/020756 | 3/2003 |
| WO | WO 03/063766 | 8/2003 |
| WO | WO 2004/048404 | 6/2004 |
| WO | WO 2006/024954 | 3/2006 |

OTHER PUBLICATIONS

Gomez et al. Vaccine 14: 1340-1346, 1996.*
Malorny et al. J. Bacteriol. 180: 1323-1330, 1998.*
Teerlink et al. J. Exp. Med. 166: 63-76, 1987.*
Forest et al. Gene 192: 165-169, 1997.*
Ala'Aldeen et al. Vaccine 12:535-541, 1994.*
Masignani et al , 2003 ; J. Exp. Med. 197(6):789-799.*

* cited by examiner

*Primary Examiner* — Padma Baskar
(74) *Attorney, Agent, or Firm* — Amy Hessler; Otis Littlefield

(57) ABSTRACT

NMB1870 is a protein in *Neisseria meningitidis*. Three families of NMB1870 are known. To increase the ability of a NMB1870 protein to elicit antibodies that are cross-reactive between the families, NMB1870 is engineered. Sequences can be substituted from one NMB1870 family into the corresponding position in another family. Proteins of NMB1870 sequences from different families can be joined to each other.

4 Claims, No Drawings

CHIMERIC, HYBRID AND TANDEM POLYPEPTIDES OF MENINGOCOCCAL NMB1870

RELATED APPLICATIONS

This application is the U.S. National Phase of International Application No. PCT/IB2006/003876, filed Nov. 27, 2006 and published in English, which claims priority to Great Britain Application No. 0524066.8 filed Nov. 25, 2005. The teachings of the above applications are incorporated in their entirety by reference.

TECHNICAL FIELD

This invention is in the field of immunisation and, in particular, immunisation against diseases caused by pathogenic bacteria in the genus *Neisseria*, such as *N. meningitidis* (meningococcus).

INCORPORATION BY REFERENCE OF MATERIAL ON COMPACT DISC

This application incorporates by reference the Substitute Sequence Listing contained on the two compact discs (Copy 1 and Copy 2), filed concurrently herewith, containing the following tile:

File name: USSN12_085413seq_listing2.txt; created Oct. 14, 2009; 165 KB in size.

BACKGROUND ART

*Neisseria meningitidis* is a Gram-negative encapsulated bacterium which colonises the upper respiratory tract of approximately 10% of human population. Although polysaccharide and conjugate vaccines are available against serogroups A, C, W135 and Y, this approach cannot be applied to serogroup B because the capsular polysaccharide is a polymer of polysialic acid, which is a self antigen in humans. To develop a vaccine against serogroup B, surface-exposed proteins contained in outer membrane vesicles (OMVs) have been used. These vaccines elicit serum bactericidal antibody responses and protect against disease, but they fail to induce cross-strain protection [1]. Some workers are therefore focusing on specific meningococcal antigens for use in vaccines [2].

One such antigen is 'NMB1870'. This protein was originally disclosed as protein '741' from strain MC58 [SEQ IDs 2535 & 2536 in ref. 3; SEQ ID 1 herein], and has also been referred to as 'GNA1870' [refs. 4-6, following ref. 2] and as 'ORF2086' [7-9]. This lipoprotein is expressed across all meningococcal serogroups and has been found in multiple meningococcal strains. NMB1870 sequences have been grouped into three families (referred to herein as families I, II & III), and it has been found that serum raised against a given family is bactericidal within the same family, but is not active against strains which express one of the other two families i.e. there is intra-family cross-protection, but not inter-family cross-protection.

To achieve cross-strain protection using NMB1870, therefore, more than one family is used. To avoid the need to express and purify separate proteins, it has been proposed to express different families as hybrid proteins [10-12], including two or three of the families in a single polypeptide chain. Several hybrids have been tested and give encouraging anti-meningococcal efficacy.

It is an object of the invention to provide further and improved approaches for overcoming the family specificity of protection afforded by NMB1870, and to use these approaches for providing immunity against meningococcal disease and/or infection, particularly for serogroup B.

DISCLOSURE OF THE INVENTION

Complementing the work described in reference 13, the inventors have substituted sequences from one NMB1870 family into the corresponding position in another family, with the aim of producing a chimeric NMB1870 that does not have the family specificity of the wild-type polypeptides.

As an alternative to engineering a single NMB1870 such that it has features of all three families, the inventors have also produced new hybrid and tandem polypeptides that include NMB1870 sequences from multiple families, thereby complementing the work described in references 10 and 12.

Whereas each individual NMB1870 family can elicit antibodies (e.g. in mice) that are effective only against strains in the same NMB1870 family, the chimeric, hybrid and tandem polypeptides of the invention can elicit antibodies that recognise NMB1870 polypeptides from more than one family.

The inventors have also identified various new polymorphic forms of NMB1870, including sequences distinct from the three previously-reported families (family IV).

NMB1870 Family Substitutions

Reference 13 discloses the substitution of sequences from one NMB1870 family into another NMB1870 framework, to give chimeric NMB1870 polypeptides. The inventors have performed further work on chimeras and have identified a number of key residues for substitution in the family I NMB1870 sequence. Substitution of these residues can improve the ability of the polypeptide to elicit antibodies that cross-react with family II polypeptides.

Thus the invention provides a polypeptide comprising an amino acid sequence that has at least 70% identity to SEQ ID NO:57, and wherein one or more of the following residues is either substituted with another amino acid or is deleted: F14; T16; Q18; Q20; D21; S22; E23; H24; S25; G26; K27; K31; Q33; R35; 136; G37; 139; K48; E51; G52; R54; T56; A67; G68; K70; T72; A78;A79; N83; K85; D97; D102; P105; G107; R109; S114; S116; L118; N120; Q121; A122; K135; T147; V148; N149; G150; I151; R152; H153.

It is preferred that at least one of the following residues is substituted: F14; T16; Q18; K31; Q33; R35; 136; G37; I39; T56; K70; T72; A78; A79; K85; D97; D102; S114; S116; L118; K135. None of these residues was selected for substitution in reference 13.

Preferred amino acids for substitution or deletion are: F14; T16; Q18; Q20; D21; S22; E23; H24; S25; G26; K27; K31; Q33; R35; 136; G37; K48; E51; G52; R54; T72; A79; K85; P105; G107; R109; L118; N120; Q121; A122; T147; V148; N149; G150; S151; R152; H153.Substitution of residues is preferred, except for E51, where deletion is preferred.

Residues are preferably substituted with the corresponding amino acid from NMB1870 in family II or family III. Preferred substitutions are thus: FI4L; T161; Q18K; Q2ON; D21N; S22P; E23D; H24K; S25I; S25T; G26D; K27S; K31Q; Q33S; R35L; I36V; G37S; I39L; K48Q; G52D; R54K; T56E; A67P; G68N; K70R; T72H; A78T; A79K; N83H; N83Y; K85R; D97E; D102E; P105A; G107E; R109S; S114L; S116D; L118R; N120G; Q121S; A122E; K135R; T147I; V148G; N149E; G150K; I151V; R152H; H153E. Only residues 25 and 83 in this list have more than one preferred substitution, as all of the others have the same amino acid in two of families I, II and III.

The amino acid sequence has at least 70% identity to SEQ ID NO:57, e.g. ≧75%, ≧80%, ≧85%, ≧90%, ≧95%, ≧96%, ≧97%, ≧98%, ≧99% or more. This sequence may be present as part of a larger polypeptide.

The polypeptide can have the ability to induce bactericidal anti-meningococcal antibodies after administration to a host animal, and in preferred embodiments can induce antibodies that are bactericidal against strains in each of the three NMB1870 families I to III. Further information on bactericidal responses is given below.

One preferred amino acid sequence is SEQ ID NO:58 which, compared to SEQ ID NO:57, has substitutions at: F14; T16; Q18; Q20; D21; S22; E23; H24; S25; G26; K27; K31; Q33; R35; I36; G37; K48; G52; R54; T72; A79; N83; K85; P105; G107; R109; L118; N120; Q121; A122; T147; V148; N149; G150; I151; R152; H153. Residue E51 was deleted.

Another substituted sequence is SEQ ID NO:59. Another substituted sequence is SEQ ID NO:60.

Surface Loops for Substitution

Surface loops of SEQ ID NO: 1 have been identified as: (1) amino acids 164-168; (2) amino acids 179-182; (3) amino acids 188-196; (4) amino acids 203-208; (5) amino acids 216-224; (6) amino acids 233-237; (7) amino acids 247-251; and (8) amino acids 262-263:

```
MNRTAFCCLSLTTALILTACSSGGGGVAADIGAGLADALTAPLDHKDKG

LQSLTLDQSVRKNEKLKLAAQGAEKTYGNGDSLNTGKLKNDKVSRFDFI

RQIEVDGQLITLESGEFQVYKQSHSALTAFQTEQIQDSEHSGKMVAKRQ

FRIGDIAGEHTSFDKLPEGGRATYRGTAFGSDDAGGKLTYTIDFAAKQG

NGKIEHLKSPELNVDLAAADIKPDGKRHAVISGSVLYNQAEKGSYSLGI

FGGKAQEVAGSAEVKTVNGIRHIGLAAKQ
```

By aligning SEQ ID NO: 1 with any other NMB1870 sequence, the skilled person can identify the positions of loops (1) to (8) in that sequence. For ease of reference, however, the coordinates of a loop are defined herein as the string of amino acid(s) in a NMB1870 sequence that, when aligned to SEQ ID NO: 1 using a pairwise alignment algorithm, starts with the amino acid aligned to the first amino acid residue of the loop defined above in SEQ ID NO: 1 and ends with the last amino acid of the loop defined above in SEQ ID NO: 1.

Substitution of loop sequences from one family into the loop position in another family allows chimeric NMB1870 to be produced with multi-family antigenicity.

Thus the invention provides a polypeptide comprising a modified amino acid sequence of a first family of NMB1870, wherein the modified sequence includes at least one (e.g. 1, 2, 3, 4, 5, 6 or 7) surface loop sequence from a second family of NMB1870 in place of a surface loop sequence from the first family.

The invention also provides a polypeptide that comprises a backbone sequence in nine parts, with eight loop insertions (one between each consecutive part of backbone sequence), where at least one of the loop sequences is taken from a NMB1870 sequence that is from a different NMB1870 family from the backbone sequence. It is preferred to use surface loops from more than one different NMB1870 sequence, and it is possible to insert these loops into a single backbone sequence. Thus the invention provides a polypeptide comprising an amino acid sequence:

—$B_1$-$L_1$-$B_2$-$L_2$-$B_3$-$L_3$-$B_4$-$L_4$-$B_5$-$L_5$-$B_6$-$L_6$-$B_7$-$L_7$-$B_8$-$L_8$-$B_9$— wherein:

(a) each of said $B_1$, $B_2$, $B_3$, $B_4$, $B_5$, $B_6$, $B_7$, $B_8$ and $B_9$ is: (i) a fragment of SEQ ID NO: M; or (ii) an amino acid sequence having at least m % sequence identity to said fragment of (i) and/or comprising a fragment of at least d contiguous amino acids from said fragment of (i);

(b) each of said $L_1$, $L_2$, $L_3$, $L^4$, $L_5$, $L_6$, $L_7$ and $L_8$ is: (i) a fragment of SEQ ID NO: 2 and/or of SEQ ID NO: 3; or (ii) an amino acid sequence having at least n % sequence identity, to said fragment of (i) and/or comprising a fragment of at least e contiguous amino acids from said fragment of (i), provided that at least one of said $L_1$, $L_2$, $L_3$, $L_4$, $L_5$, $L_6$, $L_7$ and $L_8$ is not a fragment of SEQ ID NO: M.

The invention also provides a fragment of said polypeptide, provided that the fragment includes at least one of $L_1$, $L_2$, $L_3$, $L_4$, $L_5$, $L_6$, $L_7$ and/or $L_8$ and at least one amino acid from two or more of $B_1$, $B_2$, $B_3$, $B_4$, $B_5$, $B_6$, $B_7$, $B_8$ and/or $B_9$. Thus in some embodiments the smallest fragment includes one loop, one amino acid to the N-terminus of that loop and one amino acid to the C-terminus of that loop.

The value of M is selected from 1, 2 or 3, and the definitions of $B_1$, $B_2$, $B_3$, $B_4$, $B_5$, $B_6$, $B_7$, $B_8$ and $B_9$ and of $L_1$, $L_2$, $L_3$, $L_4$, $L_5$, $L_6$, $L_7$ and $L_8$ vary depending on the value of M.

The meaning of "(i) a fragment of SEQ ID NO: M" is as follows:

| | Amino acid co-ordinates within SEQ ID NO: M | | | | | | | | |
|---|---|---|---|---|---|---|---|---|---|
| M | $B_1$ | $B_2$ | $B_3$ | $B_4$ | $B_5$ | $B_6$ | $B_7$ | $B_8$ | $B_9$ |
| 1 | 1-163 | 169-178 | 183-187 | 197-202 | 209-215 | 225-232 | 238-246 | 252-261 | 264-274 |
| 2 | 1-163 | 168-177 | 182-186 | 196-201 | 208-214 | 224-231 | 237-245 | 251-260 | 263-273 |
| 3 | 1-171 | 176-185 | 190-194 | 204-209 | 216-222 | 232-239 | 245-253 | 259-268 | 271-281 |

Similarly, "(iii) a fragment of SEQ ID NO: 1, SEQ ID NO: 2 and/or of SEQ ID NO: 3" is defined as:

| | Amino acid co-ordinates within SEQ ID NO: 1, 2 or 3 | | | | | | | |
|---|---|---|---|---|---|---|---|---|
| SEQ | $L_1$ | $L_2$ | $L_3$ | $L_4$ | $L_5$ | $L_6$ | $L_7$ | $L_8$ |
| 1 | 164-168 | 179-182 | 188-196 | 203-208 | 216-224 | 233-237 | 247-251 | 262-263 |
| 2 | 164-167 | 178-181 | 187-195 | 202-207 | 215-223 | 232-236 | 246-250 | 261-262 |
| 3 | 172-175 | 186-189 | 195-203 | 210-215 | 223-231 | 240-244 | 254-258 | 269-270 |

For example, the invention provides a polypeptide comprising an amino acid sequence:

—$B_1$-$L_1$-$B_2$-$L_2$-$B_3$-$L_3$-$B_4$-$L_4$-$B_5$-$L_5$-$B_5$-$L_6$-$B_7$-$L_7$-$B_8$-$L_8$-$B_9$— wherein: $B_1$ is amino acids 1-163 of SEQ ID NO: 1, or an amino acid sequence having at least m% sequence identity to said amino acids 1-163 and/or comprising a fragment of at least d contiguous amino acids from said amino acids 1-163; $B_2$ is amino acids 169-178 of SEQ ID NO: 1, or an amino acid sequence having at least m % sequence identity to said amino acids 169-178 and/or comprising a fragment of at least d contiguous amino acids from said amino acids 169-178 . . . . $B_9$ is amino acids 264-274 of SEQ ID NO: 1, or an amino acid sequence having at least m % sequence identity to said amino acids 264-274 and/or comprising a fragment of at least d contiguous amino acids from said amino acids 264-274; $L_1$ is amino acids 164-168 of SEQ ID NO: 2, or an amino acid sequence having at least n % sequence identity to said amino acids 164-168 and/or comprising a fragment of at least e contiguous amino acids from said amino acids 164-168; $L_2$ is amino acids 179-182 of SEQ ID NO: 2, or an amino acid sequence having at least n % sequence identity to said amino acids 179-182 and/or comprising a fragment of at least e contiguous amino acids from said amino acids 179-182, . . . $L_7$ is amino acids 269-270 of SEQ ID NO: 3, or an amino acid sequence having at least n % sequence identity to said amino acids 269-270 and/or comprising a fragment of at least e contiguous amino acids from said amino acids 269-270; etc.

The value of m is selected from 50, 60, 70, 75, 80, 85, 90, 92, 94, 95, 96, 97, 98, 99, 99.5, 99.9 or more. The value of n is selected from 50, 60, 70, 75, 80, 85, 90, 92, 94, 95, 96, 97, 98, 99, 99.5, 99.9 or more. The value of d is selected from 6, 7, 8, 9, 10, 12, 14, 16, 18, 20, 22, 24, 26, 28, 30, 40, 45, 50, 60, 70, 75, 100 or more. The value of e is selected from 1, 2, 3, 4, 5, 6, 7, 8, 9 or 10. The value of e is preferably less than 20.

The invention also provides a polypeptide comprising the chimeric amino acid sequence:

—$B_1$-L1-B2-$L_2$-$B_3$-$L_3$-$B_4$-$L_4$-$B_5$-$L_5$-$B_6$-$L_6$-$B_7$-$L_7$-$B_8$-$L_8$-$B_9$— as defined above, and further comprising, either N-terminal to or C-terminal to said chimeric sequence, a NMB1870 sequence, wherein said NMB1870 sequence is in the same NMB1870 family as SEQ ID NO: M. Thus the polypeptide comprises both (i) a NMB1870 from a particular family and (ii) also a NMB1870 from the same family, but with at least one of its surface loops substituted for a different NMB1870 family.

The invention provides a polypeptide comprising an amino acid sequence that has an overall sequence identity to SEQ ID NO: Q of q %, wherein: the value of q is at least r; the sequence identity of said amino acid sequence to SEQ ID NO: Q is more than q % at the backbone regions of SEQ ID NO: Q; and the sequence identity of said amino acid sequence to SEQ ID NO: Q is less than q % at the loop regions of SEQ ID NO: Q. The value of r is selected from 80, 81, 82, 83, 84, 85, 86, 87, 88, 89, 90, 91, 92, 93, 94, 95, 96, 97; 98, 99, and 99.5.

The value of Q is 1, 2 or 3, and the boundaries of the loop regions and of the backbone regions are selected accordingly from the above tables ($L_1$ to $L_8$ being the loops, and $B_1$ to $B_9$ being the backbone).

Where Q is 1, the amino acid sequence in a loop region may have more than q % sequence identity to the corresponding loop region of SEQ ID NO: 2 or SEQ ID NO: 3. Where Q is 2, the amino acid sequence in a loop region may have more than q% sequence identity to the corresponding loop region of SEQ ID NO: 1 or SEQ ID NO: 3. Where Q is 3, the amino acid sequence in a loop region may have more than q% sequence identity to the corresponding loop region of SEQ ID NO: 1 or SEQ ID NO: 2.

Hybrid and Tandem Polypeptides

References 10 to 13 disclose hybrid polypeptides in which a single polypeptide chain includes a NMB1870 sequence and a different meningococcal polypeptide sequence. For instance, hybrids containing NMB1870 and NadA are disclosed in reference 10. Reference 12 discloses a specific subset of hybrid polypeptides, referred to as tandem polypeptides, in which a single polypeptide chain includes multiple NMB1870 sequences e.g. one from each family. The invention provides a number of new hybrid and tandem polypeptides.

In general, a hybrid polypeptide can be represented by the formula:

$$-A-[-X-L-]_n-B-$$

wherein X is an amino acid sequence comprising a Neisserial sequence, L is an optional linker amino acid sequence, A is an optional N-terminal amino acid sequence, B is an optional C-terminal amino acid sequence, and n is an integer greater than 1.

The value of n can be 2, 3, 4, 5, 6, 7, 8 or more, but is preferably 2 or 3. The -A- sequence is preferably at the N-terminus of the polypeptide, and the —B— sequence is preferably at the C-terminus of the polypeptide.

According to the invention, at least one of the —X— moieties is a NMB1870 sequence. Preferred NMB1870 sequences for use as —X— moieties are truncated up to and including the poly-glycine sequence found near the mature N-terminus i.e. they are ΔG sequences. The ΔG versions of SEQ ID NOs: 1 to 3 are SEQ ID NOs: 22 to 24, respectively.

For X moieties, particularly those other than $X_1$, it is preferred that the native leader peptide should be omitted. In one embodiment, the leader peptides will be deleted except for that of the —X— moiety located at the N-terminus of the hybrid polypeptide i.e. the leader peptide of $X_1$ will be retained, but the leader peptides of $X_2$ . . . $X_n$ will be omitted. This is equivalent to deleting all leader peptides and using the leader peptide of $X_1$ as moiety -A-.

For each n instances of [—X-L-], linker amino acid sequence -L- may be present or absent. For instance, when n=2 the hybrid may be $NH_2$—$X_1$-$L_1$-$X_2$-$L_2$-COOH, $NH_2$—$X_1$—$X_2$—COOH, $NH_2$—$X_1$-$L_1$-$X_2$—COOH, $NH_2$—$X_1$—$X_2$-$L_2$-COOH, etc. Linker amino acid sequence(s) -L- will typically be short (e.g. 20 or fewer amino acids i.e. 19, 18, 17, 16, 15, 14, 13, 12, 11, 10, 9, 8, 7, 6, 5, 4, 3, 2, 1). Examples include short peptide sequences which facilitate cloning, poly-glycine linkers (i.e. $Gly_n$ where n=2, 3, 4, 5, 6, 7, 8, 9, 10 or more), and histidine tags (i.e. $His_n$ where n=3, 4, 5, 6, 7, 8, 9, 10 or more). Other suitable linker amino acid sequences will be apparent to those skilled in the art. A useful linker is GSGGGG (SEQ ID NO: 15), with the Gly-Ser dipeptide being formed from a BamHI restriction site, thus aiding cloning and manipulation, and the $Gly_4$ tetrapeptide (SEQ ID NO: 16) is another typical poly-glycine linker. Another useful linker is SEQ ID NO: 17, which can optionally be preceded by a Gly-Ser dipeptide (SEQ ID NO: 18, from BamHI) or a Gly-Lys dipeptide (SEQ ID NO: 19, from HindIII)

-A- is an optional N-terminal amino acid sequence. This will typically be short (e.g. 40 or fewer amino acids i.e. 39, 38, 37, 36, 35, 34, 33, 32, 31, 30, 29, 28, 27, 26, 25, 24, 23, 22, 21, 20, 19, 18, 17, 16, 15, 14, 13, 12, 11, 10, 9, 8, 7, 6, 5, 4, 3, 2, 1). Examples include leader sequences to direct protein trafficking, or short peptide sequences which facilitate cloning or purification (e.g. histidine tags i.e. $His_n$ where n=3, 4, 5, 6, 7, 8, 9, 10 or more). Other suitable N-terminal amino acid sequences will be apparent to those skilled in the art. If X1 lacks its own N-terminus methionine, -A- may provide such a methionine residue in the translated polypeptide (e.g. -A- is a single Met residue). The Met may be to the N-terminus of a linker sequence such as SEQ ID NO: 17 (i.e. SEQ ID: 21), or at the N-terminus of a short sequence (e.g. SEQ ID NO: 26). Examples of -A- sequences include SEQ ID NOs: 21, 26 and 43.

—B— is an optional C-terminal amino acid sequence. This will typically be short (e.g. 40 or fewer amino acids i.e. 39, 38, 37, 36, 35, 34, 33, 32, 31, 30, 29, 28, 27, 26, 25, 24, 23, 22, 21, 20, 19, 18, 17, 16, 15, 14, 13, 12, 11, 10, 9, 8, 7, 6, 5, 4, 3, 2, 1). Examples include sequences to direct protein trafficking, short peptide sequences which facilitate cloning or purification (e.g. comprising histidine tags i.e. $His_n$ where n=3, 4, 5, 6, 7, 8, 9, 10 or more e.g. SEQ ID NO: 20), or sequences which enhance polypeptide stability. Other suitable C-terminal amino acid sequences will be apparent to those skilled in the art. One suitable —B— moiety is SEQ ID NO: 41, in which the Leu-Glu (SEQ ID NO: 44) upstream of SEQ ID NO: 20 arises from a XhoI restriction site.

In preferred hybrid polypeptides of the invention, one of the X moieties is a 'protein 936' sequence. Protein 936 was originally disclosed as SEQ ID NO 2884 in ref. 3 (SEQ ID NO: 14 herein), and a signal-truncated version of this sequence is SEQ ID NO: 25 herein. '936' sequences for use with the invention include sequences (i) having at least z % sequence identity to SEQ ID NO: 25, and/or (ii) comprising a fragment of at least f contiguous amino acids from SEQ ID NO: 25. The value of z is selected from 50, 60, 70, 75, 80, 85, 90, 92, 94, 95, 96, 97, 98, 99, 99.5, 99.9 or more. The value of f is selected from 6, 7, 8, 9, 10, 12, 14, 16, 18, 20, 22, 24, 26, 28, 30, 40, 45, 50, 60, 70, 75, 100, 150, 200 or more.

Some preferred hybrid polypeptides include a 936 sequence and two NMB1870 sequences. The two NMB1870 sequences will be from two different families e.g. I & II, I & III, or II & III. Preferred hybrids include a 936 sequence, a family I NMB1870 sequence and a family H NMB1870 sequence. The 936 is preferably the most N-terminal of these three sequences. SEQ ID NOs: 28, 29, 34 & 35 are examples of hybrid polypeptides including a 936 sequence to the N-terminus of NMB1870 sequences from two different families.

For example, where n=2 then $X_1$ may be a '936' sequence and $X_2$ may be a NMB1870 sequence. Similarly, where n=3 then $X_1$ may be a '936' sequence and $X_2$ may be a NMB1870 sequence from a first family, and $X_2$ may be a NMB1870 sequence from a second family.

In preferred tandem polypeptides of the invention n is 2 or 3.

Fourteen specific hybrid and tandem polypeptides of the invention are disclosed as SEQ ID NOs: 27 to 40 which, for guidance, are built up from SEQ ID NOs as follows:

| SEQ ID | n | A | $X_1$ | $L_1$ | $X_2$ | $L_2$ | $X_3$ | $L_3$ | B |
|---|---|---|---|---|---|---|---|---|---|
| 27 | 2 | 21 | 23 | 15 | 22 | 44 | — | — | 20 |
| 28 | 3 | 26 | 25 | 15 | 22 | 18 | 23 | 44 | 20 |
| 29 | 3 | 26 | 25 | 18 | 23 | 45 | 22 | 44 | 20 |
| 30 | 3 | 21 | 23 | 15 | 22 | 18 | 24 | 42 | 20 |
| 31 | 3 | 21 | 23 | 18 | 24 | 15 | 22 | 44 | 20 |
| 32 | 3 | 43 | 22 | 18 | 23 | 18 | 24 | 42 | 20 |
| 33 | 2 | 21 | 23 | 15 | 22 | — | — | — | — |
| 34 | 3 | 26 | 25 | 15 | 22 | 18 | 23 | — | — |
| 35 | 3 | 26 | 25 | 18 | 23 | 15 | 22 | — | — |
| 36 | 3 | 21 | 23 | 18 | 24 | 15 | 22 | — | — |

-continued

| SEQ ID | n | A | $X_1$ | $L_1$ | $X_2$ | $L_2$ | $X_3$ | $L_3$ | B |
|---|---|---|---|---|---|---|---|---|---|
| 37 | 3 | 21 | 23 | 15 | 22 | 18 | 24 | — | — |
| 38 | 3 | 43 | 22 | 18 | 23 | 18 | 24 | — | — |
| 39 | 3 | 43 | 22 | 18 | 24 | 19 | 23 | 44 | 20 |
| 40 | 3 | 43 | 22 | 18 | 24 | 19 | 23 | — | — |

Further preferred hybrid and tandem polypeptides of the invention include a family IV sequence. Thus at least one X moiety may (i) have at least v % sequence identity to SEQ ID NO: 95, and/or (ii) comprise a fragment of at least vv contiguous amino acids from SEQ ID NO: 95. The value of v is selected from 50, 60, 70, 75, 80, 85, 90, 92, 94, 95, 96, 97, 98, 99, 99.5, 99.9 or more. The value of vv is selected from 6, 7, 8, 9, 10, 12, 14, 16, 18, 20, 22, 24, 26, 28, 30, 40, 45, 50, 60, 70, 75, 100, 150, 200 or more. By including a family IV sequence, serum activity against 269 cpx strains can be improved.

Fragments and Domains of NMB1870

Rather than use a full-length NMB1870 sequence (e.g. SEQ ID NO: 1), the invention will typically use a fragment. For instance, the amino acids upstream of the mature N-terminus (Cys-20 in SEQ ID NO: 1) will generally be omitted. Preferably, a "ΔG" sequence will be used, in which all of the amino acids up to and including NMB1870's poly-glycine sequence are deleted i.e. deletion of amino acids 1-26 in SEQ ID NO: 1. In SEQ ID NOs: 27 to 40, for instance, the above table shows that ΔG forms of NMB1870 (i.e. SEQ ID NOs: 22 to 24) are used.

As disclosed in reference 13, NMB1870 can be split into three domains, referred to as A, B and C. Taking the family I sequence (SEQ ID NO: 1), in which the N-terminus of the mature processed lipoprotein is Cys-20, the three domains are (A) 1-119, (B) 120-183 and (C) 184-274:

MNRTAFCCLSLTTALILTACSSGGGGVAADIGAGLADALTAPLDHKDKG

LQSLTLDQSVRKNEKLKLAAQGAEKTYGNGDSLNTGKLKNDKVSRFDFI

RQIEVDGQLITLESGEFQVYKQSHSALTAFQTEQIQDSEHSGKMVAKRQ

FRIGDIAGEHTSFDKLPEGGRATYRGTAFGSDDAGGKLTYTIDFAAKQG

NGKIEHLKSPELNVDLAAADIKPDGKRHAVISGSVLYNQAEKGSYSLGI

FGGKAQEVAGSAEVKTVNGIRHIGLAAKQ

The mature form of domain 'A', from its C-terminus cysteine, is called '$A_{mature}$'.

For MC58, the domains are: 'A'=SEQ ID NO: 4; 'B'=SEQ ID NO: 5;=SEQ ID NO: 6; and '$A_{mature}$'=SEQ ID NO: 13. Multiple NMB1870 sequences are known [e.g. see refs. 4, 8 and 10] and can readily be aligned using standard methods. By such alignments the skilled person can identify domains 'A' (and '$A_{mature}$'), 'B' and in any given NMB1870 sequence by comparison to the coordinates in the MC58 sequence. For ease of reference, however, the domains are defined below:

Domain 'A' in a given NMB1870 sequence is the fragment of that sequence which, when aligned to SEQ ID NO: 1 using a pairwise alignment algorithm, starts with the amino acid aligned to Met-1 of SEQ ID NO: 1 and ends with the amino acid aligned to Lys-119 of SEQ ID NO: 1.

Domain '$A_{mature}$' in a given NMB1870 sequence is the fragment of that sequence which, when aligned to SEQ ID NO: 1 using a pairwise alignment algorithm, starts with the amino acid aligned to Cys-20 of SEQ ID NO: 1 and ends with the amino acid aligned to Lys-119 of SEQ ID NO: 1.

Domain 'B' in a given NMB1870 sequence is the fragment of that sequence which, when aligned to SEQ ID NO: 1 using a pairwise alignment algorithm, starts with the amino acid aligned to Gln-120 of SEQ ID NO: 1 and ends with the amino acid aligned to Gly-183 of SEQ ID NO: 1.

Domain 'C' in a given NMB1870 sequence is the fragment of that sequence which, when aligned to SEQ ID NO: 1 using a pairwise alignment algorithm, starts with the amino acid aligned to Lys-184 of SEQ ID NO: 1 and ends with the amino acid aligned to Gln-274 of SEQ ID NO 1.

The preferred pairwise alignment algorithm for defining the domains is the Needleman-Wunsch global alignment algorithm [14], using default parameters (e.g. with Gap opening penalty=10.0, and with Gap extension penalty=0.5, using the EBLOSUM62 scoring matrix). This algorithm is conveniently implemented in the needle tool in the EMBOSS package [15].

NMB1870 sequences fall into three families [4,10] that are referred to herein as families I, II and III. The prototypic sequences for families I-III are, respectively, SEQ ID NOS: 1-3. The phylogenetic and dendrogram methods of reference 4 can be followed in order to readily determine the family for any given NMB1870 sequence, and a pairwise alignment with each of the three prototypic NMB1870 sequences can also be used to find the closest family match. Sequences fall distinctly into the three families, with sequence identity being 74.1% between families I & II, 62.8% between families I & III and 84.7% between families II & III, and with sequence variation within each family being low (e.g. a minimum of 91.6% identity in family I, 93.4% in family II and 93.2% in family III). As a quick way of determining a sequence's family without requiring a phylogenetic analysis, a sequence can be placed in family I if it has at least 85% sequence identity to SEQ ID NO: 1, can be placed in family II if it has at least 85% sequence identity to SEQ ID NO: 2, and can be placed in family III if it has at least 85% sequence identity to SEQ ID NO: 3.

Based on the alignment in FIG. 6 of reference 4, exemplary domains A, B and C for the three prototypic families of NMB1870 (SEQ ID NOS: 1 to 3) are as follows:

| ↓Family Domain→ | A | B | C |
|---|---|---|---|
| I | SEQ ID NO: 4 | SEQ ID NO: 5 | SEQ ID NO: 6 |
| II | SEQ ID NO: 7 | SEQ ID NO: 8 | SEQ ID NO: 9 |
| III | SEQ ID NO: 10 | SEQ ID NO: 11 | SEQ ID NO: 12 |

Preferred domains for use with the invention comprise amino acid sequences that (a) have at least x % sequence identity to one or more of SEQ ID NOS: 4 to 12, and/or (a) comprise a fragment of at least y consecutive amino acids sequence from one or more of SEQ ID NOS: 4 to 12.

The value of x is selected from 50, 60, 70, 75, 80, 85, 90, 92, 94, 95, 96, 97, 98, 99, 99.5, 99.9 or more. The value of y is selected from 6, 7, 8, 9, 10, 11, 12, 13, 14, 15, 16, 17, 18, 19, 20, 22, 24, 26, 28, 30, 35, 40, 45, 50 or more. In polypeptides comprising NMB1870 sequences from different families, the values of x and y for each family can be the same or different.

A domain 'A' sequence is preferably between $a_1$ and $a_2$ (inclusive) amino acids long, where: $a_1$ is selected from 110, 115, 120, 125 and 130; and $a_2$ is selected from 115, 120, 125, 130 and 135.

A domain 'B' sequence is preferably between $b_1$ and $b_2$ (inclusive) amino acids long, where: $b_1$ is selected from 55, 60, 65 and 70; and $b_2$ is selected from 60, 65, 70 and 75.

A domain 'C' sequence is preferably between $c_1$ and $c_2$ (inclusive) amino acids long, where: $c_1$ is selected from 80, 85, 90, 95 and 100; and $c_2$ is selected from 85, 90, 95, 100 and 105.

As desired, any full-length form of NMB1870 can be replaced by a single NMB1870 domain (A, B or C) or by two NMB1870 domains (AB, AC or BC).

Polymorphic Forms of NMB1870

Various polymorphic forms of NMB1870 have previously been reported. New sequences have been identified, and so the invention provides a polypeptide comprising an amino acid sequence selected from the group consisting of SEQ ID NOs: 46, 47, 48, 49, 50, 51, 52, 53, 54, 55, 56, 86, 87, 88, 89, 90, 91, 92, 93 and 94. SEQ ID NO: 94 (see also SEQ ID NO: 140 of ref. 12) is an example of a family IV sequence, which may have arisen by recombination between families I and III.

Polypeptides

The invention provides the polypeptides various described above.

It also provides a polypeptide comprising an amino acid sequence selected from the group consisting of SEQ ID NOs: 27, 28, 29, 30, 31, 32, 33, 34, 35, 36, 37, 38, 39, 40, 46, 47, 48, 49, 50, 51, 52, 53, 54, 55 and 56. It also provides polypeptides having an amino acid sequence (a) having sequence identity to an amino acid sequence selected from the group consisting of SEQ ID NOS: 27, 28, 29, 30, 31, 32, 33, 34, 35, 36, 37, 38, 39, 40, 46, 47, 48, 49, 50, 51, 52, 53, 54, 55 and 56 and/or (b) comprising a fragment of an amino acid sequence selected from the group consisting of SEQ ID NOS: 27, 28, 29, 30, 31, 32, 33, 34, 35, 36, 37, 38, 39, 40, 46, 47, 48, 49, 50, 51, 52, 53, 54, 55 and 56. The degree of sequence identity is preferably greater than 50% (e.g. 60%, 70%, 80%, 90%, 95%, 99% or more). The fragment preferably comprises 7 or more consecutive amino acids from the starting sequence (e.g. 7, 8, 9, 10, 11, 12, 13, 14, 15, 16, 17, 18, 19, 20, 22, 24, 26, 28, 30, 32, 34, 36, 38, 40, 45, 50, 55, 60, 65, 70, 75, 70, 85, 90, 95, 100 or more).

NMB1870 is naturally a lipoprotein in *N. meningitidis*. It has also been found to be lipidated when expressed in *E. coli*. Polypeptides of the invention may have a C-terminus cysteine residue, which may be lipidated e.g. comprising a palmitoyl group.

A characteristic of preferred polypeptides of the invention is the ability to induce bactericidal anti-meningococcal antibodies after administration to a host animal.

Polypeptides of the invention can be prepared by various means e.g. by chemical synthesis (at least in part), by digesting longer polypeptides using proteases, by translation from RNA, by purification from cell culture (e.g. from recombinant expression or from *N. meningitidis* culture). etc.

Heterologous expression in an *E. coli* host is a preferred expression route (e.g. in DH5α, BL21($DE_3$), BLR, etc.).

Polypeptides of the invention may be attached or immobilised to a solid support.

Polypeptides of the invention may comprise a detectable label e.g. a radioactive label, a fluorescent label, or a biotin label. This is particularly useful in immunoassay techniques.

Polypeptides can take various forms (e.g. native, fusions, glycosylated, non-glycosylated, lipidated, disulfide bridges, etc.).

Polypeptides are preferably prepared in substantially pure or substantially isolated form (i.e. substantially free from other Neisserial or host cell polypeptides) or substantially isolated form. In general, the polypeptides are provided in a non-naturally occurring environment e.g. they are separated from their naturally-occurring environment. In certain embodiments, the subject polypeptide is present in a composition that is enriched for the polypeptide as compared to a control. As such, purified polypeptide is provided, whereby purified is meant that the polypeptide is present in a composition that is substantially free of other expressed polypeptides, where by substantially free is meant that less than 90%, usually less than 60% and more usually less than 50% of the composition is made up of other expressed polypeptides.

The term "polypeptide" refers to amino acid polymers of any length. The polymer may be linear or branched, it may comprise modified amino acids, and it may be interrupted by non-amino acids. The terms also encompass an amino acid polymer that has been modified naturally or by intervention; for example, disulfide bond formation, glycosylation, lipidation, acetylation, phosphorylation, or any other manipulation or modification, such as conjugation with a labeling component. Also included within the definition are, for example, polypeptides containing one or more analogs of an amino acid (including, for example, unnatural amino acids, etc.), as well as other modifications known in the art. Polypeptides can occur as single chains or associated chains.

Nucleic Acids

The invention provides nucleic acid encoding a polypeptide of the invention as defined above. The invention also provides nucleic acid comprising: (a) a fragment of at least n consecutive nucleotides from said nucleic acid, wherein n is 10 or more (e.g. 12, 14, 15, 18, 20, 25, 30, 35, 40, 50, 60, 70, 80, 90, 100, 150, 200, 500 or more); and/or (b) a sequence having at least 50% (e.g. 60%, 70%, 80%, 90%, 95%, 96%, 97%, 98%, 99% or more) sequence identity to said nucleic acid.

Furthermore, the invention provides nucleic acid which can hybridise to nucleic acid encoding a polypeptide of the invention, preferably under "high stringency" conditions (e.g. 65° C. in a 0.1×SSC, 0.5% SDS solution).

Nucleic acids of the invention can be used in hybridisation reactions (e.g. Northern or Southern blots, or in nucleic acid microarrays or 'gene chips') and amplification reactions (e.g. PCR, SDA, SSSR, LCR, TMA, NASBA, etc.) and other nucleic acid techniques.

Nucleic acids of the invention may be prepared in many ways e.g. by chemical synthesis (e.g. phosphoramidite synthesis of DNA) in whole or in part, by digesting longer nucleic acids using nucleases (e.g. restriction enzymes), by joining shorter nucleic acids or nucleotides (e.g. using ligases or polymerases), from genomic or cDNA libraries, etc.

Nucleic acids of the invention can take various forms e.g. single-stranded, double-stranded, vectors, primers, probes, labelled, unlabelled, etc.

Nucleic acids of the invention are preferably in isolated or substantially isolated form.

The invention includes nucleic acid comprising sequences complementary to those described above e.g. for antisense or probing, or for use as primers.

The term "nucleic acid" includes DNA and RNA, and also their analogues, such as those containing modified backbones, and also peptide nucleic acids (PNA), etc.

Nucleic acid according to the invention may be labelled e.g. with a radioactive or fluorescent label. This is particularly useful where the nucleic acid is to be used in nucleic acid detection techniques e.g. where the nucleic acid is a primer or as a probe for use in techniques such as PCR, LCR, TMA, NASBA, etc.

The invention also provides vectors comprising nucleotide sequences of the invention (e.g. cloning or expression vectors, such as those suitable for nucleic acid immunisation) and host cells transformed with such vectors.

Bactericidal Responses

Preferred polypeptides of the invention can elicit antibody responses that are bactericidal against meningococci. Bactericidal antibody responses are conveniently measured in mice and are a standard indicator of vaccine efficacy [e.g. see end-note 14 of reference 2]. Polypeptides of the invention can preferably elicit an antibody response which is bactericidal against at least one *N. meningitidis* strain from each of at least two of the following three groups of strains:

(I) MC58, gb185 (=M01-240185), m4030, m2197, m2937, iss1001, NZ394/98, 67/00, 93/114, bz198, m1390, nge28, 1np17592, 00-241341, f6124, 205900, m198/172, bz133, gb149 (=M01-240149), nm008, nm092, 30/00, 39/99, 72/00, 95330, bz169, bz83, cu385, h44/76, m1590, m2934, m2969, m3370, m4215, m4318, n44/89, 14847.

(II) 961-5945, 2996, 96217, 312294, 11327, a22, gb013 (=M01-240013), e32, m1090, m4287, 860800, 599, 95N477, 90-18311, c11, m986, m2671, 1000, m1096, m3279, bz232, dk353, m3697, ngh38, L93/4286.

(III) M1239, 16889, gb355 (=M01-240355), m3369, m3813, ngp165.

For example, a chimeric polypeptide can elicit a bactericidal response effective against two or more of serogroup B *N. meningitidis* strains MC58, 961-5945 and M1239.

The polypeptide can preferably elicit an antibody response which is bactericidal against at least 50% of clinically-relevant meningococcal serogroup B strains (e.g. 60%, 70%, 80%, 90%, 95% or more). The polypeptide may elicit an antibody response which is bactericidal against strains of serogroup B *N. meningitidis* and strains of at least one (e.g. 1, 2, 3, 4) of serogroups A, C, W135 and Y. The polypeptide may elicit an antibody response which is bactericidal against strains of *N. gonococcus* and/or *N. cinerea*. The polypeptide may elicit a response which is bactericidal against strains from at least two of the three main branches of the dendrogram shown in FIG. 5 of reference 4.

The polypeptide may elicit an antibody response which is bactericidal against *N. meningitidis* strains in at least 2 (e.g. 2, 3, 4, 5, 6, 7) of hypervirulent lineages ET-37, ET-5, cluster A4, lineage 3, subgroup I, subgroup III, and subgroup IV-1 [16, 17]. Polypeptides may additionally induce bactericidal antibody responses against one or more hyperinvasive lineages.

Polypeptides may elicit an antibody response which is bactericidal against *N. meningitidis* strains in at least at least 2 (e.g. 2, 3, 4, 5, 6, 7) of the following multilocus sequence types: ST1, ST4, ST5, ST8, ST11, ST32 and ST41 [18]. The polypeptide may also elicit an antibody response which is bactericidal against ST44 strains.

The polypeptide need not induce bactericidal antibodies against each and every MenB strain within the specified lineages or MLST; rather; for any given group of four of more strains of serogroup B meningococcus within a particular hypervirulent lineage or MLST, the antibodies induced by the composition are preferably bactericidal against at least 50% (e.g. 60%, 70%, 80%, 90% or more) of the group. Preferred groups of strains will include strains isolated in at least four of the following countries: GB, AU, CA, NO, IT, US, NZ, NL, BR, and CU. The serum preferably has a bactericidal titre of at least 1024 (e.g. $2^{10}$, $2^{11}$, $2^{12}$, $2^{13}$, $2^{14}$, $2^{15}$, $2^{16}$, $2^{17}$, $2^{18}$ or higher, preferably at least $2^{14}$) i.e. the serum is able to kill at least 50% of test bacteria of a particular strain when diluted 1:1024 e.g. as described in end-note 14 of reference 2. Preferred chimeric polypeptides can elicit an antibody response in mice that remains bactericidal even when the serum is diluted 1:4096 or further.

Immunisation

Polypeptides of the invention are preferably provided as immunogenic compositions, and the invention provides an immunogenic composition of the invention for use as a medicament.

The invention also provides a method for raising an antibody response in a mammal, comprising administering an immunogenic composition of the invention to the mammal. The antibody response is preferably a protective and/or bactericidal antibody response.

The invention also provides a method for protecting a mammal against a Neisserial (e.g. meningococcal) infection, comprising administering to the mammal an immunogenic composition of the invention.

The invention provides chimeric polypeptides of the invention for use as medicaments (e.g. as immunogenic compositions or as vaccines) or as diagnostic reagents. It also provides the use of nucleic acid, polypeptide, or antibody of the invention in the manufacture of a medicament for preventing Neisserial (e.g. meningococcal) infection in a mammal.

The mammal is preferably a human. The human may be an adult or, preferably, a child. Where the vaccine is for prophylactic use, the human is preferably a child (e.g. a toddler or infant); where the vaccine is for therapeutic use, the human is preferably an adult. A vaccine intended for children may also be administered to adults e.g. to assess safety, dosage, immunogenicity, etc.

The uses and methods are particularly useful for preventing/treating diseases including, but not limited to, meningitis (particularly bacterial meningitis) and bacteremia.

Efficacy of therapeutic treatment can be tested by monitoring Neisserial infection after administration of the composition of the invention. Efficacy of prophylactic treatment can be tested by monitoring immune responses against NMB1870 after administration of the composition. Immunogenicity of compositions of the invention can be determined by administering them to test subjects (e.g. children 12-16 months age, or animal models [19]) and then determining standard parameters including serum bactericidal antibodies (SBA) and ELISA titres (GMT). These immune responses will generally be determined around 4 weeks after administration of the composition, and compared to values determined before administration of the composition. A SBA increase of at least 4-fold or 8-fold is preferred. Where more than one dose of the composition is administered, more than one post-administration determination may be made.

Preferred compositions of the invention can confer an antibody titre in a patient that is superior to the criterion for seroprotection for each antigenic component for an acceptable percentage of human subjects. Antigens with an associated antibody titre above which a host is considered to be seroconverted against the antigen are well known, and such titres are published by organisations such as WHO. Preferably more than 80% of a statistically significant sample of subjects is seroconverted, more preferably more than 90%, still more preferably more than 93% and most preferably 96-100%.

Compositions of the invention will generally be administered directly to a patient. Direct delivery may be accomplished by parenteral injection (e.g. subcutaneously, intraperitoneally, intravenously, intramuscularly, or to the interstitial space of a tissue), or by rectal, oral, vaginal, topical, transdermal, intranasal, ocular, aural, pulmonary or other mucosal administration. Intramuscular administration to the thigh or the upper arm is preferred. Injection may be via a needle (e.g. a hypodermic needle), but needle-free injection may alternatively be used. A typical intramuscular dose is about 0.5 ml.

The invention may be used to elicit systemic and/or mucosal immunity.

Dosage treatment can be a single dose schedule or a multiple dose schedule. Multiple doses may be used in a primary immunisation schedule and/or in a booster immunisation schedule. A primary dose schedule may be followed by a booster dose schedule. Suitable timing between priming doses (e.g. between 4-16 weeks), and between priming and boosting, can be routinely determined.

The immunogenic composition of the invention will generally, include a pharmaceutically acceptable carrier, which can be any substance that does not itself induce the production of antibodies harmful to the patient receiving the composition, and which can be administered without undue toxicity. Pharmaceutically acceptable carriers can include liquids such as water, saline, glycerol and ethanol. Auxiliary substances, such as wetting or emulsifying agents, pH buffering substances, and the like, can also be present in such vehicles. A thorough discussion of suitable carriers is available in ref. 20.

Neisserial infections affect various areas of the body and so the compositions of the invention may be prepared in various forms. For example, the compositions may be prepared as injectables, either as liquid solutions or suspensions. Solid forms suitable for solution in, or suspension in, liquid vehicles prior to injection can also be prepared. The composition may be prepared for topical administration e.g. as an ointment, cream or powder. The composition be prepared for oral administration e.g. as a tablet or capsule, or as a syrup (optionally flavoured). The composition may be prepared for pulmonary administration e.g. as an inhaler, using a fine powder or a spray. The composition may be prepared as a suppository or pessary. The composition may be prepared for nasal, aural or ocular administration e.g. as drops.

The composition is preferably sterile. It is preferably pyrogen-free. It is preferably buffered e.g. at between pH 6 and pH 8, generally around pH 7. Where a composition comprises an aluminium hydroxide salt, it is preferred to use a histidine buffer [21]. Compositions of the invention may be isotonic with respect to humans.

Immunogenic compositions comprise an immunologically effective amount of immunogen, as well as any other of other specified components, as needed. By ‘immunologically effective amount’, it is meant that the administration of that amount to an individual, either in a single dose or as part of a series, is effective for treatment or prevention. This amount varies depending upon the health and physical condition of the individual to be treated, age, the taxonomic group of individual to be treated (e.g. non-human primate, primate, etc.), the capacity of the individual’s immune system to synthesise antibodies, the degree of protection desired, the formulation of the vaccine, the treating doctor’s assessment of the medical situation, and other relevant factors. It is expected that the amount will fall in a relatively broad range that can be determined through routine trials. Dosage treatment may be a single dose schedule or a multiple dose schedule (e.g. including booster doses). The composition may be administered in conjunction with other immunoregulatory agents.

Adjuvants which may be used in compositions of the invention include, but are not limited to:

A. Mineral-Containing Compositions

Mineral containing compositions suitable for use as adjuvants in the invention include mineral salts, such as aluminium salts and calcium salts. The invention includes mineral salts such as hydroxides (e.g. oxyhydroxides), phosphates (e.g. hydroxyphosphates, orthophosphates), sulphates, etc. [e.g. see chapters 8 & 9 of ref. 22], or mixtures of different mineral compounds, with the compounds taking any suitable form (e.g. gel, crystalline, amorphous, etc.), and with adsorption being preferred. The mineral containing compositions may also be formulated as a particle of metal salt [23].

Aluminium phosphates are particularly preferred, particularly in compositions which include a *H. influenzae* saccharide antigen, and a typical adjuvant is amorphous aluminium hydroxyphosphate with $PO_4/Al$ molar ratio between 0.84 and 0.92, included at 0.6mg $Al^{3+}$/ml. Adsorption with a low dose of aluminium phosphate may be used e.g. between 50 and 100 μg $Al^{3+}$ per conjugate per dose. Where there is more than one conjugate in a composition, not all conjugates need to be adsorbed.

B. Oil Emulsions

Oil emulsion compositions suitable for use as adjuvants in the invention include squalene-water emulsions, such as MF59 [Chapter 10 of ref. 22; see also ref. 24] (5% Squalene, 0.5% Tween 80, and 0.5% Span 85, formulated into submicron particles using a microfluidizer). Complete Freund's adjuvant (CFA) and incomplete Freund's adjuvant (IFA) may also be used. Oil-in-water emulsions adjuvants are useful with the invention.

C. Saponin Formulations [Chapter 22 of Ref. 22]

Saponin formulations may also be used as adjuvants in the invention. Saponins are a heterologous group of sterol glycosides and triterpenoid glycosides that are found in the bark, leaves, stems, roots and even flowers of a wide range of plant species. Saponin from the bark of the *Quillaia saponaria* Molina tree have been widely studied as adjuvants. Saponin can also be commercially obtained from *Smilax ornata* (sarsaprilla), *Gypsophilla paniculata* (brides veil), and *Saponaria officianalis* (soap root). Saponin adjuvant formulations include purified formulations, such as QS21, as well as lipid formulations, such as ISCOMs. QS21 is marketed as Stimulon™.

Saponin compositions have been purified using HPLC and RP-HPLC. Specific purified fractions using these techniques have been identified, including QS7, QS17, QS18, QS21, QH-A, QH-B and QH-C. Preferably, the saponin is QS21. A method of production of QS21 is disclosed in ref. 25. Saponin formulations may also comprise a sterol, such as cholesterol [26].

Combinations of saponins and cholesterols can be used to form unique particles called immunostimulating complexs (ISCOMs) [chapter 23 of ref. 22]. ISCOMs typically also include a phospholipid such as phosphatidylethanolamine or phosphatidylcholine. Any known saponin can be used in ISCOMs. Preferably, the ISCOM includes one or more of QuilA, QHA & QHC. ISCOMs are further described in refs. 26-28. Optionally, the ISCOMS may be devoid of additional detergent [29].

A review of the development of saponin based adjuvants can be found in refs. 30 & 31.

D. Virosomes and Virus-Like Particles

Virosomes and virus-like particles (VLPs) can also be used as adjuvants in the invention. These structures generally contain one or more proteins from a virus optionally combined or formulated with a phospholipid. They are generally non-pathogenic, non-replicating and generally do not contain any of the native viral genome. The viral proteins may be recombinantly produced or isolated from whole viruses. These viral proteins suitable for use in virosomes or VLPs include proteins derived from influenza virus (such as HA or NA), Hepatitis B virus (such as core or capsid proteins), Hepatitis E virus, measles virus, Sindbis virus, Rotavirus, Foot-and-Mouth Disease virus, Retrovirus, Norwalk virus, human Papilloma virus, HIV, RNA-phages, Qβ-phage (such as coat proteins), GA-phage, fr-phage, AP205 phage, and Ty (such as retrotransposon Ty protein p 1). VLPs are discussed further in refs. 32-37. Virosomes are discussed further in, for example, ref. 38

E. Bacterial or Microbial Derivatives

Adjuvants suitable for use in the invention include bacterial or microbial derivatives such as non-toxic derivatives of enterobacterial lipopolysaccharide (LPS), Lipid A derivatives, immunostimulatory oligonucleotides and ADP-ribosylating toxins and detoxified derivatives thereof.

Non-toxic derivatives of LPS include monophosphoryl lipid A (MPL) and 3-O-deacylated MPL (3dMPL). 3dMPL is a mixture of 3 de-O-acylated monophosphoryl lipid A with 4, 5 or 6 acylated chains. A preferred "small particle" form of 3 De-O-acylated monophosphoryl lipid A is disclosed in ref. 39. Such "small particles" of 3dMPL are small enough to be sterile filtered through a 0.22 μm membrane [39]. Other non-toxic LPS derivatives include monophosphoryl lipid A mimics, such as aminoalkyl glucosaminide phosphate derivatives e.g. RC-529 [40,41].

Lipid A derivatives include derivatives of lipid A from *Escherichia coli* such as 0M-174. OM-174 is described for example in refs. 42 & 43.

Immunostimulatory oligonucleotides suitable for use as adjuvants in the invention include nucleotide sequences containing a CpG motif (a dinucleotide sequence containing an unmethylated cytosine linked by a phosphate bond to a guanosine). Double-stranded RNAs and oligonucleotides containing palindromic or poly(dG) sequences have also been shown to be immunostimulatory.

The CpG's can include nucleotide modifications/analogs such as phosphorothioate modifications and can be double-stranded or single-stranded. References 44, 45 and 46 disclose possible analog substitutions e.g. replacement of guanosine with 2'-deoxy-7-deazaguanosine. The adjuvant effect of CpG oligonucleotides is further discussed in refs. 47-52.

The CpG sequence may be directed to TLR9, such as the motif GTCGTT or TTCGTT [53]. The CpG sequence may be specific for inducing a Th1 immune response, such as a CpG-A ODN, or it may be more specific for inducing a B cell response, such a CpG-B ODN. CpG-A and CpG-B ODNs are discussed in refs. 54-56. Preferably, the CpG is a CpG-A ODN.

Preferably, the CpG oligonucleotide is constructed so that the 5' end is accessible for receptor recognition. Optionally, two CpG oligonucleotide sequences may be attached at their 3' ends to form "immunomers". See, for example, refs. 53 & 57-59.

Bacterial ADP-ribosylating toxins and detoxified derivatives thereof may be used as adjuvants in the invention. Preferably, the protein is derived from *E. coli* (*E. coli* heat labile enterotoxin "LT"), cholera ("CT"), or pertussis ("PT"). The use of detoxified ADP-ribosylating toxins as mucosal adjuvants is described in ref. 60 and as parenteral adjuvants in ref. 61. The toxin or toxoid is preferably in the form of a holotoxin, comprising both A and B subunits. Preferably, the A subunit contains a detoxifying mutation; preferably the B subunit is not mutated. Preferably, the adjuvant is a detoxified LT mutant such as LT-K63, LT-R72, and LT-G192. The use of ADP-ribosylating toxins and detoxified derivaties thereof, particularly LT-K63 and LT-R72, as adjuvants can be found in refs. 62-69. Numerical reference for amino acid substitutions is preferably based on the alignments of the A and B subunits of ADP-ribosylating toxins set forth in ref. 70, specifically incorporated herein by reference in its entirety.

F. Human Immunomodulators

Human immunomodulators suitable for use as adjuvants in the invention include cytokines, such as interleukins (e.g. IL-1, IL-2, IL-4, IL-5, IL-6, IL-7, IL-12 [71], etc.) [72], interferons (e.g. interferon-γ), macrophage colony stimulating factor, and tumor necrosis factor.

G. Bioadhesives and Mucoadhesives

Bioadhesives and mucoadhesives may also be used as adjuvants in the invention. Suitable bioadhesives include esterified hyaluronic acid microspheres [73] or mucoadhesives such as cross-linked derivatives of poly(acrylic acid), polyvinyl alcohol, polyvinyl pyrollidone, polysaccharides and carboxymethylcellulose. Chitosan and derivatives thereof may also be used as adjuvants in the invention [74].

H. Microparticles

Microparticles may also be used as adjuvants in the invention. Microparticles (i.e. a particle of ~100 nm to ~150 μm in diameter, more preferably ~200 nm to ~30 μm in diameter, and most preferably ~500 nm to ~10 μm in diameter) formed from materials that are biodegradable and non-toxic (e.g. a poly(a-hydroxy acid), a polyhydroxybutyric acid, a polyorthoester, a polyanhydride, a polycaprolactone, etc.), with poly(lactide-co-glycolide) are preferred, optionally treated to have a negatively-charged surface (e.g. with SDS) or a positively-charged surface (e.g. with a cationic detergent, such as CTAB).

I. Liposomes (Chapters 13 & 14 of Ref. 22)

Examples of liposome formulations suitable for use as adjuvants are described in refs. 75-77.

J. Polyoxyethylene Ether and Polyoxyethylene Ester Formulations

Adjuvants suitable for use in the invention include polyoxyethylene ethers and polyoxyethylene esters [78]. Such formulations further include polyoxyethylene sorbitan ester surfactants in combination with an octoxynol [79] as well as polyoxyethylene alkyl ethers or ester surfactants in combination with at least one additional non-ionic surfactant such as an octoxynol [80]. Preferred polyoxyethylene ethers are selected from the following group: polyoxyethylene-9-lauryl ether (laureth 9), polyoxyethylene-9-steoryl ether, polyoxytheylene-8-steoryl ether, polyoxyethylene-4-lauryl ether, polyoxyethylene-35-lauryl ether, and polyoxyethylene-23-lauryl ether.

K. Polyphosphazene (PCPP)

PCPP formulations are described, for example, in refs. 81 and 82.

L. Muramyl Peptides

Examples of muramyl peptides suitable for use as adjuvants in the invention include N-acetyl-muramyl-L-threonyl-D-isoglutamine (thr-MDP), N-acetyl-normuramyl-L-alanyl-D-isoglutamine (nor-MDP), and N-acetylmuramyl-L-alanyl-D-isoglutaminyl-L-alanine-2-(1'-2'-dipalmitoyl-sn-glycero-3-hydroxyphosphoryloxy)-ethylamine MTP-PE).

M. Imidazoquinoline Compounds.

Examples of imidazoquinoline compounds suitable for use adjuvants in the invention include Imiquamod and its homologues (e,g. "Resiquimod 3M"), described further in refs. 83 and 84.

The invention may also comprise combinations of aspects of one or more of the adjuvants identified above. For example, the following adjuvant compositions may be used in the invention: (1) a saponin and an oil-in-water emulsion [85]; (2) a saponin (e.g. QS21)+a non-toxic LPS derivative (e.g. 3dMPL) [86]; (3) a saponin (e.g. QS21)+a non-toxic LPS derivative (e.g. 3dMPL)+a cholesterol; (4) a saponin (e.g. QS21)+3dMPL+IL-12 (optionally+a sterol) [87]; (5) combinations of 3dMPL with, for example, QS21 and/or oil-in-water emulsions [88]; (6) SAF, containing 10% squalane, 0.4% Tween 80™, 5% pluronic-block polymer L121, and thr-MDP, either microfluidized into a submicron emulsion or vortexed to generate a larger particle size emulsion. (7) Ribi™ adjuvant system (RAS), (Ribi Immunochem) containing 2% squalene, 0.2% Tween 80, and one or more bacterial cell wall components from the group consisting of monophosphorylipid A (MPL), trehalose dimycolate (TDM), and cell wall skeleton (CWS), preferably MPL+CWS (Detox™); and (8) one or more mineral salts (such as an aluminum salt)+a non-toxic derivative of LPS (such as 3dMPL).

Other substances that act as immunostimulating agents are disclosed in chapter 7 of ref. 22.

Aluminium salts (aluminium phosphates and particularly hydroxyphosphates, and/or hydroxides and particularly oxyhydroxide) and MF59 are preferred adjuvants for parenteral immunisation. Toxin mutants are preferred mucosal adjuvants. QS21 is another useful adjuvant for NMB1870, which may be used alone or in combination with one or more other adjuvants e.g. with an aluminium salt.

Muramyl peptides include N-acetyl-muramyl-L-threonyl-D-isoglutamine (thr-MDP), N-acetyl-normuramyl-L-alanyl-D-isoglutamine (nor-MDP), N-acetylmuramyl-L-alanyl-D-isoglutaminyl-L-alanine-2-(1'-2'-dipalmitoyl-sn-glycero-3-hydroxyphosphoryloxy)-ethylamine MTP-PE), etc.

Further Antigenic Components

Compositions of the invention include NMB1870 sequences. It is particularly preferred that the composition should not include complex or undefined mixtures of antigens e.g. it is preferred not to include outer membrane vesicles in the composition. Polypeptides of the invention are preferably expressed recombinantly in a heterologous host and then purified.

As well as including a NMB1870 sequence, a composition of the invention may also include one or more further neisserial antigen(s), as a vaccine which targets more than one antigen per bacterium decreases the possibility of selecting escape mutants. Neisserial antigens for inclusion in the compositions include polypeptides comprising one or more of:

(a) the 446 even SEQ IDs (i.e. 2, 4, 6, . . . , 890, 892) disclosed in reference 89.
(b) the 45 even SEQ IDs (i.e. 2, 4, 6, . . . , 88, 90) disclosed in reference 90;
(c) the 1674 even SEQ IDs 2-3020, even SEQ IDs 3040-3114, and all SEQ IDs 3115-3241, disclosed in reference 3;
(d) the 2160 amino acid sequences NMB0001 to NMB2160 from reference 2;
(e) a meningococcal PorA protein, of any subtype, preferably recombinantly expressed;
(f) a variant, homolog, ortholog, paralog, mutant etc. of (a) to (e); or
(g) an outer membrane vesicle preparation from *N. meningitidis* [e.g. see ref. 182].

In addition to Neisserial polypeptide antigens, the composition may include antigens for immunising against other diseases or infections. For example, the composition may include one or more of the following further antigens:

- a saccharide antigen from *N. meningitidis* serogroup A, C, W135 and/or Y, such as the oligosaccharide disclosed in ref. 91 from serogroup C [see also ref. 92] or the oligosaccharides of ref. 93.
- a saccharide antigen from *Streptococcus pneumoniae* [e.g. 94, 95, 96].

- an antigen from hepatitis A virus, such as inactivated virus [e.g. 97, 98].
- an antigen from hepatitis B virus, such as the surface and/or core antigens [e.g. 98, 99].
- a diphtheria antigen, such as a diphtheria toxoid [e.g. chapter 3 of ref. 100] e.g. the $CRM_{197}$ mutant [e.g. 101].
- a tetanus antigen, such as a tetanus toxoid [e.g. chapter 4 of ref. 100].
- an antigen from *Bordetella pertussis*, such as pertussis holotoxin (PT) and filamentous haemagglutinin (FHA) from *B. pertussis*, optionally also in combination with pertactin and/or agglutinogens 2 and 3 [e.g. refs. 102 & 103].
- a saccharide antigen from Haemophilus influenzae B [e.g. 92].
- polio antigen(s) [e.g. 104, 105] such as IPV.
- measles, mumps and/or rubella antigens [e.g. chapters 9, 10 & 11 of ref. 100].
- influenza antigen(s) [e.g. chapter 19 of ref 100], such as the haemagglutinin and/or neuraminidase surface proteins.
- an antigen from *Moraxella catarrhalis* [e.g. 106].
- an protein antigen from *Streptococcus agalactiae* (group B *streptococcus*) [e.g. 107, 108].
- a saccharide antigen from *Streptococcus agalactiae* (group B *streptococcus*).
- an antigen from *Streptococcus pyogenes* (group A *streptococcus)*[e.g. 108, 109, 110].
- an antigen from *Staphylococcus aureus* [e.g. 111].

The composition may comprise one or more of these further antigens.

Toxic protein antigens may be detoxified where necessary (e.g. detoxification of pertussis toxin by chemical and/or genetic means [103]).

Where a diphtheria antigen is included in the composition it is preferred also to include tetanus antigen and pertussis antigens. Similarly, where a tetanus antigen is included it is preferred also to include diphtheria and pertussis antigens. Similarly, where a pertussis antigen is included it is preferred also to include diphtheria and tetanus antigens. DTP combinations are thus preferred.

Saccharide antigens are preferably in the form of conjugates. Carrier proteins for the conjugates are discussed in more detail below.

Antigens in the composition will typically be present at a concentration of at least 1 g/ml each. In general, the concentration of any given antigen will be sufficient to elicit an immune response against that antigen.

Immunogenic compositions of the invention may be used therapeutically (i.e. to treat an existing infection) or prophylactically (i.e. to prevent future infection).

As an alternative to using proteins antigens in the immunogenic compositions of the invention, nucleic acid (preferably DNA e.g. in the form of a plasmid) encoding the antigen may be used.

Particularly preferred compositions of the invention include one, two or three of: (a) saccharide antigens from meningococcus serogroups Y, W135, C and (optionally) A; (b) a saccharide antigen from *Haemophilus influenzae* type B; and/or (c) an antigen from *Streptococcus pneumoniae.*

Meningococcus Serogroups Y, W135, C and (Optionally) A

Polysaccharide vaccines against serogroups A, C, W135 & Y have been known for many years. These vaccines (MENCEVAX ACWY™ and MENOMUNE™) are based on the organisms' capsular polysaccharides and, although they are effective in adolescents and adults, they give a poor immune response and short duration of protection, and they cannot be used in infants.

In contrast to the unconjugated polysaccharide antigens in these vaccines, the recently-approved serogroup C vaccines (Menjugate™ [112,91], Meningitec™ and NeisVac-C™) include conjugated saccharides. Menjugate™ and Meningitec™ have oligosaccharide antigens conjugated to a $CRM_{197}$ carrier, whereas NeisVac-C™ uses the complete polysaccharide (de-O-acetylated) conjugated to a tetanus toxoid carrier. The Menactra™ vaccine contains conjugated capsular saccharide antigens from each of serogroups Y, W135, C and A.

Compositions of the present invention preferably include capsular saccharide antigens from one or more of meningococcus serogroups Y, W135, C and (optionally) A, wherein the antigens are conjugated to carrier protein(s) and/or are oligosaccharides. For example, the composition may include a capsular saccharide antigen from: serogroup C; serogroups A and C; serogroups A, C and W135; serogroups A, C and Y; serogroups C, W135 and Y; or from all four of serogroups A, C, W135 and Y.

A typical quantity of each meningococcal saccharide antigen per dose is between 1 μg and 20 μg e.g. about 1 μg, about 2.5 μg, about 4 μg, about 5 μg, or about 10 μg (expressed as saccharide).

Where a mixture comprises capsular saccharides from both serogroups A and C, the ratio (w/w) of MenA saccharide: MenC saccharide may be greater than 1 (e.g. 2:1, 3:1, 4:1, 5:1, 10:1 or higher).

Where a mixture comprises capsular saccharides from serogroup Y and one or both of serogroups C and W135, the ratio (w/w) of MenY saccharide:MenW135 saccharide may be greater than 1 (e.g. 2:1, 3:1, 4:1, 5:1, 10:1 or higher) and/or that the ratio (w/w) of MenY saccharide:MenC saccharide may be less than 1 (e.g. 1:2, 1:3, 1:4, 1:5, or lower). Preferred ratios (w/w) for saccharides from serogroups A:C:W135:Y are: 1:1:1:1; 1:1:1:2; 2:1:1:1; 4:2:1:1; 8:4:2:1; 4:2:1:2; 8:4:1:2; 4:2:2:1; 2:2:1:1; 4:4:2:1; 2:2:1:2; 4:4:1:2; and 2:2:2:1. Preferred ratios (w/w) for saccharides from serogroups C:W135:Y are: 1:1:1; 1:1:2; 1:1:1; 2:1:1; 4:2:1; 2:1:2; 4:1:2; 2:2:1; and 2:1:1. Using a substantially equal mass of each saccharide is preferred.

Capsular saccharides will generally be used in the form of oligosaccharides. These are conveniently formed by fragmentation of purified capsular polysaccharide (e.g. by hydrolysis), which will usually be followed by purification of the fragments of the desired size.

Fragmentation of polysaccharides is preferably performed to give a final average degree of polymerisation (DP) in the oligosaccharide of less than 30 (e.g. between 10 and 20, preferably around 10 for serogroup A; between 15 and 25 for serogroups W135 and Y, preferably around 15-20; between 12 and 22 for serogroup C; etc.). DP can conveniently be measured by ion exchange chromatography or by colorimetric assays [113].

If hydrolysis is performed, the hydrolysate will generally be sized in order to remove short-length oligosaccharides [92]. This can be achieved in various ways, such as ultrafiltration followed by ion-exchange chromatography. Oligosaccharides with a degree of polymerisation of less than or equal to about 6 are preferably removed for serogroup A, and those less than around 4 are preferably removed for serogroups W135 and Y.

Preferred MenC saccharide antigens are disclosed in reference 112, as used in Menjugate™.

The saccharide antigen may be chemically modified. This is particularly useful for reducing hydrolysis for serogroup A

[114; see below]. De-O-acetylation of meningococcal saccharides can be performed. For oligosaccharides, modification may take place before or after depolymerisation.

Where a composition of the invention includes a MenA saccharide antigen, the antigen is preferably a modified saccharide in which one or more of the hydroxyl groups on the native saccharide has/have been replaced by a blocking group [114]. This modification improves resistance to hydrolysis.

Meningococcal capsular polysaccharides are typically prepared by a process comprising the steps of polysaccharide precipitation (e.g. using a cationic detergent), ethanol fractionation, cold phenol extraction (to remove protein) and ultracentrifugation (to remove LPS) [e.g. ref. 115]. A more preferred process [93], however, involves polysaccharide precipitation followed by solubilisation of the precipitated polysaccharide using a lower alcohol. Precipitation can be achieved using a cationic detergent such as tetrabutylammonium and cetyltrimethylammonium salts (e.g. the bromide salts), or hexadimethrine bromide and myristyltrimethylammonium salts. Cetyltrimethylammonium bromide ('CTAB') is particularly preferred [116]. Solubilisation of the precipitated material can be achieved using a lower alcohol such as methanol, propan-1-ol, propan-2-ol, butan-1-ol, butan-2-ol, 2-methyl-propan-1-ol, 2-methyl-propan-2-ol, diols, etc., but ethanol is particularly suitable for solubilising CTAB-polysaccharide complexes. Ethanol is preferably added to the precipitated polysaccharide to give a final concentration (based on total content of ethanol and water) of between 50% and 95%.

After re-solubilisation, the polysaccharide may be further treated to remove contaminants. This is particularly important in situations where even minor contamination is not acceptable (e.g. for human vaccine production). This will typically involve one or more steps of filtration e.g. depth filtration, filtration through activated carbon may be used, size filtration and/or ultrafiltration. Once filtered to remove contaminants, the polysaccharide may be precipitated for further treatment and/or processing. This can be conveniently achieved by exchanging cations (e.g. by the addition of calcium or sodium salts).

As an alternative to purification, capsular saccharides may be obtained by total or partial synthesis e.g. Hib synthesis is disclosed in ref. 117, and MenA synthesis in ref. 118.

Compositions of the invention comprise capsular saccharides from at least two serogroups of *N. meningitidis*. The saccharides are preferably prepared separately (including any fragmentation, conjugation, modification, etc.) and then admixed to give a composition of the invention.

Where the composition comprises capsular saccharide from serogroup A, however, it is preferred that the serogroup A saccharide is not combined with the other saccharide(s) until shortly before use, in order to minimise the potential for hydrolysis. This can conveniently be achieved by having the serogroup A component (typically together with appropriate excipients) in lyophilised form and the other serogroup component(s) in liquid form (also with appropriate excipients), with the liquid components being used to reconstitute the lyophilised MenA component when ready for use. Where an aluminium salt adjuvant is used, it is preferred to include the adjuvant in the vial containing the with the liquid vaccine, and to lyophilise the MenA component without adjuvant.

A composition of the invention may thus be prepared from a kit comprising: (a) capsular saccharide from *N. meningitidis* serogroup A, in lyophilised form; and (b) the further antigens from the composition, in liquid form. The invention also provides a method for preparing a composition of the invention, comprising mixing a lyophilised capsular saccharide from *N. meningitidis* serogroup A with the further antigens, wherein said further antigens are in liquid form.

The invention also provides a kit comprising: (a) a first container containing capsular saccharides from two or more of *N. meningitidis* serogroups C, W135 and Y, all in lyophilised form; and (b) a second container containing in liquid form (i) a composition which, after administration to a subject, is able to induce an antibody response in that subject, wherein the antibody response is bactericidal against two or more (e.g. 2 or 3) of hypervirulent lineages A4, ET-5 and lineage 3 of *N. meningitidis* serogroup B, (ii) capsular saccharides from none or one of *N. meningitidis* serogroups C, W135 and Y, and optionally (iii) further antigens (see below) that do not include meningococcal capsular saccharides, wherein, reconstitution of the contents of container (a) by the contents of container (b) provides a composition of the invention.

Within each dose, the amount of an individual saccharide antigen will generally be between 1-50 μg (measured as mass of saccharide), with about 2.5 μg, 5 μg or 10 μg of each being preferred. With A:C:W135:Y weight ratios of 1:1:1:1; 1:1:1:2; 2:1:1:1; 4:2:1:1; 8:4:2:1; 4:2:1:2; 8:4:1:2; 4:2:2:1; 2:2:1:1; 4:4:2:1; 2:2:1:2; 4:4:1:2; and 2:2:2:1, therefore, the amount represented by the number 1 is preferably about 2.5 μg, 5 μg or 10 μg. For a 1:1:1:1 ratio A:C:W:Y composition and a 10 μg per saccharide, therefore, 40 μg saccharide is administered per dose. Preferred compositions have about the following μg saccharide per dose:

| | | | | | | | |
|---|---|---|---|---|---|---|---|
| A | 10 | 0 | 0 | 0 | 10 | 5 | 2.5 |
| C | 10 | 10 | 5 | 2.5 | 5 | 5 | 2.5 |
| W135 | 10 | 10 | 5 | 2.5 | 5 | 5 | 2.5 |
| Y | 10 | 10 | 5 | 2.5 | 5 | 5 | 2.5 |

Preferred compositions of the invention comprise less than 50 μg meningococcal saccharide per dose. Other preferred compositions comprise ≦40 μg meningococcal saccharide per dose. Other preferred compositions comprise ≦30 μg meningococcal saccharide per dose. Other preferred compositions comprise ≦25 μg meningococcal saccharide per dose. Other preferred compositions comprise ≦20 μg meningococcal saccharide per dose. Other preferred compositions comprise ≦10 μg meningococcal saccharide per dose but, ideally, compositions of the invention comprise at least 10 μg meningococcal saccharide per dose.

The Menjugate™ and NeisVac™ MenC conjugates use a hydroxide adjuvant, whereas Meningitec™ uses a phosphate. It is possible in compositions of the invention to adsorb some antigens to an aluminium hydroxide but to have other antigens in association with an aluminium phosphate. For tetravalent serogroup combinations, for example, the following permutations are available:

| Serogroup | Aluminium salt (H = a hydroxide; P = a phosphate) | | | | | | | | | | | | | | |
|---|---|---|---|---|---|---|---|---|---|---|---|---|---|---|---|
| A | P | H | P | H | H | H | P | P | P | H | H | H | P | P | H |
| C | P | H | H | P | H | H | P | H | H | P | P | H | P | H | P |

-continued

| Serogroup | Aluminium salt (H = a hydroxide; P = a phosphate) | | | | | | | | | | | | | | | |
|---|---|---|---|---|---|---|---|---|---|---|---|---|---|---|---|---|
| W135 | P | H | H | H | P | H | H | P | H | H | P | P | P | P | H | P |
| Y | P | H | H | H | H | P | H | H | P | P | H | P | H | P | P | P |

For trivalent *N. meningitidis* serogroup combinations, the following permutations are available:

| Serogroup | Aluminium salt (H = a hydroxide; P = a phosphate) | | | | | | | |
|---|---|---|---|---|---|---|---|---|
| C | P | H | H | H | P | P | P | H |
| W135 | P | H | H | P | H | P | H | P |
| Y | P | H | P | H | H | H | P | P |

*Haemophilus influenzae* Type B

Where the composition includes a *H. influenzae* type b antigen, it will typically be a Hib capsular saccharide antigen. Saccharide antigens from *H. influenzae* b are well known.

Advantageously, the Hib saccharide is covalently conjugated to a carrier protein, in order to enhance its immunogenicity, especially in children. The preparation of polysaccharide conjugates in general, and of the Hib capsular polysaccharide in particular, is well documented [e.g. references 119 to 127 etc.]. The invention may use any suitable Hib conjugate. Suitable carrier proteins are described below, and preferred carriers for Hib saccharides are $CRM_{197}$ ('HbOC'), tetanus toxoid ('PRP-T') and the outer membrane complex of *N. meningitidis* ('PRP-OMP').

The saccharide moiety of the conjugate may be a polysaccharide (e.g. full-length polyribosylribitol phosphate (PRP)), but it is preferred to hydrolyse polysaccharides to form oligosaccharides (e.g. MW from ~1 to ~5 kDa).

A preferred conjugate comprises a Hib oligosaccharide covalently linked to $CRM_{197}$ via an adipic acid linker [128, 129]. Tetanus toxoid is also a preferred carrier.

Compositions of the invention may comprise more than one Hib antigen.

Where a composition includes a Hib saccharide antigen, it is preferred that it does not also include an aluminium hydroxide adjuvant. If the composition includes an aluminium phosphate adjuvant then the Hib antigen may be adsorbed to the adjuvant [130] or it may be non-adsorbed [131].

Hib antigens may be lyophilised e.g. together with meningococcal antigens.

*Streptococcus pneumoniae*

Where the composition includes a *S. pneumoniae* antigen, it will typically be a capsular saccharide antigen which is preferably conjugated to a carrier protein [e.g. refs. 94-96]. It is preferred to include saccharides from more than one serotype of *S. pneumoniae*. For example, mixtures of polysaccharides from 23 different serotype are widely used, as are conjugate vaccines with polysaccharides from between 5 and 11 different serotypes [132]. For example, PrevNar™ [133] contains antigens from seven serotypes (4, 6B, 9V, 14, 18C, 19F, and 23F) with each saccharide individually conjugated to $CRM_{197}$ by reductive amination, with 2 μg of each saccharide per 0.5 ml dose (4 μg of serotype 6B), and with conjugates adsorbed on an aluminium phosphate adjuvant. Compositions of the invention preferably include at least serotypes 6B, 14, 19F and 23F. Conjugates may be adsorbed onto an aluminium phosphate.

As an alternative to using saccharide antigens from pneumococcus, the composition may include one or more polypeptide antigens. Genome sequences for several strains of pneumococcus are available [134,135] and can be subjected to reverse vaccinology [136-139] to identify suitable polypeptide antigens [140,141]. For example, the composition may include one or more of the following antigens: PhtA, PhtD, PhtB, PhtE, SpsA, LytB, LytC, LytA, Sp125, Sp101, Sp128 and Sp130, as defined in reference 142.

In some embodiments, the composition may include both saccharide and polypeptide antigens from pneumococcus. These may be used in simple admixture, or the pneumococcal saccharide antigen may be conjugated to a pneumococcal protein. Suitable carrier proteins for such embodiments include the antigens listed in the previous paragraph [142].

Pneumococcal antigens may be lyophilised e.g. together with meningococcal and/or Hib antigens.

Covalent Conjugation

Capsular saccharides in compositions of the invention will usually be conjugated to carrier protein(s). In general, conjugation enhances the immunogenicity of saccharides as it converts them from T-independent antigens to T-dependent antigens, thus allowing priming for immunological memory. Conjugation is particularly useful for paediatric vaccines and is a well known technique [e.g. reviewed in refs. 143 and 119-127].

Preferred carrier proteins are bacterial toxins or toxoids, such as diphtheria toxoid or tetanus toxoid. The $CRM_{197}$ mutant diphtheria toxin [144,145,146] is particularly preferred. Other suitable carrier proteins include the *N. meningitidis* outer membrane protein [147], synthetic peptides [148,149], heat shock proteins [150,151], pertussis proteins [152,153], protein D from *H. influenzae* [154,155], cytokines [156], lymphokines [156], artificial proteins comprising multiple human CD4+ T cell epitopes from various pathogen-derived antigens [157], streptococcal proteins, hormones [156], growth factors [156], pneumococcal surface protein PspA [158], toxin A or B from *C. difficile* [159], iron-uptake proteins [160], etc. A preferred carrier protein is CRM 197.

Within a composition of the invention, it is possible to use more than one carrier protein e.g. to reduce the risk of carrier suppression. Thus different carrier proteins can be used for different serogroups e.g. serogroup A saccharides might be conjugated to $CRM_{197}$ while serogroup C saccharides might be conjugated to tetanus toxoid. It is also possible to use more than one carrier protein for a particular saccharide antigen e.g. serogroup A saccharides might be in two groups, with some conjugated to $CRM_{197}$ and others conjugated to tetanus toxoid. In general, however, it is preferred to use the same carrier protein for all saccharides.

A single carrier protein might carry more than one saccharide antigen [161]. For example, a single carrier protein might have conjugated to it saccharides from serogroups A and C. To achieve this goal, saccharides can be mixed prior to the conjugation reaction. In general, however, it is preferred to have separate conjugates for each serogroup.

Conjugates with a saccharide:protein ratio (w/w) of between 1:5 (i.e. excess protein) and 5:1 (i.e. excess saccharide) are preferred. Ratios between 1:2 and 5:1 are preferred, as are ratios between 1:1.25 and 1:2.5 are more preferred. Excess carrier protein is preferred for MenA and MenC.

Conjugates may be used in conjunction with free carrier protein [162]. When a given carrier protein is present in both free and conjugated form in a composition of the invention, the unconjugated form is preferably no more than 5% of the total amount of the carrier protein in the composition as a whole, and more preferably present at less than 2% by weight.

Any suitable conjugation reaction can be used, with any suitable linker where necessary.

The saccharide will typically be activated or functionalised prior to conjugation. Activation may involve, for example, cyanylating reagents such as CDAP (e.g. 1-cyano-4-dimethylamino pyridinium tetrafluoroborate [163,164,etc.]). Other suitable techniques use carbodiimides, hydrazides, active esters, norborane, p-nitrobenzoic acid, N-hydroxysuccinimide, S-NHS, EDC, TSTU; see also the introduction to reference 125).

Linkages via a linker group may be made using any known procedure, for example, the procedures described in references 165 and 166. One type of linkage involves reductive amination of the polysaccharide, coupling the resulting amino group with one end of an adipic acid linker group, and then coupling a protein to the other end of the adipic acid linker group [123,167,168]. Other linkers include B-propionamido [169], nitrophenyl-ethylamine [170], haloacyl halides [171], glycosidic linkages [172], 6-aminocaproic acid [173], ADH [174], $C_4$ to $C_{12}$ moieties [175] etc. As an oxidation of the polysaccharide followed by reductive amination with the protein, as described in, for example, references 176 and 177.

A process involving the introduction of amino groups into the saccharide (e.g. by replacing terminal =O groups with $-NH_2$) followed by derivatisation with an adipic diester (e.g. adipic acid N-hydroxysuccinimido diester) and reaction with carrier protein is preferred. Another preferred reaction uses CDAP activation with a protein D carrier e.g. for MenA or MenC.

After conjugation, free and conjugated saccharides can be separated. There are many suitable methods, including hydrophobic chromatography, tangential ultrafiltration, diafiltration etc. [see also refs. 178 & 179, etc.].

Where the composition of the invention includes a conjugated oligosaccharide, it is preferred that oligosaccharide preparation precedes conjugation.

Outer Membrane Vesicles It is preferred that compositions of the invention should not include complex or undefined mixtures of antigens, which are typical characteristics of OMVs. However, the invention can be used in conjunction with OMVs, as NMB1870 has been found to enhance their efficacy [6], in particular by over-expressing the polypeptides of the invention in the strains used for OMV preparation.

This approach may be used in general to improve preparations of *N. meningitidis* serogroup B microvesicles [180], 'native OMVs' [181], blebs or outer membrane vesicles [e.g. refs. 182 to 187, etc.]. These may be prepared from bacteria which have been genetically manipulated [188-191] e.g. to increase immunogenicity (e.g. hyper-express immunogens), to reduce toxicity, to inhibit capsular polysaccharide synthesis, to down-regulate PorA expression, etc. They may be prepared from hyperblebbing strains [192-195]. Vesicles from a non-pathogenic *Neisseria* may be included [196]. OMVs may be prepared without the use of detergents [197, 198]. They may express non-Neisserial proteins on their surface [199]. They may be LPS-depleted. They may be mixed with recombinant antigens [182,200]. Vesicles from bacteria with different class I outer membrane protein subtype may be used e.g. six different subtypes [201,202] using two different genetically-engineered vesicle populations each displaying three subtypes, or nine different subtypes using three different genetically-engineered vesicle populations each displaying three subtypes, etc. Useful subtypes include: P1.7,16; P1.5-1,2-2; P1.19,15-1; P1.5-2,10; P1.12-1,13; P1.7-2,4; P1.22,14; P1.7-1,1; P1.18-1,3,6.

Protein Expression

Bacterial expression techniques are known in the art. A bacterial promoter is any DNA sequence capable of binding bacterial RNA polymerase and initiating the downstream (3') transcription of a coding sequence (e.g. structural gene) into mRNA. A promoter will have a transcription initiation region which is usually placed proximal to the 5' end of the coding sequence. This transcription initiation region usually includes an RNA polymerase binding site and a transcription initiation site. A bacterial promoter may also have a second domain called an operator, that may overlap an adjacent RNA polymerase binding site at which RNA synthesis begins. The operator permits negative regulated (inducible) transcription, as a gene repressor protein may bind the operator and thereby inhibit transcription of a specific gene. Constitutive expression may occur in the absence of negative regulatory elements, such as the operator. In addition, positive regulation may be achieved by a gene activator protein binding sequence, which, if present is usually proximal (5') to the RNA polymerase binding sequence. An example of a gene activator protein is the catabolite activator protein (CAP), which helps initiate transcription of the lac operon in *Escherichia coli* (*E. coli*) [Raibaud et al. (1984) *Annu. Rev. Genet* 18:173]. Regulated expression may therefore be either positive or negative, thereby either enhancing or reducing transcription.

Sequences encoding metabolic pathway enzymes provide particularly useful promoter sequences.

Examples include promoter sequences derived from sugar metabolizing enzymes, such as galactose, lactose (lac) [Chang et al. (1977) *Nature* 198:1056], and maltose. Additional examples include promoter sequences derived from biosynthetic enzymes such as tryptophan (trp) [Goeddel et al. (1980) *Nuc. Acids Res.* 8:4057; Yelverton et al. (1981) *Nucl. Acids Res.* 9:731; U.S. Pat. No. 4,738,921; EP-A-0036776 and EP-A-0121775]. The β-lactamase (blα) promoter system [Weissmann (1981) "The cloning of interferon and other mistakes." In *Interferon* 3 (ed. I. Gresser)], bacteriophage lambda PL [Shimatake et al. (1981) *Nature* 292:128] and T5 [U.S. Pat. No., 4,689,406] promoter systems also provide useful promoter sequences. Another promoter of interest is an inducible arabinose promoter (pBAD).

In addition, synthetic promoters which do not occur in nature also function as bacterial promoters.

For example, transcription activation sequences of one bacterial or bacteriophage promoter may be joined with the operon sequences of another bacterial or bacteriophage promoter, creating a synthetic hybrid promoter [U.S. Pat. No. 4,551,433]. For example, the tac promoter is a hybrid trp-lac promoter comprised of both trp promoter and lac operon sequences that is regulated by the lac repressor [Amann et al. (1983) *Gene* 25:167; de Boer et al. (1983) *Proc. Natl. Acad. Sci.* 80:21]. Furthermore, a bacterial promoter can include naturally occurring promoters of non-bacterial origin that have the ability to bind bacterial RNA polymerase and initiate transcription. A naturally occurring promoter of non-bacterial origin can also be coupled with a compatible RNA polymerase to produce high levels of expression of some genes in prokaryotes. The bacteriophage T7 RNA polymerase/promoter system is an example of a coupled promoter system [Studier et al. (1986) *J. Mol. Biol.* 189:113; Tabor et al. (1985) *Proc Natl. Acad. Sci.* 82:1074]. In addition, a hybrid promoter can also be comprised of a bacteriophage promoter and an *E. coli* operator region (EPO-A-0 267 851).

In addition to a functioning promoter sequence, an efficient ribosome binding site is also useful for the expression of foreign genes in prokaryotes. In *E. coli*, the ribosome binding site is called the Shine-Dalgarno (SD) sequence and includes an initiation codon (ATG) and a sequence 3-9 nucleotides in length located 3-11 nucleotides upstream of the initiation codon. The SD sequence is thought to promote binding of mRNA to the ribosome by the pairing of bases between the SD sequence and the 3' and of *E. coli* 16S rRNA [Steitz et al. (1979) "Genetic signals and nucleotide sequences in messenger RNA." In *Biological Regulation and Development: Gene Expression* (ed. R. F. Goldberger)]. To express eukaryotic genes and prokaryotic genes with weak ribosome-binding site [Sambrook et al. (1989) "Expression of cloned genes in *Escherichia coli*." In *Molecular Cloning: A Laboratory Manual]*.

A promoter sequence may be directly linked with the DNA molecule, in which case the first amino acid at the N-terminus will always be a methionine, which is encoded by the ATG start codon. If desired, methionine at the N-terminus may be cleaved from the protein by in vitro incubation with cyanogen bromide or by either in vivo on in vitro incubation with a bacterial methionine N-terminal peptidase (EP-A-0219237).

Usually, transcription termination sequences recognized by bacteria are regulatory regions located 3' to the translation stop codon, and thus together with the promoter flank the coding sequence. These sequences direct the transcription of an mRNA which can be translated into the polypeptide encoded by the DNA. Transcription termination sequences frequently include DNA sequences of about 50 nucleotides capable of forming stem loop structures that aid in terminating transcription. Examples include transcription termination sequences derived from genes with strong promoters, such as the trp gene in *E. coli* as well as other biosynthetic genes.

Usually, the above described components, comprising a promoter, signal sequence (if desired), coding sequence of interest, and transcription termination sequence, are put together into expression constructs. Expression constructs are often maintained in a replicon, such as an extrachromosomal element (e.g. plasmids) capable of stable maintenance in a host, such as bacteria. The replicon will have a replication system, thus allowing it to be maintained in a prokaryotic host either for expression or for cloning and amplification. In addition, a replicon may be either a high or low copy number plasmid. A high copy number plasmid will generally have a copy number ranging from about 5 to about 200, and usually about 10 to about 150. A host containing a high copy number plasmid will preferably contain at least about 10, and more preferably at least about 20 plasmids. Either a high or low copy number vector may be selected, depending upon the effect of the vector and the foreign protein on the host.

Alternatively, the expression constructs can be integrated into the bacterial genome with an integrating vector. Integrating vectors usually contain at least one sequence homologous to the bacterial chromosome that allows the vector to integrate. Integrations appear to result from recombinations between homologous DNA in the vector and the bacterial chromosome. For example, integrating vectors constructed with DNA from various *Bacillus* strains integrate into the *Bacillus* chromosome (EP-A-0127328). Integrating vectors may also be comprised of bacteriophage or transposon sequences.

Usually, extrachromosomal and integrating expression constructs may contain selectable markers to allow for the selection of bacterial strains that have been transformed. Selectable markers can be expressed in the bacterial host and may include genes which render bacteria resistant to drugs such as ampicillin, chloramphenicol, erythromycin, kanamycin (neomycin), and tetracycline [Davies et al. (1978) *Annu. Rev. Microbiol.* 32:469]. Selectable markers may also include biosynthetic genes, such as those in the histidine, tryptophan, and leucine biosynthetic pathways.

Alternatively, some of the above described components can be put together in transformation vectors. Transformation vectors are usually comprised of a selectable market that is either maintained in a replicon or developed into an integrating vector, as described above.

Expression and transformation vectors, either extra-chromosomal replicons or integrating vectors, have been developed for transformation into many bacteria. For example, expression vectors have been developed for, inter alia, the following bacteria: *Bacillus subtilis* [Palva et al. (1982) *Proc. Natl. Acad. Sci. USA* 79:5582; EP-A-0 036 259 and EP-A-0 063 953; WO 84/04541], *Escherichia coli* [Shimatake et al. (1981) *Nature* 292:128; Amann et al. (1985) *Gene* 40:183; Studier et al. (1986) *J. Mol. Biol.* 189:113; EP-A-0 036 776, EP-A-0 136 829 and EP-A-0 136 907], *Streptococcus cremoris* [Powell et al. (1988) *Appl. Environ. Microbiol.* 54:655]; *Streptococcus lividans* [Powell et al. (1988) *Appl. Environ. Microbiol.* 54:655], *Streptomyces lividans* [U.S. Pat. No, 4,745,056].

Methods of introducing exogenous DNA into bacterial hosts are well-known in the art, and usually include either the transformation of bacteria treated with $CaCl_2$ or other agents, such as divalent cations and DMSO. DNA can also be introduced into bacterial cells by electroporation. Transformation procedures usually vary with the bacterial species to be transformed. See e.g. [Masson et al. (1989) *FEMS Microbiol. Lett.* 60:273; Palva et al. (1982) *Proc. Natl. Acad Sci. USA* 79:5582; EP-A-0 036 259 and EP-A-0 063 953; WO 84/04541, *Bacillus*], [Miller et al. (1988) *Proc. Natl. Acad. Sci.* 85:856; Wang et al. (1990) *J. Bacteriol.* 172:949, *Campylobacter*], [Cohen et al. (1973) *Proc. Natl. Acad Sci.* 69:2110; Dower et al. (1988) *Nucleic Acids Res.* 16:6127; Kushner (1978) "An improved method for transformation of *Escherichia coli* with ColE1-derived plasmids. In *Genetic Engineering: Proceedings of the International Symposium on Genetic Engineering* (eds. H. W. Boyer and S. Nicosia); Mandel et al. (1970) *J. Mol. Biol.* 53:159; Taketo (1988) *Biochim. Biophys. Acta* 949:318; *Escherichia*], [Chassy et al. (1987) *FEMS Microbiol. Lett.* 44:173 *Lactobacillus*]; [Fiedler et al. (1988) *Anal. Biochem* 170:38, Pseudomonas]; [Augustin et al. (1990) *FEMS Microbiol. Lett.* 66:203, *Staphylococcus*], [Barany et al. (1980) *J. Bacteriol.* 144:698; Harlander (1987) "Transformation of *Streptococcus lactis* by electroporation, in: *Streptococcal Genetics* (ed. J. Ferretti and R. Curtiss III); Perry et al. (1981) *Infect. Immun.* 32:1295; Powell et al. (1988) *Appl. Environ. Microbiol.* 54:655; Somkuti et al. (1987) *Proc. 4th Evr. Cong. Biotechnology* 1:412, *Streptococcus]*.

General

The term "comprising" encompasses "including" as well as "consisting" e.g. a composition "comprising" X may consist exclusively of X or may include something additional e.g. X+Y.

The term "about" in relation to a numerical value x means, for example, x±10%.

The word "substantially" does not exclude "completely" e.g. a composition which is "substantially free" from Y may be completely free from Y. Where necessary, the word "substantially" may be omitted from the definition of the invention.

"Sequence identity" is preferably determined by the Smith-Waterman homology search algorithm as implemented in the MPSRCH program (Oxford Molecular), using an affine gap search with parameters gap open penalty=12 and gap extension penalty=1.

After serogroup, meningococcal classification includes serotype, serosubtype and then immunotype, and the standard nomenclature lists serogroup, serotype, serosubtype, and immunotype, each separated by a colon e.g. B:4:P1.15:L3,7,9. Within serogroup B, some lineages cause disease often (hyperinvasive), some lineages cause more severe forms of disease than others (hypervirulent), and others rarely cause disease at all. Seven hypervirulent lineages are recognised, namely subgroups I, III and IV-1, ET-5 complex, ET-37 complex, A4 cluster and lineage 3. These have been defined by multilocus enzyme electrophoresis (MLEE), but multilocus sequence typing (MLST) has also been used to classify meningococci [ref. 18]. The four main hypervirulent clusters are ST32, ST44, ST8 and ST11 complexes.

In general, the invention does not encompass the various NMB1870 sequences specifically disclosed in references 4, 5, 7, 8, 9, 10, 11, 12, 13 and 203, although these NMB1870 sequences may be used according to the invention e.g. for the construction of chimeric sequences, etc.

MODES FOR CARRYING OUT THE INVENTION

Substitutions

SEQ ID NO: 59 is disclosed in reference 13 as a chimera of NMB1870 from families I, II & III. This polypeptide is derived by substitutions in seven regions of SEQ ID NO:1, identified below:

```
                                 {SEQ ID NO: 1)
MNRTAFCCLSLTTALILTACSSGGGGVAADIGAGLADALTAPLDHKDKG

LQSLTLDQSVRKNEKLKLAAQGAEKTYGNGDSLNTGKLKNDKVSRFDFI

RQIEVDGQLITLESGEFQVYKQSHSALTAFQTEQIQDSEHSGKMVAKRQ

FRIGDIAGEHTSFDKLPEGGRATYRGTAFGSDDAGGKLTYTIDFAAKQG

NGKIEHLKSPELNVDLAAADIKPDGKRHAVISGSVLYNQAEKGSYSLGI

FGGKAQEVAGSAEVKTVNGIRHIGLAAKQ
```

Although this chimera elicited antibodies that were bactericidal against meningococci from each NMB1870 family, responses against family H and family III strains were not consistently high.

By combining various approaches, including a NMR-derived 3D structure of the BC domain of a family I polypeptide, the inventors found that residues 162-168 (second underlined region) are surrounded by a patch of amino acids which are conserved between meningococcal MC58 (family I) and 2996 (family II). Thus the substitution created an extensive 2996-like area on the surface of the MC58 polypeptide, which could explain why chimeras including this substitution could elicit a bactericidal response against family II strains.

Substitution at the third underlined region (ProAsn instead of AlaGly) likely altered the local backbone conformation, introducing a high degree of rigidity which altered folding of the polypeptide and reduced bactericidal activity.

Based on a comparison of (i) sequence alignments within family II, and (ii) intra-family serum cross-reactivity, a number of amino acid residues were identified that could improve the ability of a chimera to elicit a good anti-II response. These residues are: (a) surface-exposed, based on the NMR structure, and so are immunoaccessible; (b) conserved within family II strains that were not killed by anti-2996 sera; and (c) not in the protein's hydrophobic pocket. Numbered according to SEQ ID NO:2, these residues were: D121; D165; A180; G181; K183; T185; T187; A191; A192; H196; K198; A213; S234; and G261. Except for D121 and D165, each of these residues was conserved in three strains which were resistant to antisera raised against the 2996 sequence. D121 is N in one of the three strains, and D165 is Sin two of the three strains.

Thus SEQ ID NO:57 was altered to give SEQ ID NO: 60, which was present as part of a full-length NMB1870 sequence.

The KLPEGGR 7-mer sequence (SEQ ID NO:61) in SEQ ID NO: 57 was replaced with the QLPDGK 6-mer (SEQ ID NO:62). Thus one amino acid is deleted. Depending on how these two sequences are aligned then the deleted residue can be identified as E51, G52, G53 or R54. The end result does not depend on which residue is nominally said to be deleted but, based on the alignment in reference 4, the deleted residue is best described as E51.

Tandem Polypeptides

As described in reference 12, a triple-tandem of all three NMB1870 families was prepared with the three families ordered I-III-II, from N-terminus to C-terminus. With or without a C-terminal histidine tag, this polypeptide elicited immune responses that were excellent against meningococci having a NMB1870 in families I and III (serum bactericidal titres ≧1:128 were typically seen against 100% of tested strains), but responses were weaker against strains in NMB1870 family II (≧1:128 titres typically seen against 60% of tested strains). In particular, responses were lower when using the tandem polypeptide than when using a mixture of the three separate proteins. In contrast, a II-III tandem gave good results, so the family II sequence is not inherently incompatible with the tandem expression approach.

Responses against families I and II are important, but family III strains are relatively rare. To improve efficacy against family II strains, three approaches have now been used: (a) the order of families was altered, to be I-II-III, II-III-I or II-I-III; (b) family III sequence was omitted, and families I and II were expressed either as I-II or as II-I; or (c) families I and II were expressed downstream of a 'protein 936 sequence', either as 936-I-II or as 936-II-I. These polypeptides were expressed with various linkers, leaders, etc., and with/without a C-terminal poly-His tag.

Embodiments of these three approaches are given as SEQ ID NOS: 27 to 38:

| SEQ ID | Description |
|---|---|
| 27 | II-I-$His_6$ |
| 28 | 936-I-II-$His_6$ |
| 29 | 936-II-I-$His_6$ |
| 30 | II-I-III-$His_6$ |
| 31 | II-III-I-$His_6$ |
| 32 | I-II-III-$His_6$ |
| 33 | II-I |
| 34 | 936-I-II |
| 35 | 936-II-I |
| 36 | II-III-I |
| 37 | II-I-III |
| 38 | I-II-III |

These proteins were used to immunise mice. Different adjuvants were tested, including Freund's complete adjuvant, an aluminium hydroxide adjuvant, MF59 oil-in-water emulsion, and a mixture of MF59 and an immunostimulatory oligonucleotide. Mice's sera were tested in bactericidal assays.

In general, SEQ ID NOs: 28 and 29 were equally effective. SEQ ID NO: 34 sometimes showed better activity than SEQ ID NO: 28. For the proteins including all three families, the best results were generally seen with SEQ ID NO: 37.

Family II Sequences 5 different strains in NMB1870 family II were selected: M3153, M00-0243143; 1000, NGH38 and M0579. The following primers were used to amplify fragments for inserting into the NdeI/XhoI sites of a pET *E. coli* expression vector. The sequences were amplified as ΔG sequences; in the "chimΔG" sequences, the primer added SEQ ID NO: 66 to the N-terminus. Forward primers provided a NdeI site; reverse primers provided a XhoI site.

| STRAIN | | SEQ ID NO: Fwd | Rev |
|---|---|---|---|
| M3153 | ΔG741 | 67 | 68 |
| | chimΔG741 | 69 | 70 |
| M00-0243143 | ΔG741 | 71 | 72 |
| | chimΔG741 | 73 | 74 |
| 1000 | ΔG741 | 75 | 76 |
| | chimΔG741 | 77 | 78 |
| NGH38 | ΔG741 | 79 | 80 |
| | chimΔG741 | 81 | 82 |
| M0579 | ΔG741 | 83 | 84 |
| | chimΔG741 | 85 | |

New NMB1870 Sequences

Extensive sequence information for NMB1870 is available [e.g. refs 4, 7, 8 and 10]. Further new NMB1870 sequences have been found. These sequences are SEQ ID NOs: 46, 47, 48, 49, 50, 51, 52, 53, 54, 55, 56, 63, 64, 65, 86, 87, 88, 89, 90, 91, 92, 93 and 94.

Sera raised against different NMB1870 proteins were tested against strain NM117. Bactericidal activity was lower for sera raised against proteins in families I, II or III than for the homologous serum. Similarly, sera raised against the NM117 sequence had relatively low SBA activity against strains in NMB1870 families I, II or III.

It will be understood that the invention is described above by way of example only and modifications may be made whilst remaining within the scope and spirit of the invention.

References (The Contents of Which are Hereby Incorporated in Full by Reference)

[1] Jodar et al. (2002) *Lancet* 359(9316):1499-1508.
[2] Pizza et al. (2000) *Science* 287:1816-1820.
[3] WO99/57280.
[4] Masignani et al. (2003) *J Exp Med* 197:789-799.
[5] Welsch et al. (2004) *J Immunol* 172:5605-15.
[6] Hou et al. (2005) *J Infect Dis* 192(4):580-90.
[7] WO03/063766.
[8] Fletcher et al. (2004) *Infect Immun* 72:2088-2100.
[9] Zhu et al. (2005) *Infect Immun* 73(10):6838-45.
[10] WO01/64920.
[11] WO03/020756.
[12] WO2004/048404.
[13] WO2006/024954.
[14] Needleman & Wunsch (1970) *J. Mod. Biol.* 48, 443-453.
[15] Rice et al. (2000) *Trends Genet* 16:276-277.
[16] Achtman (1995) *Global epidemiology of meningococcal disease*. Pages 159-175 of *Meningococcal disease* (ed. Cartwight). ISBN: 0-471-95259-1.
[17] Caugant (1998) *APMIS* 106:505-525.
[18] Maiden et al. (1998) *Proc. Natl. Acad. Sci. USA* 95:3140-3145.
[19] WO01/30390.
[20] Gennaro (2000) *Remington: The Science and Practice of Pharmacy.* 20th edition, ISBN: 0683306472.
[21] WO03/009869.
[22] Vaccine Design . . . (1995) eds. Powell & Newman. ISBN: 030644867X. Plenum.
[23] WO00/23105.
[24] WO90/14837.
[25] U.S. Pat. No. 5,057,540.
[26] WO96/33739.
[27] EP-A-0109942.
[28] WO96/11711.
[29] WO00/07621.
[30] Barr et al. (1998) *Advanced Drug Delivery Reviews* 32:247-271.
[31] Sjolanderet et al. (1998) *Advanced Drug Delivery Reviews* 32:321-338.
[32] Niikura et al. (2002) *Virology* 293:273-280.
[33] Lenz et al. (2001) *J Immunol* 166:5346-5355.
[34] Pinto et al. (2003) *J Infect Dis* 188:327-338.
[35] Gerber et al. (2001) *Viral* 75:4752-4760.
[36] WO03/024480
[37] WO03/024481
[38] Gluck et al. (2002) *Vaccine* 20:B10-B16.
[39] EP-A-0689454.
[40] Johnson et al. (1999) *Bioorg Med Chem Lett* 9:2273-2278.
[41] Evans et al. (2003) *Expert Rev Vaccines* 2:219-229.
[42] Meraldi et al. (2003) *Vaccine* 21:2485-2491.
[43] Pajak et al (2003) *Vaccine* 21:836-842.
[44] Kandimalla et al. (2003) *Nucleic Acids Research* 31:2393-2400.
[45] WO02/26757.
[46] WO99/62923.
[47] Krieg (2003) *Nature Medicine* 9:831-835.
[48] McCluskie et al. (2002) *FEMS Immunology and Medical Microbiology* 32:179-185.
[49] WO98/40100.
[50] U.S. Pat. No. 6,207,646.
[51] U.S. Pat. No. 6,239,116.
[52] U.S. Pat. No. 6,429,199.
[53] Kandimalla et al. (2003) *Biochemical Society Transactions* 31 (part 3):654-658.
[54] Blackwell et al. (2003) *J Immunol* 170:4061-4068.
[55] Krieg (2002) *Trends Immunol* 23:64-65.
[56] WO01/95935.
[57] Kandimalla et al. (2003) *BBRC* 306:948-953.
[58] Bhagat et al. (2003) *BBRC* 300:853-861.
[59] WO03/035836.
[60] WO95/17211.
[61] WO98/42375.
[62] Beignon et al. (2002) *Infect Immun* 70:3012-3019.
[63] Pizza et al. (2001) *Vaccine* 19:2534-2541.
[64] Pizza et al. (2000) *Int J Med Microbiol* 290:455-461.
[65] Scharton-Kersten et al. (2000) *Infect Immun* 68:5306-5313.
[66] Ryan et al. (1999) *Infect Immun* 67:6270-6280.
[67] Partidos et al. (1999) *Immunol Lett* 67:209-216.
[68] Peppoloni et al. (2003) *Expert Rev Vaccines* 2:285-293.
[69] Pine et al. (2002) *J Control Release* 85:263-270.
[70] Domenighini et al. (1995) *Mol Microbial* 15:1165-1167.
[71] WO99/40936.
[72] WO99/44636.
[73] Singh et al] (2001) *J Cont Release* 70:267-276.
[74] WO99/27960.
[75] U.S. Pat. No. 6,090,406

[76] U.S. Pat. No. 5,916,588

[77] EP-A-0626169.

[78] WO99/52549.

[79] WO01/21207.

[80] WO01/21152.

[81] Andrianov et al. (1998) *Biomaterials* 19:109-115.

[82] Payne et al. (1998) *Adv Drug Delivery Review* 31:185-196.

[83] Stanley (2002) *Clin Exp Dermatol* 27:571-577.

[84] Jones (2003) *Curr Opin Investig Drugs* 4:214-218.

[85] WO99/11241.

[86] WO94/00153.

[87] WO98/57659.

[88] European patent applications 0835318, 0735898 and 0761231.

[89] WO99/24578.

[90] WO99/36544.

[91] Costantino et al. (1992) *Vaccine* 10:691-698.

[92] Costantino et al. (1999) *Vaccine* 17:1251-1263.

[93] WO03/007985.

[94] Watson (2000) *Pediatr Infect Dis J* 19:331-332.

[95] Rubin (2000) *Pediatr Clin North Am* 47:269-285, v.

[96] Jedrzejas (2001) *Microbiol Mol Biol Rev* 65:187-207.

[97] Bell (2000) *Pediatr Infect Dis J* 19:1187-1188.

[98] Iwarson (1995) *APMIS* 103:321-326.

[99] Gerlich et al. (1990) *Vaccine* 8 Suppl:S63-68 & 79-80.

[100] Vaccines (1988) eds. Plotkin & Mortimer. ISBN 0-7216-1946-0.

[101] Del Guidice et al. (1998) *Molecular Aspects of Medicine* 19:1-70.

[102] Gustafsson et al. (1996) *N. Engl. J. Med.* 334:349-355.

[103] Rappuoli et al. (1991) *TIBTECH*9:232-238.

[104] Sutter et al. (2000) *Pediatr Clin North Am* 47:287-308.

[105] Zimmerman & Spann (1999) *Am Fam Physician* 59:113-118, 125-126.

[106] McMichael (2000) *Vaccine* 19 Suppl 1:S101-107.

[107] Schuchat (1999) *Lancet* 353(9146):51-6.

[108] WO02/34771.

[109] Dale (1999) *Infect Dis Clin North Am* 13:227-43, viii.

[110] Ferretti et al. (2001) *PNAS USA* 98: 4658-4663.

[111] Kuroda et al (2001) *Lancet* 357(9264):1225-1240; see also pages 1218-1219.

[112] Jones (2001) *Curr Opin Investig Drugs* 2:47-49.

[113] Ravenscroft et al. (1999) *Vaccine* 17:2802-2816.

[114] WO03/080678.

[115] Frash (1990) p.123-145 of *Advances in Biotechnological Processes* vol. 13 (eds. Mizrahi & Van Wezel)

[116] Inzana (1987) *Infect. Immun.* 55:1573-1579.

[117] Kandil et al. (1997) *Glycoconj J* 14:13-17.

[118] Berkin et al. (2002) *Chemistry* 8:4424-4433.

[119] Lindberg (1999) *Vaccine* 17 Suppl 2:S28-36.

[120] Buttery & Moxon (2000) *J R Coll Physicians Lond* 34:163-168.

[121] Ahmad & Chapnick (1999) *Infect Dis Clin North Am* 13:113-33, vii.

[122] Goldblatt (1998) *J. Med Microbiol.* 47:563-567.

[123] European patent 0477508.

[124] U.S. Pat. No. 5,306,492.

[125] WO98/42721.

[126] Dick et al. in *Conjugate Vaccines* (eds. Cruse et al.) Karger, Basel, 1989, 10:48-114.

[127] Hermanson *Bioconjugate Techniques*, Academic Press, San Diego (1996) ISBN: 0123423368.

[128] Kanra et al. (1999) *The Turkish Journal of Paediatrics* 42:421-427.

[129] Ravenscroft et al. (2000) *Dev Biol* (*Basel*) 103: 35-47.

[130] WO97/00697.

[131] WO02/00249.

[132] Zielen et al. (2000) *Infect. Immun.* 68:1435-1440.

[133] Darkes & Plosker (2002) *Paediatr Drugs* 4:609-630.

[134] Tettelin et al. (2001) *Science* 293:498-506.

[135] Hoskins et al (2001) *J Bacteriol* 183:5709-5717.

[136] Rappuoli (2000) *Curr Opin Microbiol* 3:445-450

[137] Rappuoli (2001) *Vaccine* 19:2688-2691.

[138] Masignani et al. (2002) *Expert Opin Biol Ther* 2:895-905.

[139] Mora et al. (2003) *Drug Discov Today* 8:459-464.

[140] Wizemann et al. (2001) *Infect Immun* 69:1593-1598.

[141] Rigden et al. (2003) *Crit Rev Biochem Mol Biol* 38:143-168.

[142] WO02/22167.

[143] Ramsay et al. (2001) *Lancet* 357(9251):195-196.

[144*] Research Disclosure,* 453077 (January 2002)

[145] Anderson (1983) *Infect Immun* 39(1):233-238.

[146] Anderson et al. (1985) *J Clin Invest* 76(1):52-59.

[147] EP-A-0372501

[148] EP-A-0378881

[149] EP-A-0427347

[150] WO93/17712

[151] WO94/03208

[152] WO98/58668

[153] EP-A-0471177

[154] WO00/56360

[155] EP-A-0594610.

[156] WO91/01146

[157] Falugi et al. (2001) *Eur J Immunol* 31:3816-3824.

[158] WO02/091998.

[159] WO00/61761

[160] WO01/72337

[161] WO99/42130

[162] WO96/40242

[163] Lees et al. (1996) *Vaccine* 14:190-198.

[164] WO95/08348.

[165] U.S. Pat. No. 4,882,317

[166] U.S. Pat. No. 4,695,624

[167] Porro et al. (1985) *Mol Immunol* 22:907-919.s

[168] EP-A-0208375

[169] WO00/10599

[170] Geyer et al. Med. Microbiol. Immunol, 165 : 171-288 (1979).

[171] U.S. Pat. No. 4,057,685.

[172] U.S. Pat. Nos. 4,673,574; 4,761,283; 4,808,700.

[173] U.S. Pat. No. 4,459,286.

[174] U.S. Pat. No. 4,965,338

[175] U.S. Pat. No. 4,663,160.

[176] U.S. Pat. No. 4,761,283

[177] U.S. Pat. No. 4,356,170

[178] Lei et al. (2000) *Dev Biol* (*Basel*) 103:259-264.

[179] WO00/38711; U.S. Pat. No. 6,146,902.

[180] WO02/09643.

[181] Katial et al. (2002) *Infect Immun* 70:702-707.

[182] WO01/52885.

[183] European patent 0301992.

[184] Bjune et al. (1991) *Lancet* 338(8775):1093-1096.

[185] Fukasawa et al. (1999) *Vaccine* 17:2951-2958.

[186] WO02/09746.

[187] Rosenqvist et al. (1998) *Dev. Biol. Stand* 92:323-333.

[188] WO01/09350.

[189] European patent 0449958.

[190] EP-A-0996712.
[191] EP-A-0680512.
[192] WO02/062378.
[193] WO99/59625.
[194] U.S. Pat. No. 6,180,111.
[195] WO01/34642.
[196] WO03/051379.
[197] U.S. Pat. No. 6,558,677.
[198] WO2004/019977.
[199] WO02/062380.
[200] WO00/25811.
[201] Peeters et al. (1996) *Vaccine* 14:1008-1015.
[202] Vermont et al. (2003) *Infect Immun* 71:1650-1655.
[203] WO2004/094596

BRIEF DESCRIPTION OF THE SEQUENCE LISTING

| SEQ ID NO: | Description |
|---|---|
| 1 | NMB1870 from strain MC58-family I |
| 2 | NMB1870 from strains 961-5945 & 2996-family II |
| 3 | NMB1870 from strain M1239-family III |
| 4-6 | Domains A to C from SEQ ID NO: 1 |
| 7-9 | Domains A to C from SEQ ID NO: 2 |
| 10-12 | Domains A to C from SEQ ID NO: 3 |
| 13 | mature domain A from SEQ ID NO: 4 |
| 14 | Protein 936 |
| 15-21 | Linkers, etc. |
| 22-24 | ΔG versions of SEQ ID NOs: 1, 2 & 3 |
| 25 | Truncated SEQ ID NO: 14 |
| 26 | Linker |
| 27-40 | Hybrids & tandems |
| 41-45 | Linkers, etc. |
| 46-56 | Polymorphic forms of NMB1870 |
| 57 | Reference sequence for substitutions |
| 58-60 | Chimeric sequences |
| 61-62 | Sequences swapped in SEQ ID NO: 57 |
| 63-65 | NMB1870 from various strains |
| 66 | Linker |
| 67-85 | Primers |
| 86-94 | NMB1870 from various strains |
| 95 | ΔG form of NMNB1870 from strain nm 117 |

The invention claimed is:

1. A polypeptide comprising an amino acid sequence that has at least 85% identity to SEQ ID NO:57, and wherein residue L118 is substituted with another amino acid.

2. The polypeptide of claim 1, wherein the amino acid sequence has at least 90% identity to SEQ ID NO:57.

3. The polypeptide of claim 1, further comprising at least one surface loop sequence from a second family of NMB 1870 in place of a surface loop sequence from the first family.

4. A hybrid polypeptide of formula: wherein: X is an amino acid sequence comprising a Neisserial sequence, L is an optional linker amino acid sequence, A is an optional terminal amino acid sequence, B is an optional C terminal amino acid sequence, and n is 2 or more, wherein at least one of the —X— moieties is the polypeptide of claim 1.

* * * * *

```
                         SEQUENCE LISTING


<160> NUMBER OF SEQ ID NOS: 95

<210> SEQ ID NO 1
<211> LENGTH: 274
<212> TYPE: PRT
<213> ORGANISM: Neisseria meningitidis

<400> SEQUENCE: 1

Met Asn Arg Thr Ala Phe Cys Cys Leu Ser Leu Thr Thr Ala Leu Ile
1               5                   10                  15

Leu Thr Ala Cys Ser Ser Gly Gly Gly Gly Val Ala Ala Asp Ile Gly
            20                  25                  30

Ala Gly Leu Ala Asp Ala Leu Thr Ala Pro Leu Asp His Lys Asp Lys
        35                  40                  45

Gly Leu Gln Ser Leu Thr Leu Asp Gln Ser Val Arg Lys Asn Glu Lys
    50                  55                  60

Leu Lys Leu Ala Ala Gln Gly Ala Glu Lys Thr Tyr Gly Asn Gly Asp
65                  70                  75                  80

Ser Leu Asn Thr Gly Lys Leu Lys Asn Asp Lys Val Ser Arg Phe Asp
                85                  90                  95

Phe Ile Arg Gln Ile Glu Val Asp Gly Gln Leu Ile Thr Leu Glu Ser
            100                 105                 110

Gly Glu Phe Gln Val Tyr Lys Gln Ser His Ser Ala Leu Thr Ala Phe
        115                 120                 125

Gln Thr Glu Gln Ile Gln Asp Ser Glu His Ser Gly Lys Met Val Ala
    130                 135                 140

Lys Arg Gln Phe Arg Ile Gly Asp Ile Ala Gly Glu His Thr Ser Phe
145                 150                 155                 160

Asp Lys Leu Pro Glu Gly Gly Arg Ala Thr Tyr Arg Gly Thr Ala Phe
                165                 170                 175

Gly Ser Asp Asp Ala Gly Gly Lys Leu Thr Tyr Thr Ile Asp Phe Ala
            180                 185                 190

Ala Lys Gln Gly Asn Gly Lys Ile Glu His Leu Lys Ser Pro Glu Leu
        195                 200                 205
```

-continued

```
Asn Val Asp Leu Ala Ala Ala Asp Ile Lys Pro Asp Gly Lys Arg His
    210                 215                 220

Ala Val Ile Ser Gly Ser Val Leu Tyr Asn Gln Ala Glu Lys Gly Ser
225                 230                 235                 240

Tyr Ser Leu Gly Ile Phe Gly Gly Lys Ala Gln Glu Val Ala Gly Ser
                245                 250                 255

Ala Glu Val Lys Thr Val Asn Gly Ile Arg His Ile Gly Leu Ala Ala
            260                 265                 270

Lys Gln


<210> SEQ ID NO 2
<211> LENGTH: 273
<212> TYPE: PRT
<213> ORGANISM: Neisseria meningitidis

<400> SEQUENCE: 2

Met Asn Arg Thr Ala Phe Cys Cys Leu Ser Leu Thr Ala Ala Leu Ile
1               5                   10                  15

Leu Thr Ala Cys Ser Ser Gly Gly Gly Gly Val Ala Ala Asp Ile Gly
            20                  25                  30

Ala Gly Leu Ala Asp Ala Leu Thr Ala Pro Leu Asp His Lys Asp Lys
        35                  40                  45

Ser Leu Gln Ser Leu Thr Leu Asp Gln Ser Val Arg Lys Asn Glu Lys
    50                  55                  60

Leu Lys Leu Ala Ala Gln Gly Ala Glu Lys Thr Tyr Gly Asn Gly Asp
65                  70                  75                  80

Ser Leu Asn Thr Gly Lys Leu Lys Asn Asp Lys Val Ser Arg Phe Asp
                85                  90                  95

Phe Ile Arg Gln Ile Glu Val Asp Gly Gln Leu Ile Thr Leu Glu Ser
            100                 105                 110

Gly Glu Phe Gln Ile Tyr Lys Gln Asp His Ser Ala Val Val Ala Leu
        115                 120                 125

Gln Ile Glu Lys Ile Asn Asn Pro Asp Lys Ile Asp Ser Leu Ile Asn
    130                 135                 140

Gln Arg Ser Phe Leu Val Ser Gly Leu Gly Gly Glu His Thr Ala Phe
145                 150                 155                 160

Asn Gln Leu Pro Asp Gly Lys Ala Glu Tyr His Gly Lys Ala Phe Ser
                165                 170                 175

Ser Asp Asp Ala Gly Gly Lys Leu Thr Tyr Thr Ile Asp Phe Ala Ala
            180                 185                 190

Lys Gln Gly His Gly Lys Ile Glu His Leu Lys Thr Pro Glu Gln Asn
        195                 200                 205

Val Glu Leu Ala Ala Ala Glu Leu Lys Ala Asp Glu Lys Ser His Ala
    210                 215                 220

Val Ile Leu Gly Asp Thr Arg Tyr Gly Ser Glu Glu Lys Gly Thr Tyr
225                 230                 235                 240

His Leu Ala Leu Phe Gly Asp Arg Ala Gln Glu Ile Ala Gly Ser Ala
                245                 250                 255

Thr Val Lys Ile Gly Glu Lys Val His Glu Ile Gly Ile Ala Gly Lys
            260                 265                 270

Gln


<210> SEQ ID NO 3
<211> LENGTH: 281
<212> TYPE: PRT
```

<213> ORGANISM: Neisseria meningitidis

<400> SEQUENCE: 3

```
Met Asn Arg Thr Ala Phe Cys Cys Leu Ser Leu Thr Thr Ala Leu Ile
1               5                   10                  15

Leu Thr Ala Cys Ser Ser Gly Gly Gly Gly Ser Gly Gly Gly Gly Val
            20                  25                  30

Ala Ala Asp Ile Gly Thr Gly Leu Ala Asp Ala Leu Thr Ala Pro Leu
        35                  40                  45

Asp His Lys Asp Lys Gly Leu Lys Ser Leu Thr Leu Glu Asp Ser Ile
    50                  55                  60

Pro Gln Asn Gly Thr Leu Thr Leu Ser Ala Gln Gly Ala Glu Lys Thr
65                  70                  75                  80

Phe Lys Ala Gly Asp Lys Asp Asn Ser Leu Asn Thr Gly Lys Leu Lys
                85                  90                  95

Asn Asp Lys Ile Ser Arg Phe Asp Phe Val Gln Lys Ile Glu Val Asp
            100                 105                 110

Gly Gln Thr Ile Thr Leu Ala Ser Gly Glu Phe Gln Ile Tyr Lys Gln
        115                 120                 125

Asn His Ser Ala Val Val Ala Leu Gln Ile Glu Lys Ile Asn Asn Pro
    130                 135                 140

Asp Lys Thr Asp Ser Leu Ile Asn Gln Arg Ser Phe Leu Val Ser Gly
145                 150                 155                 160

Leu Gly Gly Glu His Thr Ala Phe Asn Gln Leu Pro Gly Gly Lys Ala
                165                 170                 175

Glu Tyr His Gly Lys Ala Phe Ser Ser Asp Asp Pro Asn Gly Arg Leu
            180                 185                 190

His Tyr Ser Ile Asp Phe Thr Lys Lys Gln Gly Tyr Gly Arg Ile Glu
        195                 200                 205

His Leu Lys Thr Leu Glu Gln Asn Val Glu Leu Ala Ala Ala Glu Leu
    210                 215                 220

Lys Ala Asp Glu Lys Ser His Ala Val Ile Leu Gly Asp Thr Arg Tyr
225                 230                 235                 240

Gly Ser Glu Glu Lys Gly Thr Tyr His Leu Ala Leu Phe Gly Asp Arg
                245                 250                 255

Ala Gln Glu Ile Ala Gly Ser Ala Thr Val Lys Ile Gly Glu Lys Val
            260                 265                 270

His Glu Ile Gly Ile Ala Gly Lys Gln
        275                 280
```

<210> SEQ ID NO 4
<211> LENGTH: 119
<212> TYPE: PRT
<213> ORGANISM: Neisseria meningitidis

<400> SEQUENCE: 4

```
Met Asn Arg Thr Ala Phe Cys Cys Leu Ser Leu Thr Thr Ala Leu Ile
1               5                   10                  15

Leu Thr Ala Cys Ser Ser Gly Gly Gly Gly Val Ala Ala Asp Ile Gly
            20                  25                  30

Ala Gly Leu Ala Asp Ala Leu Thr Ala Pro Leu Asp His Lys Asp Lys
        35                  40                  45

Gly Leu Gln Ser Leu Thr Leu Asp Gln Ser Val Arg Lys Asn Glu Lys
    50                  55                  60

Leu Lys Leu Ala Ala Gln Gly Ala Glu Lys Thr Tyr Gly Asn Gly Asp
65                  70                  75                  80
```

-continued

```
Ser Leu Asn Thr Gly Lys Leu Lys Asn Asp Lys Val Ser Arg Phe Asp
                85                  90                  95

Phe Ile Arg Gln Ile Glu Val Asp Gly Gln Leu Ile Thr Leu Glu Ser
            100                 105                 110

Gly Glu Phe Gln Val Tyr Lys
        115


<210> SEQ ID NO 5
<211> LENGTH: 64
<212> TYPE: PRT
<213> ORGANISM: Neisseria meningitidis

<400> SEQUENCE: 5

Gln Ser His Ser Ala Leu Thr Ala Phe Gln Thr Glu Gln Ile Gln Asp
1               5                   10                  15

Ser Glu His Ser Gly Lys Met Val Ala Lys Arg Gln Phe Arg Ile Gly
            20                  25                  30

Asp Ile Ala Gly Glu His Thr Ser Phe Asp Lys Leu Pro Glu Gly Gly
        35                  40                  45

Arg Ala Thr Tyr Arg Gly Thr Ala Phe Gly Ser Asp Asp Ala Gly Gly
    50                  55                  60


<210> SEQ ID NO 6
<211> LENGTH: 91
<212> TYPE: PRT
<213> ORGANISM: Neisseria meningitidis

<400> SEQUENCE: 6

Lys Leu Thr Tyr Thr Ile Asp Phe Ala Ala Lys Gln Gly Asn Gly Lys
1               5                   10                  15

Ile Glu His Leu Lys Ser Pro Glu Leu Asn Val Asp Leu Ala Ala Ala
            20                  25                  30

Asp Ile Lys Pro Asp Gly Lys Arg His Ala Val Ile Ser Gly Ser Val
        35                  40                  45

Leu Tyr Asn Gln Ala Glu Lys Gly Ser Tyr Ser Leu Gly Ile Phe Gly
    50                  55                  60

Gly Lys Ala Gln Glu Val Ala Gly Ser Ala Glu Val Lys Thr Val Asn
65                  70                  75                  80

Gly Ile Arg His Ile Gly Leu Ala Ala Lys Gln
                85                  90


<210> SEQ ID NO 7
<211> LENGTH: 119
<212> TYPE: PRT
<213> ORGANISM: Neisseria meningitidis

<400> SEQUENCE: 7

Met Asn Arg Thr Ala Phe Cys Cys Leu Ser Leu Thr Ala Ala Leu Ile
1               5                   10                  15

Leu Thr Ala Cys Ser Ser Gly Gly Gly Gly Val Ala Ala Asp Ile Gly
            20                  25                  30

Ala Gly Leu Ala Asp Ala Leu Thr Ala Pro Leu Asp His Lys Asp Lys
        35                  40                  45

Ser Leu Gln Ser Leu Thr Leu Asp Gln Ser Val Arg Lys Asn Glu Lys
    50                  55                  60

Leu Lys Leu Ala Ala Gln Gly Ala Glu Lys Thr Tyr Gly Asn Gly Asp
65                  70                  75                  80

Ser Leu Asn Thr Gly Lys Leu Lys Asn Asp Lys Val Ser Arg Phe Asp
```

85 90 95

Phe Ile Arg Gln Ile Glu Val Asp Gly Gln Leu Ile Thr Leu Glu Ser
100 105 110

Gly Glu Phe Gln Ile Tyr Lys
115

<210> SEQ ID NO 8
<211> LENGTH: 63
<212> TYPE: PRT
<213> ORGANISM: Neisseria meningitidis

<400> SEQUENCE: 8

Gln Asp His Ser Ala Val Val Ala Leu Gln Ile Glu Lys Ile Asn Asn
1 5 10 15

Pro Asp Lys Ile Asp Ser Leu Ile Asn Gln Arg Ser Phe Leu Val Ser
20 25 30

Gly Leu Gly Gly Glu His Thr Ala Phe Asn Gln Leu Pro Asp Gly Lys
35 40 45

Ala Glu Tyr His Gly Lys Ala Phe Ser Ser Asp Asp Ala Gly Gly
50 55 60

<210> SEQ ID NO 9
<211> LENGTH: 91
<212> TYPE: PRT
<213> ORGANISM: Neisseria meningitidis

<400> SEQUENCE: 9

Lys Leu Thr Tyr Thr Ile Asp Phe Ala Ala Lys Gln Gly His Gly Lys
1 5 10 15

Ile Glu His Leu Lys Thr Pro Glu Gln Asn Val Glu Leu Ala Ala Ala
20 25 30

Glu Leu Lys Ala Asp Glu Lys Ser His Ala Val Ile Leu Gly Asp Thr
35 40 45

Arg Tyr Gly Ser Glu Glu Lys Gly Thr Tyr His Leu Ala Leu Phe Gly
50 55 60

Asp Arg Ala Gln Glu Ile Ala Gly Ser Ala Thr Val Lys Ile Gly Glu
65 70 75 80

Lys Val His Glu Ile Gly Ile Ala Gly Lys Gln
85 90

<210> SEQ ID NO 10
<211> LENGTH: 127
<212> TYPE: PRT
<213> ORGANISM: Neisseria meningitidis

<400> SEQUENCE: 10

Met Asn Arg Thr Ala Phe Cys Cys Leu Ser Leu Thr Thr Ala Leu Ile
1 5 10 15

Leu Thr Ala Cys Ser Ser Gly Gly Gly Gly Ser Gly Gly Gly Gly Val
20 25 30

Ala Ala Asp Ile Gly Thr Gly Leu Ala Asp Ala Leu Thr Ala Pro Leu
35 40 45

Asp His Lys Asp Lys Gly Leu Lys Ser Leu Thr Leu Glu Asp Ser Ile
50 55 60

Pro Gln Asn Gly Thr Leu Thr Leu Ser Ala Gln Gly Ala Glu Lys Thr
65 70 75 80

Phe Lys Ala Gly Asp Lys Asp Asn Ser Leu Asn Thr Gly Lys Leu Lys
85 90 95

```
Asn Asp Lys Ile Ser Arg Phe Asp Phe Val Gln Lys Ile Glu Val Asp
            100                 105                 110

Gly Gln Thr Ile Thr Leu Ala Ser Gly Glu Phe Gln Ile Tyr Lys
        115                 120                 125


<210> SEQ ID NO 11
<211> LENGTH: 63
<212> TYPE: PRT
<213> ORGANISM: Neisseria meningitidis

<400> SEQUENCE: 11

Gln Asn His Ser Ala Val Val Ala Leu Gln Ile Glu Lys Ile Asn Asn
1               5                   10                  15

Pro Asp Lys Thr Asp Ser Leu Ile Asn Gln Arg Ser Phe Leu Val Ser
            20                  25                  30

Gly Leu Gly Gly Glu His Thr Ala Phe Asn Gln Leu Pro Gly Gly Lys
        35                  40                  45

Ala Glu Tyr His Gly Lys Ala Phe Ser Ser Asp Asp Pro Asn Gly
    50                  55                  60


<210> SEQ ID NO 12
<211> LENGTH: 91
<212> TYPE: PRT
<213> ORGANISM: Neisseria meningitidis

<400> SEQUENCE: 12

Arg Leu His Tyr Ser Ile Asp Phe Thr Lys Lys Gln Gly Tyr Gly Arg
1               5                   10                  15

Ile Glu His Leu Lys Thr Leu Glu Gln Asn Val Glu Leu Ala Ala Ala
            20                  25                  30

Glu Leu Lys Ala Asp Glu Lys Ser His Ala Val Ile Leu Gly Asp Thr
        35                  40                  45

Arg Tyr Gly Ser Glu Glu Lys Gly Thr Tyr His Leu Ala Leu Phe Gly
    50                  55                  60

Asp Arg Ala Gln Glu Ile Ala Gly Ser Ala Thr Val Lys Ile Gly Glu
65                  70                  75                  80

Lys Val His Glu Ile Gly Ile Ala Gly Lys Gln
                85                  90


<210> SEQ ID NO 13
<211> LENGTH: 100
<212> TYPE: PRT
<213> ORGANISM: Neisseria meningitidis

<400> SEQUENCE: 13

Cys Ser Ser Gly Gly Gly Gly Val Ala Ala Asp Ile Gly Ala Gly Leu
1               5                   10                  15

Ala Asp Ala Leu Thr Ala Pro Leu Asp His Lys Asp Lys Gly Leu Gln
            20                  25                  30

Ser Leu Thr Leu Asp Gln Ser Val Arg Lys Asn Glu Lys Leu Lys Leu
        35                  40                  45

Ala Ala Gln Gly Ala Glu Lys Thr Tyr Gly Asn Gly Asp Ser Leu Asn
    50                  55                  60

Thr Gly Lys Leu Lys Asn Asp Lys Val Ser Arg Phe Asp Phe Ile Arg
65                  70                  75                  80

Gln Ile Glu Val Asp Gly Gln Leu Ile Thr Leu Glu Ser Gly Glu Phe
                85                  90                  95

Gln Val Tyr Lys
            100
```

<210> SEQ ID NO 14
<211> LENGTH: 202
<212> TYPE: PRT
<213> ORGANISM: Neisseria meningitidis

<400> SEQUENCE: 14

Met Lys Pro Lys Pro His Thr Val Arg Thr Leu Ile Ala Ala Ile Phe
1 5 10 15

Ser Leu Ala Leu Ser Gly Cys Val Ser Ala Val Ile Gly Ser Ala Ala
20 25 30

Val Gly Ala Lys Ser Ala Val Asp Arg Arg Thr Thr Gly Ala Gln Thr
35 40 45

Asp Asp Asn Val Met Ala Leu Arg Ile Glu Thr Thr Ala Arg Ser Tyr
50 55 60

Leu Arg Gln Asn Asn Gln Thr Lys Gly Tyr Thr Pro Gln Ile Ser Val
65 70 75 80

Val Gly Tyr Asn Arg His Leu Leu Leu Leu Gly Gln Val Ala Thr Glu
85 90 95

Gly Glu Lys Gln Phe Val Gly Gln Ile Ala Arg Ser Glu Gln Ala Ala
100 105 110

Glu Gly Val Tyr Asn Tyr Ile Thr Val Ala Ser Leu Pro Arg Thr Ala
115 120 125

Gly Asp Ile Ala Gly Asp Thr Trp Asn Thr Ser Lys Val Arg Ala Thr
130 135 140

Leu Leu Gly Ile Ser Pro Ala Thr Gln Ala Arg Val Lys Ile Val Thr
145 150 155 160

Tyr Gly Asn Val Thr Tyr Val Met Gly Ile Leu Thr Pro Glu Glu Gln
165 170 175

Ala Gln Ile Thr Gln Lys Val Ser Thr Thr Val Gly Val Gln Lys Val
180 185 190

Ile Thr Leu Tyr Gln Asn Tyr Val Gln Arg
195 200

<210> SEQ ID NO 15
<211> LENGTH: 6
<212> TYPE: PRT
<213> ORGANISM: Neisseria meningitidis

<400> SEQUENCE: 15

Gly Ser Gly Gly Gly Gly
1 5

<210> SEQ ID NO 16
<211> LENGTH: 4
<212> TYPE: PRT
<213> ORGANISM: Neisseria meningitidis

<400> SEQUENCE: 16

Gly Gly Gly Gly
1

<210> SEQ ID NO 17
<211> LENGTH: 11
<212> TYPE: PRT
<213> ORGANISM: Neisseria meningitidis

<400> SEQUENCE: 17

Gly Pro Asp Ser Asp Arg Leu Gln Gln Arg Arg
1 5 10

<210> SEQ ID NO 18
<211> LENGTH: 13
<212> TYPE: PRT
<213> ORGANISM: Neisseria meningitidis

<400> SEQUENCE: 18

Gly Ser Gly Pro Asp Ser Asp Arg Leu Gln Gln Arg Arg
1               5                   10

<210> SEQ ID NO 19
<211> LENGTH: 13
<212> TYPE: PRT
<213> ORGANISM: Neisseria meningitidis

<400> SEQUENCE: 19

Gly Lys Gly Pro Asp Ser Asp Arg Leu Gln Gln Arg Arg
1               5                   10

<210> SEQ ID NO 20
<211> LENGTH: 6
<212> TYPE: PRT
<213> ORGANISM: Neisseria meningitidis

<400> SEQUENCE: 20

His His His His His His
1               5

<210> SEQ ID NO 21
<211> LENGTH: 12
<212> TYPE: PRT
<213> ORGANISM: Neisseria meningitidis

<400> SEQUENCE: 21

Met Gly Pro Asp Ser Asp Arg Leu Gln Gln Arg Arg
1               5                   10

<210> SEQ ID NO 22
<211> LENGTH: 248
<212> TYPE: PRT
<213> ORGANISM: Neisseria meningitidis

<400> SEQUENCE: 22

Val Ala Ala Asp Ile Gly Ala Gly Leu Ala Asp Ala Leu Thr Ala Pro
1               5                   10                  15

Leu Asp His Lys Asp Lys Gly Leu Gln Ser Leu Thr Leu Asp Gln Ser
            20                  25                  30

Val Arg Lys Asn Glu Lys Leu Lys Leu Ala Ala Gln Gly Ala Glu Lys
        35                  40                  45

Thr Tyr Gly Asn Gly Asp Ser Leu Asn Thr Gly Lys Leu Lys Asn Asp
    50                  55                  60

Lys Val Ser Arg Phe Asp Phe Ile Arg Gln Ile Glu Val Asp Gly Gln
65                  70                  75                  80

Leu Ile Thr Leu Glu Ser Gly Glu Phe Gln Val Tyr Lys Gln Ser His
                85                  90                  95

Ser Ala Leu Thr Ala Phe Gln Thr Glu Gln Ile Gln Asp Ser Glu His
            100                 105                 110

Ser Gly Lys Met Val Ala Lys Arg Gln Phe Arg Ile Gly Asp Ile Ala
        115                 120                 125

Gly Glu His Thr Ser Phe Asp Lys Leu Pro Glu Gly Gly Arg Ala Thr
    130                 135                 140

```
Tyr Arg Gly Thr Ala Phe Gly Ser Asp Asp Ala Gly Gly Lys Leu Thr
145                 150                 155                 160

Tyr Thr Ile Asp Phe Ala Ala Lys Gln Gly Asn Gly Lys Ile Glu His
                165                 170                 175

Leu Lys Ser Pro Glu Leu Asn Val Asp Leu Ala Ala Ala Asp Ile Lys
            180                 185                 190

Pro Asp Gly Lys Arg His Ala Val Ile Ser Gly Ser Val Leu Tyr Asn
        195                 200                 205

Gln Ala Glu Lys Gly Ser Tyr Ser Leu Gly Ile Phe Gly Gly Lys Ala
    210                 215                 220

Gln Glu Val Ala Gly Ser Ala Glu Val Lys Thr Val Asn Gly Ile Arg
225                 230                 235                 240

His Ile Gly Leu Ala Ala Lys Gln
                245


<210> SEQ ID NO 23
<211> LENGTH: 247
<212> TYPE: PRT
<213> ORGANISM: Neisseria meningitidis

<400> SEQUENCE: 23

Val Ala Ala Asp Ile Gly Ala Gly Leu Ala Asp Ala Leu Thr Ala Pro
1               5                   10                  15

Leu Asp His Lys Asp Lys Ser Leu Gln Ser Leu Thr Leu Asp Gln Ser
            20                  25                  30

Val Arg Lys Asn Glu Lys Leu Lys Leu Ala Ala Gln Gly Ala Glu Lys
        35                  40                  45

Thr Tyr Gly Asn Gly Asp Ser Leu Asn Thr Gly Lys Leu Lys Asn Asp
    50                  55                  60

Lys Val Ser Arg Phe Asp Phe Ile Arg Gln Ile Glu Val Asp Gly Gln
65                  70                  75                  80

Leu Ile Thr Leu Glu Ser Gly Glu Phe Gln Ile Tyr Lys Gln Asp His
                85                  90                  95

Ser Ala Val Val Ala Leu Gln Ile Glu Lys Ile Asn Asn Pro Asp Lys
            100                 105                 110

Ile Asp Ser Leu Ile Asn Gln Arg Ser Phe Leu Val Ser Gly Leu Gly
        115                 120                 125

Gly Glu His Thr Ala Phe Asn Gln Leu Pro Asp Gly Lys Ala Glu Tyr
    130                 135                 140

His Gly Lys Ala Phe Ser Ser Asp Asp Ala Gly Gly Lys Leu Thr Tyr
145                 150                 155                 160

Thr Ile Asp Phe Ala Ala Lys Gln Gly His Gly Lys Ile Glu His Leu
                165                 170                 175

Lys Thr Pro Glu Gln Asn Val Glu Leu Ala Ala Ala Glu Leu Lys Ala
            180                 185                 190

Asp Glu Lys Ser His Ala Val Ile Leu Gly Asp Thr Arg Tyr Gly Ser
        195                 200                 205

Glu Glu Lys Gly Thr Tyr His Leu Ala Leu Phe Gly Asp Arg Ala Gln
    210                 215                 220

Glu Ile Ala Gly Ser Ala Thr Val Lys Ile Gly Glu Lys Val His Glu
225                 230                 235                 240

Ile Gly Ile Ala Gly Lys Gln
                245


<210> SEQ ID NO 24
<211> LENGTH: 250
```

<212> TYPE: PRT
<213> ORGANISM: Neisseria meningitidis

<400> SEQUENCE: 24

```
Val Ala Ala Asp Ile Gly Thr Gly Leu Ala Asp Ala Leu Thr Ala Pro
1               5                   10                  15

Leu Asp His Lys Asp Lys Gly Leu Lys Ser Leu Thr Leu Glu Asp Ser
            20                  25                  30

Ile Pro Gln Asn Gly Thr Leu Thr Leu Ser Ala Gln Gly Ala Glu Lys
        35                  40                  45

Thr Phe Lys Ala Gly Asp Lys Asp Asn Ser Leu Asn Thr Gly Lys Leu
    50                  55                  60

Lys Asn Asp Lys Ile Ser Arg Phe Asp Phe Val Gln Lys Ile Glu Val
65                  70                  75                  80

Asp Gly Gln Thr Ile Thr Leu Ala Ser Gly Glu Phe Gln Ile Tyr Lys
                85                  90                  95

Gln Asn His Ser Ala Val Val Ala Leu Gln Ile Glu Lys Ile Asn Asn
            100                 105                 110

Pro Asp Lys Thr Asp Ser Leu Ile Asn Gln Arg Ser Phe Leu Val Ser
        115                 120                 125

Gly Leu Gly Gly Glu His Thr Ala Phe Asn Gln Leu Pro Gly Gly Lys
    130                 135                 140

Ala Glu Tyr His Gly Lys Ala Phe Ser Ser Asp Asp Pro Asn Gly Arg
145                 150                 155                 160

Leu His Tyr Ser Ile Asp Phe Thr Lys Lys Gln Gly Tyr Gly Arg Ile
                165                 170                 175

Glu His Leu Lys Thr Leu Glu Gln Asn Val Glu Leu Ala Ala Ala Glu
            180                 185                 190

Leu Lys Ala Asp Glu Lys Ser His Ala Val Ile Leu Gly Asp Thr Arg
        195                 200                 205

Tyr Gly Ser Glu Glu Lys Gly Thr Tyr His Leu Ala Leu Phe Gly Asp
    210                 215                 220

Arg Ala Gln Glu Ile Ala Gly Ser Ala Thr Val Lys Ile Gly Glu Lys
225                 230                 235                 240

Val His Glu Ile Gly Ile Ala Gly Lys Gln
                245                 250
```

<210> SEQ ID NO 25
<211> LENGTH: 179
<212> TYPE: PRT
<213> ORGANISM: Neisseria meningitidis

<400> SEQUENCE: 25

```
Val Ser Ala Val Ile Gly Ser Ala Ala Val Gly Ala Lys Ser Ala Val
1               5                   10                  15

Asp Arg Arg Thr Thr Gly Ala Gln Thr Asp Asp Asn Val Met Ala Leu
            20                  25                  30

Arg Ile Glu Thr Thr Ala Arg Ser Tyr Leu Arg Gln Asn Asn Gln Thr
        35                  40                  45

Lys Gly Tyr Thr Pro Gln Ile Ser Val Val Gly Tyr Asn Arg His Leu
    50                  55                  60

Leu Leu Leu Gly Gln Val Ala Thr Glu Gly Glu Lys Gln Phe Val Gly
65                  70                  75                  80

Gln Ile Ala Arg Ser Glu Gln Ala Ala Glu Gly Val Tyr Asn Tyr Ile
                85                  90                  95

Thr Val Ala Ser Leu Pro Arg Thr Ala Gly Asp Ile Ala Gly Asp Thr
```

-continued

```
            100                 105                 110

Trp Asn Thr Ser Lys Val Arg Ala Thr Leu Leu Gly Ile Ser Pro Ala
        115                 120                 125

Thr Gln Ala Arg Val Lys Ile Val Thr Tyr Gly Asn Val Thr Tyr Val
    130                 135                 140

Met Gly Ile Leu Thr Pro Glu Glu Gln Ala Gln Ile Thr Gln Lys Val
145                 150                 155                 160

Ser Thr Thr Val Gly Val Gln Lys Val Ile Thr Leu Tyr Gln Asn Tyr
                165                 170                 175

Val Gln Arg


<210> SEQ ID NO 26
<211> LENGTH: 3
<212> TYPE: PRT
<213> ORGANISM: Neisseria meningitidis

<400> SEQUENCE: 26

Met Ala Ser
1


<210> SEQ ID NO 27
<211> LENGTH: 521
<212> TYPE: PRT
<213> ORGANISM: Neisseria meningitidis

<400> SEQUENCE: 27

Met Gly Pro Asp Ser Asp Arg Leu Gln Gln Arg Arg Val Ala Ala Asp
1               5                   10                  15

Ile Gly Ala Gly Leu Ala Asp Ala Leu Thr Ala Pro Leu Asp His Lys
            20                  25                  30

Asp Lys Ser Leu Gln Ser Leu Thr Leu Asp Gln Ser Val Arg Lys Asn
        35                  40                  45

Glu Lys Leu Lys Leu Ala Ala Gln Gly Ala Glu Lys Thr Tyr Gly Asn
    50                  55                  60

Gly Asp Ser Leu Asn Thr Gly Lys Leu Lys Asn Asp Lys Val Ser Arg
65                  70                  75                  80

Phe Asp Phe Ile Arg Gln Ile Glu Val Asp Gly Gln Leu Ile Thr Leu
                85                  90                  95

Glu Ser Gly Glu Phe Gln Ile Tyr Lys Gln Asp His Ser Ala Val Val
            100                 105                 110

Ala Leu Gln Ile Glu Lys Ile Asn Asn Pro Asp Lys Ile Asp Ser Leu
        115                 120                 125

Ile Asn Gln Arg Ser Phe Leu Val Ser Gly Leu Gly Gly Glu His Thr
    130                 135                 140

Ala Phe Asn Gln Leu Pro Asp Gly Lys Ala Glu Tyr His Gly Lys Ala
145                 150                 155                 160

Phe Ser Ser Asp Asp Ala Gly Gly Lys Leu Thr Tyr Thr Ile Asp Phe
                165                 170                 175

Ala Ala Lys Gln Gly His Gly Lys Ile Glu His Leu Lys Thr Pro Glu
            180                 185                 190

Gln Asn Val Glu Leu Ala Ala Ala Glu Leu Lys Ala Asp Glu Lys Ser
        195                 200                 205

His Ala Val Ile Leu Gly Asp Thr Arg Tyr Gly Ser Glu Glu Lys Gly
    210                 215                 220

Thr Tyr His Leu Ala Leu Phe Gly Asp Arg Ala Gln Glu Ile Ala Gly
225                 230                 235                 240
```

-continued

```
Ser Ala Thr Val Lys Ile Gly Glu Lys Val His Glu Ile Gly Ile Ala
                245                 250                 255

Gly Lys Gln Gly Ser Gly Gly Gly Gly Val Ala Ala Asp Ile Gly Ala
            260                 265                 270

Gly Leu Ala Asp Ala Leu Thr Ala Pro Leu Asp His Lys Asp Lys Gly
        275                 280                 285

Leu Gln Ser Leu Thr Leu Asp Gln Ser Val Arg Lys Asn Glu Lys Leu
    290                 295                 300

Lys Leu Ala Ala Gln Gly Ala Glu Lys Thr Tyr Gly Asn Gly Asp Ser
305                 310                 315                 320

Leu Asn Thr Gly Lys Leu Lys Asn Asp Lys Val Ser Arg Phe Asp Phe
                325                 330                 335

Ile Arg Gln Ile Glu Val Asp Gly Gln Leu Ile Thr Leu Glu Ser Gly
            340                 345                 350

Glu Phe Gln Val Tyr Lys Gln Ser His Ser Ala Leu Thr Ala Phe Gln
        355                 360                 365

Thr Glu Gln Ile Gln Asp Ser Glu His Ser Gly Lys Met Val Ala Lys
    370                 375                 380

Arg Gln Phe Arg Ile Gly Asp Ile Ala Gly Glu His Thr Ser Phe Asp
385                 390                 395                 400

Lys Leu Pro Glu Gly Gly Arg Ala Thr Tyr Arg Gly Thr Ala Phe Gly
                405                 410                 415

Ser Asp Asp Ala Gly Gly Lys Leu Thr Tyr Thr Ile Asp Phe Ala Ala
            420                 425                 430

Lys Gln Gly Asn Gly Lys Ile Glu His Leu Lys Ser Pro Glu Leu Asn
        435                 440                 445

Val Asp Leu Ala Ala Ala Asp Ile Lys Pro Asp Gly Lys Arg His Ala
    450                 455                 460

Val Ile Ser Gly Ser Val Leu Tyr Asn Gln Ala Glu Lys Gly Ser Tyr
465                 470                 475                 480

Ser Leu Gly Ile Phe Gly Gly Lys Ala Gln Glu Val Ala Gly Ser Ala
                485                 490                 495

Glu Val Lys Thr Val Asn Gly Ile Arg His Ile Gly Leu Ala Ala Lys
            500                 505                 510

Gln Leu Glu His His His His His His
        515                 520


<210> SEQ ID NO 28
<211> LENGTH: 704
<212> TYPE: PRT
<213> ORGANISM: Neisseria meningitidis

<400> SEQUENCE: 28

Met Ala Ser Val Ser Ala Val Ile Gly Ser Ala Ala Val Gly Ala Lys
1               5                   10                  15

Ser Ala Val Asp Arg Arg Thr Thr Gly Ala Gln Thr Asp Asp Asn Val
            20                  25                  30

Met Ala Leu Arg Ile Glu Thr Thr Ala Arg Ser Tyr Leu Arg Gln Asn
        35                  40                  45

Asn Gln Thr Lys Gly Tyr Thr Pro Gln Ile Ser Val Val Gly Tyr Asn
    50                  55                  60

Arg His Leu Leu Leu Leu Gly Gln Val Ala Thr Glu Gly Glu Lys Gln
65                  70                  75                  80

Phe Val Gly Gln Ile Ala Arg Ser Glu Gln Ala Ala Glu Gly Val Tyr
                85                  90                  95
```

-continued

```
Asn Tyr Ile Thr Val Ala Ser Leu Pro Arg Thr Ala Gly Asp Ile Ala
            100                 105                 110

Gly Asp Thr Trp Asn Thr Ser Lys Val Arg Ala Thr Leu Leu Gly Ile
        115                 120                 125

Ser Pro Ala Thr Gln Ala Arg Val Lys Ile Val Thr Tyr Gly Asn Val
    130                 135                 140

Thr Tyr Val Met Gly Ile Leu Thr Pro Glu Glu Gln Ala Gln Ile Thr
145                 150                 155                 160

Gln Lys Val Ser Thr Thr Val Gly Val Gln Lys Val Ile Thr Leu Tyr
                165                 170                 175

Gln Asn Tyr Val Gln Arg Gly Ser Gly Gly Gly Gly Val Ala Ala Asp
            180                 185                 190

Ile Gly Ala Gly Leu Ala Asp Ala Leu Thr Ala Pro Leu Asp His Lys
        195                 200                 205

Asp Lys Gly Leu Gln Ser Leu Thr Leu Asp Gln Ser Val Arg Lys Asn
    210                 215                 220

Glu Lys Leu Lys Leu Ala Ala Gln Gly Ala Glu Lys Thr Tyr Gly Asn
225                 230                 235                 240

Gly Asp Ser Leu Asn Thr Gly Lys Leu Lys Asn Asp Lys Val Ser Arg
                245                 250                 255

Phe Asp Phe Ile Arg Gln Ile Glu Val Asp Gly Gln Leu Ile Thr Leu
            260                 265                 270

Glu Ser Gly Glu Phe Gln Val Tyr Lys Gln Ser His Ser Ala Leu Thr
        275                 280                 285

Ala Phe Gln Thr Glu Gln Ile Gln Asp Ser Glu His Ser Gly Lys Met
    290                 295                 300

Val Ala Lys Arg Gln Phe Arg Ile Gly Asp Ile Ala Gly Glu His Thr
305                 310                 315                 320

Ser Phe Asp Lys Leu Pro Glu Gly Gly Arg Ala Thr Tyr Arg Gly Thr
                325                 330                 335

Ala Phe Gly Ser Asp Asp Ala Gly Gly Lys Leu Thr Tyr Thr Ile Asp
            340                 345                 350

Phe Ala Ala Lys Gln Gly Asn Gly Lys Ile Glu His Leu Lys Ser Pro
        355                 360                 365

Glu Leu Asn Val Asp Leu Ala Ala Ala Asp Ile Lys Pro Asp Gly Lys
    370                 375                 380

Arg His Ala Val Ile Ser Gly Ser Val Leu Tyr Asn Gln Ala Glu Lys
385                 390                 395                 400

Gly Ser Tyr Ser Leu Gly Ile Phe Gly Gly Lys Ala Gln Glu Val Ala
                405                 410                 415

Gly Ser Ala Glu Val Lys Thr Val Asn Gly Ile Arg His Ile Gly Leu
            420                 425                 430

Ala Ala Lys Gln Gly Ser Gly Pro Asp Ser Asp Arg Leu Gln Gln Arg
        435                 440                 445

Arg Val Ala Ala Asp Ile Gly Ala Gly Leu Ala Asp Ala Leu Thr Ala
    450                 455                 460

Pro Leu Asp His Lys Asp Lys Ser Leu Gln Ser Leu Thr Leu Asp Gln
465                 470                 475                 480

Ser Val Arg Lys Asn Glu Lys Leu Lys Leu Ala Ala Gln Gly Ala Glu
                485                 490                 495

Lys Thr Tyr Gly Asn Gly Asp Ser Leu Asn Thr Gly Lys Leu Lys Asn
            500                 505                 510

Asp Lys Val Ser Arg Phe Asp Phe Ile Arg Gln Ile Glu Val Asp Gly
        515                 520                 525
```

Gln Leu Ile Thr Leu Glu Ser Gly Glu Phe Gln Ile Tyr Lys Gln Asp
    530                 535                 540

His Ser Ala Val Val Ala Leu Gln Ile Glu Lys Ile Asn Asn Pro Asp
545                 550                 555                 560

Lys Ile Asp Ser Leu Ile Asn Gln Arg Ser Phe Leu Val Ser Gly Leu
                565                 570                 575

Gly Gly Glu His Thr Ala Phe Asn Gln Leu Pro Asp Gly Lys Ala Glu
            580                 585                 590

Tyr His Gly Lys Ala Phe Ser Ser Asp Asp Ala Gly Gly Lys Leu Thr
        595                 600                 605

Tyr Thr Ile Asp Phe Ala Ala Lys Gln Gly His Gly Lys Ile Glu His
    610                 615                 620

Leu Lys Thr Pro Glu Gln Asn Val Glu Leu Ala Ala Ala Glu Leu Lys
625                 630                 635                 640

Ala Asp Glu Lys Ser His Ala Val Ile Leu Gly Asp Thr Arg Tyr Gly
                645                 650                 655

Ser Glu Glu Lys Gly Thr Tyr His Leu Ala Leu Phe Gly Asp Arg Ala
            660                 665                 670

Gln Glu Ile Ala Gly Ser Ala Thr Val Lys Ile Gly Glu Lys Val His
        675                 680                 685

Glu Ile Gly Ile Ala Gly Lys Gln Leu Glu His His His His His His
    690                 695                 700

<210> SEQ ID NO 29
<211> LENGTH: 704
<212> TYPE: PRT
<213> ORGANISM: Neisseria meningitidis

<400> SEQUENCE: 29

Met Ala Ser Val Ser Ala Val Ile Gly Ser Ala Ala Val Gly Ala Lys
1               5                   10                  15

Ser Ala Val Asp Arg Arg Thr Thr Gly Ala Gln Thr Asp Asp Asn Val
            20                  25                  30

Met Ala Leu Arg Ile Glu Thr Thr Ala Arg Ser Tyr Leu Arg Gln Asn
        35                  40                  45

Asn Gln Thr Lys Gly Tyr Thr Pro Gln Ile Ser Val Val Gly Tyr Asn
    50                  55                  60

Arg His Leu Leu Leu Leu Gly Gln Val Ala Thr Glu Gly Glu Lys Gln
65                  70                  75                  80

Phe Val Gly Gln Ile Ala Arg Ser Glu Gln Ala Ala Glu Gly Val Tyr
                85                  90                  95

Asn Tyr Ile Thr Val Ala Ser Leu Pro Arg Thr Ala Gly Asp Ile Ala
            100                 105                 110

Gly Asp Thr Trp Asn Thr Ser Lys Val Arg Ala Thr Leu Leu Gly Ile
        115                 120                 125

Ser Pro Ala Thr Gln Ala Arg Val Lys Ile Val Thr Tyr Gly Asn Val
    130                 135                 140

Thr Tyr Val Met Gly Ile Leu Thr Pro Glu Glu Gln Ala Gln Ile Thr
145                 150                 155                 160

Gln Lys Val Ser Thr Thr Val Gly Val Gln Lys Val Ile Thr Leu Tyr
                165                 170                 175

Gln Asn Tyr Val Gln Arg Gly Ser Gly Pro Asp Ser Asp Arg Leu Gln
            180                 185                 190

Gln Arg Arg Val Ala Ala Asp Ile Gly Ala Gly Leu Ala Asp Ala Leu
        195                 200                 205

-continued

```
Thr Ala Pro Leu Asp His Lys Asp Lys Ser Leu Gln Ser Leu Thr Leu
    210                 215                 220

Asp Gln Ser Val Arg Lys Asn Glu Lys Leu Lys Leu Ala Ala Gln Gly
225                 230                 235                 240

Ala Glu Lys Thr Tyr Gly Asn Gly Asp Ser Leu Asn Thr Gly Lys Leu
                245                 250                 255

Lys Asn Asp Lys Val Ser Arg Phe Asp Phe Ile Arg Gln Ile Glu Val
            260                 265                 270

Asp Gly Gln Leu Ile Thr Leu Glu Ser Gly Glu Phe Gln Ile Tyr Lys
        275                 280                 285

Gln Asp His Ser Ala Val Val Ala Leu Gln Ile Glu Lys Ile Asn Asn
    290                 295                 300

Pro Asp Lys Ile Asp Ser Leu Ile Asn Gln Arg Ser Phe Leu Val Ser
305                 310                 315                 320

Gly Leu Gly Gly Glu His Thr Ala Phe Asn Gln Leu Pro Asp Gly Lys
                325                 330                 335

Ala Glu Tyr His Gly Lys Ala Phe Ser Ser Asp Asp Ala Gly Gly Lys
            340                 345                 350

Leu Thr Tyr Thr Ile Asp Phe Ala Ala Lys Gln Gly His Gly Lys Ile
        355                 360                 365

Glu His Leu Lys Thr Pro Glu Gln Asn Val Glu Leu Ala Ala Ala Glu
    370                 375                 380

Leu Lys Ala Asp Glu Lys Ser His Ala Val Ile Leu Gly Asp Thr Arg
385                 390                 395                 400

Tyr Gly Ser Glu Glu Lys Gly Thr Tyr His Leu Ala Leu Phe Gly Asp
                405                 410                 415

Arg Ala Gln Glu Ile Ala Gly Ser Ala Thr Val Lys Ile Gly Glu Lys
            420                 425                 430

Val His Glu Ile Gly Ile Ala Gly Lys Gln Leu Glu Gly Gly Gly Gly
        435                 440                 445

Val Ala Ala Asp Ile Gly Ala Gly Leu Ala Asp Ala Leu Thr Ala Pro
    450                 455                 460

Leu Asp His Lys Asp Lys Gly Leu Gln Ser Leu Thr Leu Asp Gln Ser
465                 470                 475                 480

Val Arg Lys Asn Glu Lys Leu Lys Leu Ala Ala Gln Gly Ala Glu Lys
                485                 490                 495

Thr Tyr Gly Asn Gly Asp Ser Leu Asn Thr Gly Lys Leu Lys Asn Asp
            500                 505                 510

Lys Val Ser Arg Phe Asp Phe Ile Arg Gln Ile Glu Val Asp Gly Gln
        515                 520                 525

Leu Ile Thr Leu Glu Ser Gly Glu Phe Gln Val Tyr Lys Gln Ser His
    530                 535                 540

Ser Ala Leu Thr Ala Phe Gln Thr Glu Gln Ile Gln Asp Ser Glu His
545                 550                 555                 560

Ser Gly Lys Met Val Ala Lys Arg Gln Phe Arg Ile Gly Asp Ile Ala
                565                 570                 575

Gly Glu His Thr Ser Phe Asp Lys Leu Pro Glu Gly Gly Arg Ala Thr
            580                 585                 590

Tyr Arg Gly Thr Ala Phe Gly Ser Asp Asp Ala Gly Gly Lys Leu Thr
        595                 600                 605

Tyr Thr Ile Asp Phe Ala Ala Lys Gln Gly Asn Gly Lys Ile Glu His
    610                 615                 620

Leu Lys Ser Pro Glu Leu Asn Val Asp Leu Ala Ala Ala Asp Ile Lys
```

```
625                 630                 635                 640

Pro Asp Gly Lys Arg His Ala Val Ile Ser Gly Ser Val Leu Tyr Asn
                645                 650                 655

Gln Ala Glu Lys Gly Ser Tyr Ser Leu Gly Ile Phe Gly Gly Lys Ala
            660                 665                 670

Gln Glu Val Ala Gly Ser Ala Glu Val Lys Thr Val Asn Gly Ile Arg
        675                 680                 685

His Ile Gly Leu Ala Ala Lys Gln Leu Glu His His His His His His
    690                 695                 700


<210> SEQ ID NO 30
<211> LENGTH: 784
<212> TYPE: PRT
<213> ORGANISM: Neisseria meningitidis

<400> SEQUENCE: 30

Met Gly Pro Asp Ser Asp Arg Leu Gln Gln Arg Arg Val Ala Ala Asp
1               5                   10                  15

Ile Gly Ala Gly Leu Ala Asp Ala Leu Thr Ala Pro Leu Asp His Lys
            20                  25                  30

Asp Lys Ser Leu Gln Ser Leu Thr Leu Asp Gln Ser Val Arg Lys Asn
        35                  40                  45

Glu Lys Leu Lys Leu Ala Ala Gln Gly Ala Glu Lys Thr Tyr Gly Asn
    50                  55                  60

Gly Asp Ser Leu Asn Thr Gly Lys Leu Lys Asn Asp Lys Val Ser Arg
65                  70                  75                  80

Phe Asp Phe Ile Arg Gln Ile Glu Val Asp Gly Gln Leu Ile Thr Leu
                85                  90                  95

Glu Ser Gly Glu Phe Gln Ile Tyr Lys Gln Asp His Ser Ala Val Val
            100                 105                 110

Ala Leu Gln Ile Glu Lys Ile Asn Asn Pro Asp Lys Ile Asp Ser Leu
        115                 120                 125

Ile Asn Gln Arg Ser Phe Leu Val Ser Gly Leu Gly Gly Glu His Thr
    130                 135                 140

Ala Phe Asn Gln Leu Pro Asp Gly Lys Ala Glu Tyr His Gly Lys Ala
145                 150                 155                 160

Phe Ser Ser Asp Asp Ala Gly Gly Lys Leu Thr Tyr Thr Ile Asp Phe
                165                 170                 175

Ala Ala Lys Gln Gly His Gly Lys Ile Glu His Leu Lys Thr Pro Glu
            180                 185                 190

Gln Asn Val Glu Leu Ala Ala Ala Glu Leu Lys Ala Asp Glu Lys Ser
        195                 200                 205

His Ala Val Ile Leu Gly Asp Thr Arg Tyr Gly Ser Glu Glu Lys Gly
    210                 215                 220

Thr Tyr His Leu Ala Leu Phe Gly Asp Arg Ala Gln Glu Ile Ala Gly
225                 230                 235                 240

Ser Ala Thr Val Lys Ile Gly Glu Lys Val His Glu Ile Gly Ile Ala
                245                 250                 255

Gly Lys Gln Gly Ser Gly Gly Gly Gly Val Ala Ala Asp Ile Gly Ala
            260                 265                 270

Gly Leu Ala Asp Ala Leu Thr Ala Pro Leu Asp His Lys Asp Lys Gly
        275                 280                 285

Leu Gln Ser Leu Thr Leu Asp Gln Ser Val Arg Lys Asn Glu Lys Leu
    290                 295                 300

Lys Leu Ala Ala Gln Gly Ala Glu Lys Thr Tyr Gly Asn Gly Asp Ser
```

-continued 305 310 315 320

Leu Asn Thr Gly Lys Leu Lys Asn Asp Lys Val Ser Arg Phe Asp Phe
325 330 335

Ile Arg Gln Ile Glu Val Asp Gly Gln Leu Ile Thr Leu Glu Ser Gly
340 345 350

Glu Phe Gln Val Tyr Lys Gln Ser His Ser Ala Leu Thr Ala Phe Gln
355 360 365

Thr Glu Gln Ile Gln Asp Ser Glu His Ser Gly Lys Met Val Ala Lys
370 375 380

Arg Gln Phe Arg Ile Gly Asp Ile Ala Gly Glu His Thr Ser Phe Asp
385 390 395 400

Lys Leu Pro Glu Gly Gly Arg Ala Thr Tyr Arg Gly Thr Ala Phe Gly
405 410 415

Ser Asp Asp Ala Gly Gly Lys Leu Thr Tyr Thr Ile Asp Phe Ala Ala
420 425 430

Lys Gln Gly Asn Gly Lys Ile Glu His Leu Lys Ser Pro Glu Leu Asn
435 440 445

Val Asp Leu Ala Ala Ala Asp Ile Lys Pro Asp Gly Lys Arg His Ala
450 455 460

Val Ile Ser Gly Ser Val Leu Tyr Asn Gln Ala Glu Lys Gly Ser Tyr
465 470 475 480

Ser Leu Gly Ile Phe Gly Gly Lys Ala Gln Glu Val Ala Gly Ser Ala
485 490 495

Glu Val Lys Thr Val Asn Gly Ile Arg His Ile Gly Leu Ala Ala Lys
500 505 510

Gln Gly Ser Gly Pro Asp Ser Asp Arg Leu Gln Gln Arg Arg Val Ala
515 520 525

Ala Asp Ile Gly Thr Gly Leu Ala Asp Ala Leu Thr Ala Pro Leu Asp
530 535 540

His Lys Asp Lys Gly Leu Lys Ser Leu Thr Leu Glu Asp Ser Ile Pro
545 550 555 560

Gln Asn Gly Thr Leu Thr Leu Ser Ala Gln Gly Ala Glu Lys Thr Phe
565 570 575

Lys Ala Gly Asp Lys Asp Asn Ser Leu Asn Thr Gly Lys Leu Lys Asn
580 585 590

Asp Lys Ile Ser Arg Phe Asp Phe Val Gln Lys Ile Glu Val Asp Gly
595 600 605

Gln Thr Ile Thr Leu Ala Ser Gly Glu Phe Gln Ile Tyr Lys Gln Asn
610 615 620

His Ser Ala Val Val Ala Leu Gln Ile Glu Lys Ile Asn Asn Pro Asp
625 630 635 640

Lys Thr Asp Ser Leu Ile Asn Gln Arg Ser Phe Leu Val Ser Gly Leu
645 650 655

Gly Gly Glu His Thr Ala Phe Asn Gln Leu Pro Gly Gly Lys Ala Glu
660 665 670

Tyr His Gly Lys Ala Phe Ser Ser Asp Asp Pro Asn Gly Arg Leu His
675 680 685

Tyr Ser Ile Asp Phe Thr Lys Lys Gln Gly Tyr Gly Arg Ile Glu His
690 695 700

Leu Lys Thr Leu Glu Gln Asn Val Glu Leu Ala Ala Ala Glu Leu Lys
705 710 715 720

Ala Asp Glu Lys Ser His Ala Val Ile Leu Gly Asp Thr Arg Tyr Gly
725 730 735

Ser Glu Glu Lys Gly Thr Tyr His Leu Ala Leu Phe Gly Asp Arg Ala
740 745 750

Gln Glu Ile Ala Gly Ser Ala Thr Val Lys Ile Gly Glu Lys Val His
755 760 765

Glu Ile Gly Ile Ala Gly Lys Gln Lys Leu His His His His His His
770 775 780

<210> SEQ ID NO 31
<211> LENGTH: 784
<212> TYPE: PRT
<213> ORGANISM: Neisseria meningitidis

<400> SEQUENCE: 31

Met Gly Pro Asp Ser Asp Arg Leu Gln Gln Arg Arg Val Ala Ala Asp
1 5 10 15

Ile Gly Ala Gly Leu Ala Asp Ala Leu Thr Ala Pro Leu Asp His Lys
20 25 30

Asp Lys Ser Leu Gln Ser Leu Thr Leu Asp Gln Ser Val Arg Lys Asn
35 40 45

Glu Lys Leu Lys Leu Ala Ala Gln Gly Ala Glu Lys Thr Tyr Gly Asn
50 55 60

Gly Asp Ser Leu Asn Thr Gly Lys Leu Lys Asn Asp Lys Val Ser Arg
65 70 75 80

Phe Asp Phe Ile Arg Gln Ile Glu Val Asp Gly Gln Leu Ile Thr Leu
85 90 95

Glu Ser Gly Glu Phe Gln Ile Tyr Lys Gln Asp His Ser Ala Val Val
100 105 110

Ala Leu Gln Ile Glu Lys Ile Asn Asn Pro Asp Lys Ile Asp Ser Leu
115 120 125

Ile Asn Gln Arg Ser Phe Leu Val Ser Gly Leu Gly Gly Glu His Thr
130 135 140

Ala Phe Asn Gln Leu Pro Asp Gly Lys Ala Glu Tyr His Gly Lys Ala
145 150 155 160

Phe Ser Ser Asp Asp Ala Gly Gly Lys Leu Thr Tyr Thr Ile Asp Phe
165 170 175

Ala Ala Lys Gln Gly His Gly Lys Ile Glu His Leu Lys Thr Pro Glu
180 185 190

Gln Asn Val Glu Leu Ala Ala Ala Glu Leu Lys Ala Asp Glu Lys Ser
195 200 205

His Ala Val Ile Leu Gly Asp Thr Arg Tyr Gly Ser Glu Glu Lys Gly
210 215 220

Thr Tyr His Leu Ala Leu Phe Gly Asp Arg Ala Gln Glu Ile Ala Gly
225 230 235 240

Ser Ala Thr Val Lys Ile Gly Glu Lys Val His Glu Ile Gly Ile Ala
245 250 255

Gly Lys Gln Gly Ser Gly Pro Asp Ser Asp Arg Leu Gln Gln Arg Arg
260 265 270

Val Ala Ala Asp Ile Gly Thr Gly Leu Ala Asp Ala Leu Thr Ala Pro
275 280 285

Leu Asp His Lys Asp Lys Gly Leu Lys Ser Leu Thr Leu Glu Asp Ser
290 295 300

Ile Pro Gln Asn Gly Thr Leu Thr Leu Ser Ala Gln Gly Ala Glu Lys
305 310 315 320

Thr Phe Lys Ala Gly Asp Lys Asp Asn Ser Leu Asn Thr Gly Lys Leu
325 330 335

-continued

```
Lys Asn Asp Lys Ile Ser Arg Phe Asp Phe Val Gln Lys Ile Glu Val
            340                 345                 350

Asp Gly Gln Thr Ile Thr Leu Ala Ser Gly Glu Phe Gln Ile Tyr Lys
        355                 360                 365

Gln Asn His Ser Ala Val Val Ala Leu Gln Ile Glu Lys Ile Asn Asn
    370                 375                 380

Pro Asp Lys Thr Asp Ser Leu Ile Asn Gln Arg Ser Phe Leu Val Ser
385                 390                 395                 400

Gly Leu Gly Gly Glu His Thr Ala Phe Asn Gln Leu Pro Gly Gly Lys
                405                 410                 415

Ala Glu Tyr His Gly Lys Ala Phe Ser Ser Asp Asp Pro Asn Gly Arg
            420                 425                 430

Leu His Tyr Ser Ile Asp Phe Thr Lys Lys Gln Gly Tyr Gly Arg Ile
        435                 440                 445

Glu His Leu Lys Thr Leu Glu Gln Asn Val Glu Leu Ala Ala Ala Glu
    450                 455                 460

Leu Lys Ala Asp Glu Lys Ser His Ala Val Ile Leu Gly Asp Thr Arg
465                 470                 475                 480

Tyr Gly Ser Glu Glu Lys Gly Thr Tyr His Leu Ala Leu Phe Gly Asp
                485                 490                 495

Arg Ala Gln Glu Ile Ala Gly Ser Ala Thr Val Lys Ile Gly Glu Lys
            500                 505                 510

Val His Glu Ile Gly Ile Ala Gly Lys Gln Gly Ser Gly Gly Gly Gly
        515                 520                 525

Val Ala Ala Asp Ile Gly Ala Gly Leu Ala Asp Ala Leu Thr Ala Pro
    530                 535                 540

Leu Asp His Lys Asp Lys Gly Leu Gln Ser Leu Thr Leu Asp Gln Ser
545                 550                 555                 560

Val Arg Lys Asn Glu Lys Leu Lys Leu Ala Ala Gln Gly Ala Glu Lys
                565                 570                 575

Thr Tyr Gly Asn Gly Asp Ser Leu Asn Thr Gly Lys Leu Lys Asn Asp
            580                 585                 590

Lys Val Ser Arg Phe Asp Phe Ile Arg Gln Ile Glu Val Asp Gly Gln
        595                 600                 605

Leu Ile Thr Leu Glu Ser Gly Glu Phe Gln Val Tyr Lys Gln Ser His
    610                 615                 620

Ser Ala Leu Thr Ala Phe Gln Thr Glu Gln Ile Gln Asp Ser Glu His
625                 630                 635                 640

Ser Gly Lys Met Val Ala Lys Arg Gln Phe Arg Ile Gly Asp Ile Ala
                645                 650                 655

Gly Glu His Thr Ser Phe Asp Lys Leu Pro Glu Gly Gly Arg Ala Thr
            660                 665                 670

Tyr Arg Gly Thr Ala Phe Gly Ser Asp Asp Ala Gly Gly Lys Leu Thr
        675                 680                 685

Tyr Thr Ile Asp Phe Ala Ala Lys Gln Gly Asn Gly Lys Ile Glu His
    690                 695                 700

Leu Lys Ser Pro Glu Leu Asn Val Asp Leu Ala Ala Ala Asp Ile Lys
705                 710                 715                 720

Pro Asp Gly Lys Arg His Ala Val Ile Ser Gly Ser Val Leu Tyr Asn
                725                 730                 735

Gln Ala Glu Lys Gly Ser Tyr Ser Leu Gly Ile Phe Gly Gly Lys Ala
            740                 745                 750

Gln Glu Val Ala Gly Ser Ala Glu Val Lys Thr Val Asn Gly Ile Arg
        755                 760                 765
```

```
His Ile Gly Leu Ala Ala Lys Gln Leu Glu His His His His His His
    770                 775                 780


<210> SEQ ID NO 32
<211> LENGTH: 780
<212> TYPE: PRT
<213> ORGANISM: Neisseria meningitidis

<400> SEQUENCE: 32

Met Val Ala Ala Asp Ile Gly Ala Gly Leu Ala Asp Ala Leu Thr Ala
1               5                   10                  15

Pro Leu Asp His Lys Asp Lys Gly Leu Gln Ser Leu Thr Leu Asp Gln
            20                  25                  30

Ser Val Arg Lys Asn Glu Lys Leu Lys Leu Ala Ala Gln Gly Ala Glu
        35                  40                  45

Lys Thr Tyr Gly Asn Gly Asp Ser Leu Asn Thr Gly Lys Leu Lys Asn
    50                  55                  60

Asp Lys Val Ser Arg Phe Asp Phe Ile Arg Gln Ile Glu Val Asp Gly
65                  70                  75                  80

Gln Leu Ile Thr Leu Glu Ser Gly Glu Phe Gln Val Tyr Lys Gln Ser
                85                  90                  95

His Ser Ala Leu Thr Ala Phe Gln Thr Glu Gln Ile Gln Asp Ser Glu
            100                 105                 110

His Ser Gly Lys Met Val Ala Lys Arg Gln Phe Arg Ile Gly Asp Ile
        115                 120                 125

Ala Gly Glu His Thr Ser Phe Asp Lys Leu Pro Glu Gly Gly Arg Ala
    130                 135                 140

Thr Tyr Arg Gly Thr Ala Phe Gly Ser Asp Asp Ala Gly Gly Lys Leu
145                 150                 155                 160

Thr Tyr Thr Ile Asp Phe Ala Ala Lys Gln Gly Asn Gly Lys Ile Glu
                165                 170                 175

His Leu Lys Ser Pro Glu Leu Asn Val Asp Leu Ala Ala Ala Asp Ile
            180                 185                 190

Lys Pro Asp Gly Lys Arg His Ala Val Ile Ser Gly Ser Val Leu Tyr
        195                 200                 205

Asn Gln Ala Glu Lys Gly Ser Tyr Ser Leu Gly Ile Phe Gly Gly Lys
    210                 215                 220

Ala Gln Glu Val Ala Gly Ser Ala Glu Val Lys Thr Val Asn Gly Ile
225                 230                 235                 240

Arg His Ile Gly Leu Ala Ala Lys Gln Gly Ser Gly Pro Asp Ser Asp
                245                 250                 255

Arg Leu Gln Gln Arg Arg Val Ala Ala Asp Ile Gly Ala Gly Leu Ala
            260                 265                 270

Asp Ala Leu Thr Ala Pro Leu Asp His Lys Asp Lys Ser Leu Gln Ser
        275                 280                 285

Leu Thr Leu Asp Gln Ser Val Arg Lys Asn Glu Lys Leu Lys Leu Ala
    290                 295                 300

Ala Gln Gly Ala Glu Lys Thr Tyr Gly Asn Gly Asp Ser Leu Asn Thr
305                 310                 315                 320

Gly Lys Leu Lys Asn Asp Lys Val Ser Arg Phe Asp Phe Ile Arg Gln
                325                 330                 335

Ile Glu Val Asp Gly Gln Leu Ile Thr Leu Glu Ser Gly Glu Phe Gln
            340                 345                 350

Ile Tyr Lys Gln Asp His Ser Ala Val Val Ala Leu Gln Ile Glu Lys
        355                 360                 365
```

-continued

```
Ile Asn Asn Pro Asp Lys Ile Asp Ser Leu Ile Asn Gln Arg Ser Phe
    370                 375                 380

Leu Val Ser Gly Leu Gly Gly Glu His Thr Ala Phe Asn Gln Leu Pro
385                 390                 395                 400

Asp Gly Lys Ala Glu Tyr His Gly Lys Ala Phe Ser Ser Asp Asp Ala
                405                 410                 415

Gly Gly Lys Leu Thr Tyr Thr Ile Asp Phe Ala Ala Lys Gln Gly His
            420                 425                 430

Gly Lys Ile Glu His Leu Lys Thr Pro Glu Gln Asn Val Glu Leu Ala
        435                 440                 445

Ala Ala Glu Leu Lys Ala Asp Glu Lys Ser His Ala Val Ile Leu Gly
    450                 455                 460

Asp Thr Arg Tyr Gly Ser Glu Glu Lys Gly Thr Tyr His Leu Ala Leu
465                 470                 475                 480

Phe Gly Asp Arg Ala Gln Glu Ile Ala Gly Ser Ala Thr Val Lys Ile
                485                 490                 495

Gly Glu Lys Val His Glu Ile Gly Ile Ala Gly Lys Gln Gly Ser Gly
            500                 505                 510

Pro Asp Ser Asp Arg Leu Gln Gln Arg Arg Val Ala Ala Asp Ile Gly
        515                 520                 525

Thr Gly Leu Ala Asp Ala Leu Thr Ala Pro Leu Asp His Lys Asp Lys
    530                 535                 540

Gly Leu Lys Ser Leu Thr Leu Glu Asp Ser Ile Pro Gln Asn Gly Thr
545                 550                 555                 560

Leu Thr Leu Ser Ala Gln Gly Ala Glu Lys Thr Phe Lys Ala Gly Asp
                565                 570                 575

Lys Asp Asn Ser Leu Asn Thr Gly Lys Leu Lys Asn Asp Lys Ile Ser
            580                 585                 590

Arg Phe Asp Phe Val Gln Lys Ile Glu Val Asp Gly Gln Thr Ile Thr
        595                 600                 605

Leu Ala Ser Gly Glu Phe Gln Ile Tyr Lys Gln Asn His Ser Ala Val
    610                 615                 620

Val Ala Leu Gln Ile Glu Lys Ile Asn Asn Pro Asp Lys Thr Asp Ser
625                 630                 635                 640

Leu Ile Asn Gln Arg Ser Phe Leu Val Ser Gly Leu Gly Gly Glu His
                645                 650                 655

Thr Ala Phe Asn Gln Leu Pro Gly Gly Lys Ala Glu Tyr His Gly Lys
            660                 665                 670

Ala Phe Ser Ser Asp Asp Pro Asn Gly Arg Leu His Tyr Ser Ile Asp
        675                 680                 685

Phe Thr Lys Lys Gln Gly Tyr Gly Arg Ile Glu His Leu Lys Thr Leu
    690                 695                 700

Glu Gln Asn Val Glu Leu Ala Ala Ala Glu Leu Lys Ala Asp Glu Lys
705                 710                 715                 720

Ser His Ala Val Ile Leu Gly Asp Thr Arg Tyr Gly Ser Glu Glu Lys
                725                 730                 735

Gly Thr Tyr His Leu Ala Leu Phe Gly Asp Arg Ala Gln Glu Ile Ala
            740                 745                 750

Gly Ser Ala Thr Val Lys Ile Gly Glu Lys Val His Glu Ile Gly Ile
        755                 760                 765

Ala Gly Lys Gln Lys Leu His His His His His His
    770                 775                 780
```

<210> SEQ ID NO 33
<211> LENGTH: 513
<212> TYPE: PRT
<213> ORGANISM: Neisseria meningitidis

<400> SEQUENCE: 33

```
Met Gly Pro Asp Ser Asp Arg Leu Gln Gln Arg Arg Val Ala Ala Asp
1               5                   10                  15

Ile Gly Ala Gly Leu Ala Asp Ala Leu Thr Ala Pro Leu Asp His Lys
            20                  25                  30

Asp Lys Ser Leu Gln Ser Leu Thr Leu Asp Gln Ser Val Arg Lys Asn
        35                  40                  45

Glu Lys Leu Lys Leu Ala Ala Gln Gly Ala Glu Lys Thr Tyr Gly Asn
    50                  55                  60

Gly Asp Ser Leu Asn Thr Gly Lys Leu Lys Asn Asp Lys Val Ser Arg
65                  70                  75                  80

Phe Asp Phe Ile Arg Gln Ile Glu Val Asp Gly Gln Leu Ile Thr Leu
                85                  90                  95

Glu Ser Gly Glu Phe Gln Ile Tyr Lys Gln Asp His Ser Ala Val Val
            100                 105                 110

Ala Leu Gln Ile Glu Lys Ile Asn Asn Pro Asp Lys Ile Asp Ser Leu
        115                 120                 125

Ile Asn Gln Arg Ser Phe Leu Val Ser Gly Leu Gly Gly Glu His Thr
    130                 135                 140

Ala Phe Asn Gln Leu Pro Asp Gly Lys Ala Glu Tyr His Gly Lys Ala
145                 150                 155                 160

Phe Ser Ser Asp Asp Ala Gly Gly Lys Leu Thr Tyr Thr Ile Asp Phe
                165                 170                 175

Ala Ala Lys Gln Gly His Gly Lys Ile Glu His Leu Lys Thr Pro Glu
            180                 185                 190

Gln Asn Val Glu Leu Ala Ala Ala Glu Leu Lys Ala Asp Glu Lys Ser
        195                 200                 205

His Ala Val Ile Leu Gly Asp Thr Arg Tyr Gly Ser Glu Glu Lys Gly
    210                 215                 220

Thr Tyr His Leu Ala Leu Phe Gly Asp Arg Ala Gln Glu Ile Ala Gly
225                 230                 235                 240

Ser Ala Thr Val Lys Ile Gly Glu Lys Val His Glu Ile Gly Ile Ala
                245                 250                 255

Gly Lys Gln Gly Ser Gly Gly Gly Gly Val Ala Ala Asp Ile Gly Ala
            260                 265                 270

Gly Leu Ala Asp Ala Leu Thr Ala Pro Leu Asp His Lys Asp Lys Gly
        275                 280                 285

Leu Gln Ser Leu Thr Leu Asp Gln Ser Val Arg Lys Asn Glu Lys Leu
    290                 295                 300

Lys Leu Ala Ala Gln Gly Ala Glu Lys Thr Tyr Gly Asn Gly Asp Ser
305                 310                 315                 320

Leu Asn Thr Gly Lys Leu Lys Asn Asp Lys Val Ser Arg Phe Asp Phe
                325                 330                 335

Ile Arg Gln Ile Glu Val Asp Gly Gln Leu Ile Thr Leu Glu Ser Gly
            340                 345                 350

Glu Phe Gln Val Tyr Lys Gln Ser His Ser Ala Leu Thr Ala Phe Gln
        355                 360                 365

Thr Glu Gln Ile Gln Asp Ser Glu His Ser Gly Lys Met Val Ala Lys
    370                 375                 380

Arg Gln Phe Arg Ile Gly Asp Ile Ala Gly Glu His Thr Ser Phe Asp
```

```
385                 390                 395                 400

Lys Leu Pro Glu Gly Gly Arg Ala Thr Tyr Arg Gly Thr Ala Phe Gly
                405                 410                 415

Ser Asp Asp Ala Gly Gly Lys Leu Thr Tyr Thr Ile Asp Phe Ala Ala
            420                 425                 430

Lys Gln Gly Asn Gly Lys Ile Glu His Leu Lys Ser Pro Glu Leu Asn
        435                 440                 445

Val Asp Leu Ala Ala Ala Asp Ile Lys Pro Asp Gly Lys Arg His Ala
    450                 455                 460

Val Ile Ser Gly Ser Val Leu Tyr Asn Gln Ala Glu Lys Gly Ser Tyr
465                 470                 475                 480

Ser Leu Gly Ile Phe Gly Gly Lys Ala Gln Glu Val Ala Gly Ser Ala
                485                 490                 495

Glu Val Lys Thr Val Asn Gly Ile Arg His Ile Gly Leu Ala Ala Lys
            500                 505                 510

Gln


<210> SEQ ID NO 34
<211> LENGTH: 696
<212> TYPE: PRT
<213> ORGANISM: Neisseria meningitidis

<400> SEQUENCE: 34

Met Ala Ser Val Ser Ala Val Ile Gly Ser Ala Ala Val Gly Ala Lys
1               5                   10                  15

Ser Ala Val Asp Arg Arg Thr Thr Gly Ala Gln Thr Asp Asp Asn Val
            20                  25                  30

Met Ala Leu Arg Ile Glu Thr Thr Ala Arg Ser Tyr Leu Arg Gln Asn
        35                  40                  45

Asn Gln Thr Lys Gly Tyr Thr Pro Gln Ile Ser Val Val Gly Tyr Asn
    50                  55                  60

Arg His Leu Leu Leu Leu Gly Gln Val Ala Thr Glu Gly Glu Lys Gln
65                  70                  75                  80

Phe Val Gly Gln Ile Ala Arg Ser Glu Gln Ala Ala Glu Gly Val Tyr
                85                  90                  95

Asn Tyr Ile Thr Val Ala Ser Leu Pro Arg Thr Ala Gly Asp Ile Ala
            100                 105                 110

Gly Asp Thr Trp Asn Thr Ser Lys Val Arg Ala Thr Leu Leu Gly Ile
        115                 120                 125

Ser Pro Ala Thr Gln Ala Arg Val Lys Ile Val Thr Tyr Gly Asn Val
    130                 135                 140

Thr Tyr Val Met Gly Ile Leu Thr Pro Glu Glu Gln Ala Gln Ile Thr
145                 150                 155                 160

Gln Lys Val Ser Thr Thr Val Gly Val Gln Lys Val Ile Thr Leu Tyr
                165                 170                 175

Gln Asn Tyr Val Gln Arg Gly Ser Gly Gly Gly Gly Val Ala Ala Asp
            180                 185                 190

Ile Gly Ala Gly Leu Ala Asp Ala Leu Thr Ala Pro Leu Asp His Lys
        195                 200                 205

Asp Lys Gly Leu Gln Ser Leu Thr Leu Asp Gln Ser Val Arg Lys Asn
    210                 215                 220

Glu Lys Leu Lys Leu Ala Ala Gln Gly Ala Glu Lys Thr Tyr Gly Asn
225                 230                 235                 240

Gly Asp Ser Leu Asn Thr Gly Lys Leu Lys Asn Asp Lys Val Ser Arg
                245                 250                 255
```

-continued

```
Phe Asp Phe Ile Arg Gln Ile Glu Val Asp Gly Gln Leu Ile Thr Leu
            260                 265                 270

Glu Ser Gly Glu Phe Gln Val Tyr Lys Gln Ser His Ser Ala Leu Thr
        275                 280                 285

Ala Phe Gln Thr Glu Gln Ile Gln Asp Ser Glu His Ser Gly Lys Met
    290                 295                 300

Val Ala Lys Arg Gln Phe Arg Ile Gly Asp Ile Ala Gly Glu His Thr
305                 310                 315                 320

Ser Phe Asp Lys Leu Pro Glu Gly Gly Arg Ala Thr Tyr Arg Gly Thr
                325                 330                 335

Ala Phe Gly Ser Asp Asp Ala Gly Gly Lys Leu Thr Tyr Thr Ile Asp
            340                 345                 350

Phe Ala Ala Lys Gln Gly Asn Gly Lys Ile Glu His Leu Lys Ser Pro
        355                 360                 365

Glu Leu Asn Val Asp Leu Ala Ala Ala Asp Ile Lys Pro Asp Gly Lys
    370                 375                 380

Arg His Ala Val Ile Ser Gly Ser Val Leu Tyr Asn Gln Ala Glu Lys
385                 390                 395                 400

Gly Ser Tyr Ser Leu Gly Ile Phe Gly Gly Lys Ala Gln Glu Val Ala
                405                 410                 415

Gly Ser Ala Glu Val Lys Thr Val Asn Gly Ile Arg His Ile Gly Leu
            420                 425                 430

Ala Ala Lys Gln Gly Ser Gly Pro Asp Ser Asp Arg Leu Gln Gln Arg
        435                 440                 445

Arg Val Ala Ala Asp Ile Gly Ala Gly Leu Ala Asp Ala Leu Thr Ala
    450                 455                 460

Pro Leu Asp His Lys Asp Lys Ser Leu Gln Ser Leu Thr Leu Asp Gln
465                 470                 475                 480

Ser Val Arg Lys Asn Glu Lys Leu Lys Leu Ala Ala Gln Gly Ala Glu
                485                 490                 495

Lys Thr Tyr Gly Asn Gly Asp Ser Leu Asn Thr Gly Lys Leu Lys Asn
            500                 505                 510

Asp Lys Val Ser Arg Phe Asp Phe Ile Arg Gln Ile Glu Val Asp Gly
        515                 520                 525

Gln Leu Ile Thr Leu Glu Ser Gly Glu Phe Gln Ile Tyr Lys Gln Asp
    530                 535                 540

His Ser Ala Val Val Ala Leu Gln Ile Glu Lys Ile Asn Asn Pro Asp
545                 550                 555                 560

Lys Ile Asp Ser Leu Ile Asn Gln Arg Ser Phe Leu Val Ser Gly Leu
                565                 570                 575

Gly Gly Glu His Thr Ala Phe Asn Gln Leu Pro Asp Gly Lys Ala Glu
            580                 585                 590

Tyr His Gly Lys Ala Phe Ser Ser Asp Asp Ala Gly Gly Lys Leu Thr
        595                 600                 605

Tyr Thr Ile Asp Phe Ala Ala Lys Gln Gly His Gly Lys Ile Glu His
    610                 615                 620

Leu Lys Thr Pro Glu Gln Asn Val Glu Leu Ala Ala Ala Glu Leu Lys
625                 630                 635                 640

Ala Asp Glu Lys Ser His Ala Val Ile Leu Gly Asp Thr Arg Tyr Gly
                645                 650                 655

Ser Glu Glu Lys Gly Thr Tyr His Leu Ala Leu Phe Gly Asp Arg Ala
            660                 665                 670

Gln Glu Ile Ala Gly Ser Ala Thr Val Lys Ile Gly Glu Lys Val His
```

```
        675                 680                 685

Glu Ile Gly Ile Ala Gly Lys Gln
    690                 695


<210> SEQ ID NO 35
<211> LENGTH: 696
<212> TYPE: PRT
<213> ORGANISM: Neisseria meningitidis

<400> SEQUENCE: 35

Met Ala Ser Val Ser Ala Val Ile Gly Ser Ala Ala Val Gly Ala Lys
1               5                   10                  15

Ser Ala Val Asp Arg Arg Thr Thr Gly Ala Gln Thr Asp Asp Asn Val
            20                  25                  30

Met Ala Leu Arg Ile Glu Thr Thr Ala Arg Ser Tyr Leu Arg Gln Asn
        35                  40                  45

Asn Gln Thr Lys Gly Tyr Thr Pro Gln Ile Ser Val Val Gly Tyr Asn
    50                  55                  60

Arg His Leu Leu Leu Leu Gly Gln Val Ala Thr Glu Gly Glu Lys Gln
65                  70                  75                  80

Phe Val Gly Gln Ile Ala Arg Ser Glu Gln Ala Ala Glu Gly Val Tyr
                85                  90                  95

Asn Tyr Ile Thr Val Ala Ser Leu Pro Arg Thr Ala Gly Asp Ile Ala
            100                 105                 110

Gly Asp Thr Trp Asn Thr Ser Lys Val Arg Ala Thr Leu Leu Gly Ile
        115                 120                 125

Ser Pro Ala Thr Gln Ala Arg Val Lys Ile Val Thr Tyr Gly Asn Val
    130                 135                 140

Thr Tyr Val Met Gly Ile Leu Thr Pro Glu Glu Gln Ala Gln Ile Thr
145                 150                 155                 160

Gln Lys Val Ser Thr Thr Val Gly Val Gln Lys Val Ile Thr Leu Tyr
                165                 170                 175

Gln Asn Tyr Val Gln Arg Gly Ser Gly Pro Asp Ser Asp Arg Leu Gln
            180                 185                 190

Gln Arg Arg Val Ala Ala Asp Ile Gly Ala Gly Leu Ala Asp Ala Leu
        195                 200                 205

Thr Ala Pro Leu Asp His Lys Asp Lys Ser Leu Gln Ser Leu Thr Leu
    210                 215                 220

Asp Gln Ser Val Arg Lys Asn Glu Lys Leu Lys Leu Ala Ala Gln Gly
225                 230                 235                 240

Ala Glu Lys Thr Tyr Gly Asn Gly Asp Ser Leu Asn Thr Gly Lys Leu
                245                 250                 255

Lys Asn Asp Lys Val Ser Arg Phe Asp Phe Ile Arg Gln Ile Glu Val
            260                 265                 270

Asp Gly Gln Leu Ile Thr Leu Glu Ser Gly Glu Phe Gln Ile Tyr Lys
        275                 280                 285

Gln Asp His Ser Ala Val Val Ala Leu Gln Ile Glu Lys Ile Asn Asn
    290                 295                 300

Pro Asp Lys Ile Asp Ser Leu Ile Asn Gln Arg Ser Phe Leu Val Ser
305                 310                 315                 320

Gly Leu Gly Gly Glu His Thr Ala Phe Asn Gln Leu Pro Asp Gly Lys
                325                 330                 335

Ala Glu Tyr His Gly Lys Ala Phe Ser Ser Asp Asp Ala Gly Gly Lys
            340                 345                 350

Leu Thr Tyr Thr Ile Asp Phe Ala Ala Lys Gln Gly His Gly Lys Ile
```

```
        355                 360                 365

Glu His Leu Lys Thr Pro Glu Gln Asn Val Glu Leu Ala Ala Ala Glu
    370                 375                 380

Leu Lys Ala Asp Glu Lys Ser His Ala Val Ile Leu Gly Asp Thr Arg
385                 390                 395                 400

Tyr Gly Ser Glu Glu Lys Gly Thr Tyr His Leu Ala Leu Phe Gly Asp
                405                 410                 415

Arg Ala Gln Glu Ile Ala Gly Ser Ala Thr Val Lys Ile Gly Glu Lys
            420                 425                 430

Val His Glu Ile Gly Ile Ala Gly Lys Gln Gly Ser Gly Gly Gly Gly
        435                 440                 445

Val Ala Ala Asp Ile Gly Ala Gly Leu Ala Asp Ala Leu Thr Ala Pro
    450                 455                 460

Leu Asp His Lys Asp Lys Gly Leu Gln Ser Leu Thr Leu Asp Gln Ser
465                 470                 475                 480

Val Arg Lys Asn Glu Lys Leu Lys Leu Ala Ala Gln Gly Ala Glu Lys
                485                 490                 495

Thr Tyr Gly Asn Gly Asp Ser Leu Asn Thr Gly Lys Leu Lys Asn Asp
            500                 505                 510

Lys Val Ser Arg Phe Asp Phe Ile Arg Gln Ile Glu Val Asp Gly Gln
        515                 520                 525

Leu Ile Thr Leu Glu Ser Gly Glu Phe Gln Val Tyr Lys Gln Ser His
    530                 535                 540

Ser Ala Leu Thr Ala Phe Gln Thr Glu Gln Ile Gln Asp Ser Glu His
545                 550                 555                 560

Ser Gly Lys Met Val Ala Lys Arg Gln Phe Arg Ile Gly Asp Ile Ala
                565                 570                 575

Gly Glu His Thr Ser Phe Asp Lys Leu Pro Glu Gly Gly Arg Ala Thr
            580                 585                 590

Tyr Arg Gly Thr Ala Phe Gly Ser Asp Asp Ala Gly Gly Lys Leu Thr
        595                 600                 605

Tyr Thr Ile Asp Phe Ala Ala Lys Gln Gly Asn Gly Lys Ile Glu His
    610                 615                 620

Leu Lys Ser Pro Glu Leu Asn Val Asp Leu Ala Ala Ala Asp Ile Lys
625                 630                 635                 640

Pro Asp Gly Lys Arg His Ala Val Ile Ser Gly Ser Val Leu Tyr Asn
                645                 650                 655

Gln Ala Glu Lys Gly Ser Tyr Ser Leu Gly Ile Phe Gly Gly Lys Ala
            660                 665                 670

Gln Glu Val Ala Gly Ser Ala Glu Val Lys Thr Val Asn Gly Ile Arg
        675                 680                 685

His Ile Gly Leu Ala Ala Lys Gln
    690                 695


<210> SEQ ID NO 36
<211> LENGTH: 776
<212> TYPE: PRT
<213> ORGANISM: Neisseria meningitidis

<400> SEQUENCE: 36

Met Gly Pro Asp Ser Asp Arg Leu Gln Gln Arg Arg Val Ala Ala Asp
1               5                   10                  15

Ile Gly Ala Gly Leu Ala Asp Ala Leu Thr Ala Pro Leu Asp His Lys
            20                  25                  30

Asp Lys Ser Leu Gln Ser Leu Thr Leu Asp Gln Ser Val Arg Lys Asn
```

-continued

```
        35                  40                  45

Glu Lys Leu Lys Leu Ala Ala Gln Gly Ala Glu Lys Thr Tyr Gly Asn
    50                  55                  60

Gly Asp Ser Leu Asn Thr Gly Lys Leu Lys Asn Asp Lys Val Ser Arg
65                  70                  75                  80

Phe Asp Phe Ile Arg Gln Ile Glu Val Asp Gly Gln Leu Ile Thr Leu
                85                  90                  95

Glu Ser Gly Glu Phe Gln Ile Tyr Lys Gln Asp His Ser Ala Val Val
            100                 105                 110

Ala Leu Gln Ile Glu Lys Ile Asn Asn Pro Asp Lys Ile Asp Ser Leu
        115                 120                 125

Ile Asn Gln Arg Ser Phe Leu Val Ser Gly Leu Gly Gly Glu His Thr
    130                 135                 140

Ala Phe Asn Gln Leu Pro Asp Gly Lys Ala Glu Tyr His Gly Lys Ala
145                 150                 155                 160

Phe Ser Ser Asp Asp Ala Gly Gly Lys Leu Thr Tyr Thr Ile Asp Phe
                165                 170                 175

Ala Ala Lys Gln Gly His Gly Lys Ile Glu His Leu Lys Thr Pro Glu
            180                 185                 190

Gln Asn Val Glu Leu Ala Ala Ala Glu Leu Lys Ala Asp Glu Lys Ser
        195                 200                 205

His Ala Val Ile Leu Gly Asp Thr Arg Tyr Gly Ser Glu Glu Lys Gly
    210                 215                 220

Thr Tyr His Leu Ala Leu Phe Gly Asp Arg Ala Gln Glu Ile Ala Gly
225                 230                 235                 240

Ser Ala Thr Val Lys Ile Gly Glu Lys Val His Glu Ile Gly Ile Ala
                245                 250                 255

Gly Lys Gln Gly Ser Gly Pro Asp Ser Asp Arg Leu Gln Gln Arg Arg
            260                 265                 270

Val Ala Ala Asp Ile Gly Thr Gly Leu Ala Asp Ala Leu Thr Ala Pro
        275                 280                 285

Leu Asp His Lys Asp Lys Gly Leu Lys Ser Leu Thr Leu Glu Asp Ser
    290                 295                 300

Ile Pro Gln Asn Gly Thr Leu Thr Leu Ser Ala Gln Gly Ala Glu Lys
305                 310                 315                 320

Thr Phe Lys Ala Gly Asp Lys Asp Asn Ser Leu Asn Thr Gly Lys Leu
                325                 330                 335

Lys Asn Asp Lys Ile Ser Arg Phe Asp Phe Val Gln Lys Ile Glu Val
            340                 345                 350

Asp Gly Gln Thr Ile Thr Leu Ala Ser Gly Glu Phe Gln Ile Tyr Lys
        355                 360                 365

Gln Asn His Ser Ala Val Val Ala Leu Gln Ile Glu Lys Ile Asn Asn
    370                 375                 380

Pro Asp Lys Thr Asp Ser Leu Ile Asn Gln Arg Ser Phe Leu Val Ser
385                 390                 395                 400

Gly Leu Gly Gly Glu His Thr Ala Phe Asn Gln Leu Pro Gly Gly Lys
                405                 410                 415

Ala Glu Tyr His Gly Lys Ala Phe Ser Ser Asp Asp Pro Asn Gly Arg
            420                 425                 430

Leu His Tyr Ser Ile Asp Phe Thr Lys Lys Gln Gly Tyr Gly Arg Ile
        435                 440                 445

Glu His Leu Lys Thr Leu Glu Gln Asn Val Glu Leu Ala Ala Ala Glu
    450                 455                 460
```

Leu Lys Ala Asp Glu Lys Ser His Ala Val Ile Leu Gly Asp Thr Arg
465 470 475 480

Tyr Gly Ser Glu Glu Lys Gly Thr Tyr His Leu Ala Leu Phe Gly Asp
485 490 495

Arg Ala Gln Glu Ile Ala Gly Ser Ala Thr Val Lys Ile Gly Glu Lys
500 505 510

Val His Glu Ile Gly Ile Ala Gly Lys Gln Gly Ser Gly Gly Gly Gly
515 520 525

Val Ala Ala Asp Ile Gly Ala Gly Leu Ala Asp Ala Leu Thr Ala Pro
530 535 540

Leu Asp His Lys Asp Lys Gly Leu Gln Ser Leu Thr Leu Asp Gln Ser
545 550 555 560

Val Arg Lys Asn Glu Lys Leu Lys Leu Ala Ala Gln Gly Ala Glu Lys
565 570 575

Thr Tyr Gly Asn Gly Asp Ser Leu Asn Thr Gly Lys Leu Lys Asn Asp
580 585 590

Lys Val Ser Arg Phe Asp Phe Ile Arg Gln Ile Glu Val Asp Gly Gln
595 600 605

Leu Ile Thr Leu Glu Ser Gly Glu Phe Gln Val Tyr Lys Gln Ser His
610 615 620

Ser Ala Leu Thr Ala Phe Gln Thr Glu Gln Ile Gln Asp Ser Glu His
625 630 635 640

Ser Gly Lys Met Val Ala Lys Arg Gln Phe Arg Ile Gly Asp Ile Ala
645 650 655

Gly Glu His Thr Ser Phe Asp Lys Leu Pro Glu Gly Gly Arg Ala Thr
660 665 670

Tyr Arg Gly Thr Ala Phe Gly Ser Asp Asp Ala Gly Gly Lys Leu Thr
675 680 685

Tyr Thr Ile Asp Phe Ala Ala Lys Gln Gly Asn Gly Lys Ile Glu His
690 695 700

Leu Lys Ser Pro Glu Leu Asn Val Asp Leu Ala Ala Ala Asp Ile Lys
705 710 715 720

Pro Asp Gly Lys Arg His Ala Val Ile Ser Gly Ser Val Leu Tyr Asn
725 730 735

Gln Ala Glu Lys Gly Ser Tyr Ser Leu Gly Ile Phe Gly Gly Lys Ala
740 745 750

Gln Glu Val Ala Gly Ser Ala Glu Val Lys Thr Val Asn Gly Ile Arg
755 760 765

His Ile Gly Leu Ala Ala Lys Gln
770 775

<210> SEQ ID NO 37
<211> LENGTH: 776
<212> TYPE: PRT
<213> ORGANISM: Neisseria meningitidis

<400> SEQUENCE: 37

Met Gly Pro Asp Ser Asp Arg Leu Gln Gln Arg Arg Val Ala Ala Asp
1 5 10 15

Ile Gly Ala Gly Leu Ala Asp Ala Leu Thr Ala Pro Leu Asp His Lys
20 25 30

Asp Lys Ser Leu Gln Ser Leu Thr Leu Asp Gln Ser Val Arg Lys Asn
35 40 45

Glu Lys Leu Lys Leu Ala Ala Gln Gly Ala Glu Lys Thr Tyr Gly Asn
50 55 60

```
Gly Asp Ser Leu Asn Thr Gly Lys Leu Lys Asn Asp Lys Val Ser Arg
65                  70                  75                  80

Phe Asp Phe Ile Arg Gln Ile Glu Val Asp Gly Gln Leu Ile Thr Leu
                85                  90                  95

Glu Ser Gly Glu Phe Gln Ile Tyr Lys Gln Asp His Ser Ala Val Val
            100                 105                 110

Ala Leu Gln Ile Glu Lys Ile Asn Asn Pro Asp Lys Ile Asp Ser Leu
        115                 120                 125

Ile Asn Gln Arg Ser Phe Leu Val Ser Gly Leu Gly Gly Glu His Thr
    130                 135                 140

Ala Phe Asn Gln Leu Pro Asp Gly Lys Ala Glu Tyr His Gly Lys Ala
145                 150                 155                 160

Phe Ser Ser Asp Asp Ala Gly Gly Lys Leu Thr Tyr Thr Ile Asp Phe
                165                 170                 175

Ala Ala Lys Gln Gly His Gly Lys Ile Glu His Leu Lys Thr Pro Glu
            180                 185                 190

Gln Asn Val Glu Leu Ala Ala Ala Glu Leu Lys Ala Asp Glu Lys Ser
        195                 200                 205

His Ala Val Ile Leu Gly Asp Thr Arg Tyr Gly Ser Glu Glu Lys Gly
    210                 215                 220

Thr Tyr His Leu Ala Leu Phe Gly Asp Arg Ala Gln Glu Ile Ala Gly
225                 230                 235                 240

Ser Ala Thr Val Lys Ile Gly Glu Lys Val His Glu Ile Gly Ile Ala
                245                 250                 255

Gly Lys Gln Gly Ser Gly Gly Gly Gly Val Ala Ala Asp Ile Gly Ala
            260                 265                 270

Gly Leu Ala Asp Ala Leu Thr Ala Pro Leu Asp His Lys Asp Lys Gly
        275                 280                 285

Leu Gln Ser Leu Thr Leu Asp Gln Ser Val Arg Lys Asn Glu Lys Leu
    290                 295                 300

Lys Leu Ala Ala Gln Gly Ala Glu Lys Thr Tyr Gly Asn Gly Asp Ser
305                 310                 315                 320

Leu Asn Thr Gly Lys Leu Lys Asn Asp Lys Val Ser Arg Phe Asp Phe
                325                 330                 335

Ile Arg Gln Ile Glu Val Asp Gly Gln Leu Ile Thr Leu Glu Ser Gly
            340                 345                 350

Glu Phe Gln Val Tyr Lys Gln Ser His Ser Ala Leu Thr Ala Phe Gln
        355                 360                 365

Thr Glu Gln Ile Gln Asp Ser Glu His Ser Gly Lys Met Val Ala Lys
    370                 375                 380

Arg Gln Phe Arg Ile Gly Asp Ile Ala Gly Glu His Thr Ser Phe Asp
385                 390                 395                 400

Lys Leu Pro Glu Gly Gly Arg Ala Thr Tyr Arg Gly Thr Ala Phe Gly
                405                 410                 415

Ser Asp Asp Ala Gly Gly Lys Leu Thr Tyr Thr Ile Asp Phe Ala Ala
            420                 425                 430

Lys Gln Gly Asn Gly Lys Ile Glu His Leu Lys Ser Pro Glu Leu Asn
        435                 440                 445

Val Asp Leu Ala Ala Ala Asp Ile Lys Pro Asp Gly Lys Arg His Ala
    450                 455                 460

Val Ile Ser Gly Ser Val Leu Tyr Asn Gln Ala Glu Lys Gly Ser Tyr
465                 470                 475                 480

Ser Leu Gly Ile Phe Gly Gly Lys Ala Gln Glu Val Ala Gly Ser Ala
                485                 490                 495
```

```
Glu Val Lys Thr Val Asn Gly Ile Arg His Ile Gly Leu Ala Ala Lys
            500                 505                 510

Gln Gly Ser Gly Pro Asp Ser Asp Arg Leu Gln Gln Arg Arg Val Ala
        515                 520                 525

Ala Asp Ile Gly Thr Gly Leu Ala Asp Ala Leu Thr Ala Pro Leu Asp
    530                 535                 540

His Lys Asp Lys Gly Leu Lys Ser Leu Thr Leu Glu Asp Ser Ile Pro
545                 550                 555                 560

Gln Asn Gly Thr Leu Thr Leu Ser Ala Gln Gly Ala Glu Lys Thr Phe
                565                 570                 575

Lys Ala Gly Asp Lys Asp Asn Ser Leu Asn Thr Gly Lys Leu Lys Asn
            580                 585                 590

Asp Lys Ile Ser Arg Phe Asp Phe Val Gln Lys Ile Glu Val Asp Gly
        595                 600                 605

Gln Thr Ile Thr Leu Ala Ser Gly Glu Phe Gln Ile Tyr Lys Gln Asn
    610                 615                 620

His Ser Ala Val Val Ala Leu Gln Ile Glu Lys Ile Asn Asn Pro Asp
625                 630                 635                 640

Lys Thr Asp Ser Leu Ile Asn Gln Arg Ser Phe Leu Val Ser Gly Leu
                645                 650                 655

Gly Gly Glu His Thr Ala Phe Asn Gln Leu Pro Gly Gly Lys Ala Glu
            660                 665                 670

Tyr His Gly Lys Ala Phe Ser Ser Asp Asp Pro Asn Gly Arg Leu His
        675                 680                 685

Tyr Ser Ile Asp Phe Thr Lys Lys Gln Gly Tyr Gly Arg Ile Glu His
    690                 695                 700

Leu Lys Thr Leu Glu Gln Asn Val Glu Leu Ala Ala Ala Glu Leu Lys
705                 710                 715                 720

Ala Asp Glu Lys Ser His Ala Val Ile Leu Gly Asp Thr Arg Tyr Gly
                725                 730                 735

Ser Glu Glu Lys Gly Thr Tyr His Leu Ala Leu Phe Gly Asp Arg Ala
            740                 745                 750

Gln Glu Ile Ala Gly Ser Ala Thr Val Lys Ile Gly Glu Lys Val His
        755                 760                 765

Glu Ile Gly Ile Ala Gly Lys Gln
    770                 775


<210> SEQ ID NO 38
<211> LENGTH: 772
<212> TYPE: PRT
<213> ORGANISM: Neisseria meningitidis

<400> SEQUENCE: 38

Met Val Ala Ala Asp Ile Gly Ala Gly Leu Ala Asp Ala Leu Thr Ala
1               5                   10                  15

Pro Leu Asp His Lys Asp Lys Gly Leu Gln Ser Leu Thr Leu Asp Gln
            20                  25                  30

Ser Val Arg Lys Asn Glu Lys Leu Lys Leu Ala Ala Gln Gly Ala Glu
        35                  40                  45

Lys Thr Tyr Gly Asn Gly Asp Ser Leu Asn Thr Gly Lys Leu Lys Asn
    50                  55                  60

Asp Lys Val Ser Arg Phe Asp Phe Ile Arg Gln Ile Glu Val Asp Gly
65                  70                  75                  80

Gln Leu Ile Thr Leu Glu Ser Gly Glu Phe Gln Val Tyr Lys Gln Ser
                85                  90                  95
```

```
His Ser Ala Leu Thr Ala Phe Gln Thr Glu Gln Ile Gln Asp Ser Glu
            100                 105                 110

His Ser Gly Lys Met Val Ala Lys Arg Gln Phe Arg Ile Gly Asp Ile
        115                 120                 125

Ala Gly Glu His Thr Ser Phe Asp Lys Leu Pro Glu Gly Gly Arg Ala
    130                 135                 140

Thr Tyr Arg Gly Thr Ala Phe Gly Ser Asp Asp Ala Gly Gly Lys Leu
145                 150                 155                 160

Thr Tyr Thr Ile Asp Phe Ala Ala Lys Gln Gly Asn Gly Lys Ile Glu
                165                 170                 175

His Leu Lys Ser Pro Glu Leu Asn Val Asp Leu Ala Ala Ala Asp Ile
            180                 185                 190

Lys Pro Asp Gly Lys Arg His Ala Val Ile Ser Gly Ser Val Leu Tyr
        195                 200                 205

Asn Gln Ala Glu Lys Gly Ser Tyr Ser Leu Gly Ile Phe Gly Gly Lys
    210                 215                 220

Ala Gln Glu Val Ala Gly Ser Ala Glu Val Lys Thr Val Asn Gly Ile
225                 230                 235                 240

Arg His Ile Gly Leu Ala Ala Lys Gln Gly Ser Gly Pro Asp Ser Asp
                245                 250                 255

Arg Leu Gln Gln Arg Arg Val Ala Ala Asp Ile Gly Ala Gly Leu Ala
            260                 265                 270

Asp Ala Leu Thr Ala Pro Leu Asp His Lys Asp Lys Ser Leu Gln Ser
        275                 280                 285

Leu Thr Leu Asp Gln Ser Val Arg Lys Asn Glu Lys Leu Lys Leu Ala
    290                 295                 300

Ala Gln Gly Ala Glu Lys Thr Tyr Gly Asn Gly Asp Ser Leu Asn Thr
305                 310                 315                 320

Gly Lys Leu Lys Asn Asp Lys Val Ser Arg Phe Asp Phe Ile Arg Gln
                325                 330                 335

Ile Glu Val Asp Gly Gln Leu Ile Thr Leu Glu Ser Gly Glu Phe Gln
            340                 345                 350

Ile Tyr Lys Gln Asp His Ser Ala Val Val Ala Leu Gln Ile Glu Lys
        355                 360                 365

Ile Asn Asn Pro Asp Lys Ile Asp Ser Leu Ile Asn Gln Arg Ser Phe
    370                 375                 380

Leu Val Ser Gly Leu Gly Gly Glu His Thr Ala Phe Asn Gln Leu Pro
385                 390                 395                 400

Asp Gly Lys Ala Glu Tyr His Gly Lys Ala Phe Ser Ser Asp Asp Ala
                405                 410                 415

Gly Gly Lys Leu Thr Tyr Thr Ile Asp Phe Ala Ala Lys Gln Gly His
            420                 425                 430

Gly Lys Ile Glu His Leu Lys Thr Pro Glu Gln Asn Val Glu Leu Ala
        435                 440                 445

Ala Ala Glu Leu Lys Ala Asp Glu Lys Ser His Ala Val Ile Leu Gly
    450                 455                 460

Asp Thr Arg Tyr Gly Ser Glu Glu Lys Gly Thr Tyr His Leu Ala Leu
465                 470                 475                 480

Phe Gly Asp Arg Ala Gln Glu Ile Ala Gly Ser Ala Thr Val Lys Ile
                485                 490                 495

Gly Glu Lys Val His Glu Ile Gly Ile Ala Gly Lys Gln Gly Ser Gly
            500                 505                 510

Pro Asp Ser Asp Arg Leu Gln Gln Arg Arg Val Ala Ala Asp Ile Gly
```

-continued

```
        515                 520                 525

Thr Gly Leu Ala Asp Ala Leu Thr Ala Pro Leu Asp His Lys Asp Lys
    530                 535                 540

Gly Leu Lys Ser Leu Thr Leu Glu Asp Ser Ile Pro Gln Asn Gly Thr
545                 550                 555                 560

Leu Thr Leu Ser Ala Gln Gly Ala Glu Lys Thr Phe Lys Ala Gly Asp
                565                 570                 575

Lys Asp Asn Ser Leu Asn Thr Gly Lys Leu Lys Asn Asp Lys Ile Ser
            580                 585                 590

Arg Phe Asp Phe Val Gln Lys Ile Glu Val Asp Gly Gln Thr Ile Thr
        595                 600                 605

Leu Ala Ser Gly Glu Phe Gln Ile Tyr Lys Gln Asn His Ser Ala Val
    610                 615                 620

Val Ala Leu Gln Ile Glu Lys Ile Asn Asn Pro Asp Lys Thr Asp Ser
625                 630                 635                 640

Leu Ile Asn Gln Arg Ser Phe Leu Val Ser Gly Leu Gly Gly Glu His
                645                 650                 655

Thr Ala Phe Asn Gln Leu Pro Gly Gly Lys Ala Glu Tyr His Gly Lys
            660                 665                 670

Ala Phe Ser Ser Asp Asp Pro Asn Gly Arg Leu His Tyr Ser Ile Asp
        675                 680                 685

Phe Thr Lys Lys Gln Gly Tyr Gly Arg Ile Glu His Leu Lys Thr Leu
    690                 695                 700

Glu Gln Asn Val Glu Leu Ala Ala Ala Glu Leu Lys Ala Asp Glu Lys
705                 710                 715                 720

Ser His Ala Val Ile Leu Gly Asp Thr Arg Tyr Gly Ser Glu Glu Lys
                725                 730                 735

Gly Thr Tyr His Leu Ala Leu Phe Gly Asp Arg Ala Gln Glu Ile Ala
            740                 745                 750

Gly Ser Ala Thr Val Lys Ile Gly Glu Lys Val His Glu Ile Gly Ile
        755                 760                 765

Ala Gly Lys Gln
    770


<210> SEQ ID NO 39
<211> LENGTH: 765
<212> TYPE: PRT
<213> ORGANISM: Neisseria meningitidis

<400> SEQUENCE: 39

Met Val Ala Ala Asp Ile Gly Ala Gly Leu Ala Asp Ala Leu Thr Ala
1               5                   10                  15

Leu Asp His Lys Asp Lys Gly Leu Gln Ser Leu Thr Leu Asp Gln Ser
            20                  25                  30

Val Arg Lys Asn Glu Lys Leu Lys Leu Ala Ala Gln Gly Ala Glu Lys
        35                  40                  45

Thr Tyr Gly Asn Gly Asp Ser Leu Asn Thr Gly Lys Leu Lys Asn Asp
    50                  55                  60

Lys Val Ser Arg Phe Asp Phe Ile Arg Gln Ile Glu Val Asp Gly Gln
65                  70                  75                  80

Leu Ile Thr Leu Glu Ser Gly Glu Phe Gln Val Tyr Lys Gln Ser His
                85                  90                  95

Ser Ala Leu Thr Ala Phe Gln Thr Glu Gln Ile Gln Asp Ser Glu His
            100                 105                 110

Ser Gly Lys Met Val Ala Lys Arg Gln Phe Arg Ile Gly Asp Ile Ala
```

-continued

```
        115                 120                 125

Gly Glu His Thr Ser Phe Asp Lys Leu Glu Gly Gly Arg Ala Thr Tyr
    130                 135                 140

Arg Gly Thr Ala Phe Gly Ser Asp Asp Ala Gly Gly Lys Leu Thr Tyr
145                 150                 155                 160

Thr Ile Asp Phe Ala Ala Lys Gln Gly Asn Gly Lys Ile Glu His Leu
                165                 170                 175

Lys Ser Glu Leu Asn Val Asp Leu Ala Ala Ala Asp Ile Lys Asp Gly
            180                 185                 190

Lys Arg His Ala Val Ile Ser Gly Ser Val Leu Tyr Asn Gln Ala Glu
        195                 200                 205

Lys Gly Ser Tyr Ser Leu Gly Ile Phe Gly Gly Lys Ala Gln Glu Val
    210                 215                 220

Ala Gly Ser Ala Glu Val Lys Thr Val Asn Gly Ile Arg His Ile Gly
225                 230                 235                 240

Leu Ala Ala Lys Gln Gly Ser Gly Asp Ser Asp Arg Leu Gln Gln Arg
                245                 250                 255

Arg Val Ala Ala Asp Ile Gly Thr Gly Leu Ala Asp Ala Leu Thr Ala
            260                 265                 270

Leu Asp His Lys Asp Lys Gly Leu Lys Ser Leu Thr Leu Glu Asp Ser
        275                 280                 285

Ile Gln Asn Gly Thr Leu Thr Leu Ser Ala Gln Gly Ala Glu Lys Thr
    290                 295                 300

Phe Lys Ala Gly Asp Lys Asp Asn Ser Leu Asn Thr Gly Lys Leu Lys
305                 310                 315                 320

Asn Asp Lys Ile Ser Arg Phe Asp Phe Val Gln Lys Ile Glu Val Asp
                325                 330                 335

Gly Gln Thr Ile Thr Leu Ala Ser Gly Glu Phe Gln Ile Tyr Lys Gln
            340                 345                 350

Asn His Ser Ala Val Val Ala Leu Gln Ile Glu Lys Ile Asn Asn Asp
        355                 360                 365

Lys Thr Asp Ser Leu Ile Asn Gln Arg Ser Phe Leu Val Ser Gly Leu
    370                 375                 380

Gly Gly Glu His Thr Ala Phe Asn Gln Leu Gly Gly Lys Ala Glu Tyr
385                 390                 395                 400

His Gly Lys Ala Phe Ser Ser Asp Asp Asn Gly Arg Leu His Tyr Ser
                405                 410                 415

Ile Asp Phe Thr Lys Lys Gln Gly Tyr Gly Arg Ile Glu His Leu Lys
            420                 425                 430

Thr Leu Glu Gln Asn Val Glu Leu Ala Ala Ala Glu Leu Lys Ala Asp
        435                 440                 445

Glu Lys Ser His Ala Val Ile Leu Gly Asp Thr Arg Tyr Gly Ser Glu
    450                 455                 460

Glu Lys Gly Thr Tyr His Leu Ala Leu Phe Gly Asp Arg Ala Gln Glu
465                 470                 475                 480

Ile Ala Gly Ser Ala Thr Val Lys Ile Gly Glu Lys Val His Glu Ile
                485                 490                 495

Gly Ile Ala Gly Lys Gln Gly Lys Gly Asp Ser Asp Arg Leu Gln Gln
            500                 505                 510

Arg Arg Val Ala Ala Asp Ile Gly Ala Gly Leu Ala Asp Ala Leu Thr
        515                 520                 525

Ala Leu Asp His Lys Asp Lys Ser Leu Gln Ser Leu Thr Leu Asp Gln
    530                 535                 540
```

Ser Val Arg Lys Asn Glu Lys Leu Lys Leu Ala Ala Gln Gly Ala Glu
545 550 555 560

Lys Thr Tyr Gly Asn Gly Asp Ser Leu Asn Thr Gly Lys Leu Lys Asn
565 570 575

Asp Lys Val Ser Arg Phe Asp Phe Ile Arg Gln Ile Glu Val Asp Gly
580 585 590

Gln Leu Ile Thr Leu Glu Ser Gly Glu Phe Gln Ile Tyr Lys Gln Asp
595 600 605

His Ser Ala Val Val Ala Leu Gln Ile Glu Lys Ile Asn Asn Asp Lys
610 615 620

Ile Asp Ser Leu Ile Asn Gln Arg Ser Phe Leu Val Ser Gly Leu Gly
625 630 635 640

Gly Glu His Thr Ala Phe Asn Gln Leu Asp Gly Lys Ala Glu Tyr His
645 650 655

Gly Lys Ala Phe Ser Ser Asp Asp Ala Gly Gly Lys Leu Thr Tyr Thr
660 665 670

Ile Asp Phe Ala Ala Lys Gln Gly His Gly Lys Ile Glu His Leu Lys
675 680 685

Thr Glu Gln Asn Val Glu Leu Ala Ala Ala Glu Leu Lys Ala Asp Glu
690 695 700

Lys Ser His Ala Val Ile Leu Gly Asp Thr Arg Tyr Gly Ser Glu Glu
705 710 715 720

Lys Gly Thr Tyr His Leu Ala Leu Phe Gly Asp Arg Ala Gln Glu Ile
725 730 735

Ala Gly Ser Ala Thr Val Lys Ile Gly Glu Lys Val His Glu Ile Gly
740 745 750

Ile Ala Gly Lys Gln Leu Glu His His His His His His
755 760 765

<210> SEQ ID NO 40
<211> LENGTH: 772
<212> TYPE: PRT
<213> ORGANISM: Neisseria meningitidis

<400> SEQUENCE: 40

Met Val Ala Ala Asp Ile Gly Ala Gly Leu Ala Asp Ala Leu Thr Ala
1 5 10 15

Pro Leu Asp His Lys Asp Lys Gly Leu Gln Ser Leu Thr Leu Asp Gln
20 25 30

Ser Val Arg Lys Asn Glu Lys Leu Lys Leu Ala Ala Gln Gly Ala Glu
35 40 45

Lys Thr Tyr Gly Asn Gly Asp Ser Leu Asn Thr Gly Lys Leu Lys Asn
50 55 60

Asp Lys Val Ser Arg Phe Asp Phe Ile Arg Gln Ile Glu Val Asp Gly
65 70 75 80

Gln Leu Ile Thr Leu Glu Ser Gly Glu Phe Gln Val Tyr Lys Gln Ser
85 90 95

His Ser Ala Leu Thr Ala Phe Gln Thr Glu Gln Ile Gln Asp Ser Glu
100 105 110

His Ser Gly Lys Met Val Ala Lys Arg Gln Phe Arg Ile Gly Asp Ile
115 120 125

Ala Gly Glu His Thr Ser Phe Asp Lys Leu Pro Glu Gly Gly Arg Ala
130 135 140

Thr Tyr Arg Gly Thr Ala Phe Gly Ser Asp Asp Ala Gly Gly Lys Leu
145 150 155 160

-continued

```
Thr Tyr Thr Ile Asp Phe Ala Ala Lys Gln Gly Asn Gly Lys Ile Glu
                165                 170                 175

His Leu Lys Ser Pro Glu Leu Asn Val Asp Leu Ala Ala Ala Asp Ile
            180                 185                 190

Lys Pro Asp Gly Lys Arg His Ala Val Ile Ser Gly Ser Val Leu Tyr
        195                 200                 205

Asn Gln Ala Glu Lys Gly Ser Tyr Ser Leu Gly Ile Phe Gly Gly Lys
    210                 215                 220

Ala Gln Glu Val Ala Gly Ser Ala Glu Val Lys Thr Val Asn Gly Ile
225                 230                 235                 240

Arg His Ile Gly Leu Ala Ala Lys Gln Gly Ser Gly Pro Asp Ser Asp
                245                 250                 255

Arg Leu Gln Gln Arg Arg Val Ala Ala Asp Ile Gly Thr Gly Leu Ala
            260                 265                 270

Asp Ala Leu Thr Ala Pro Leu Asp His Lys Asp Lys Gly Leu Lys Ser
        275                 280                 285

Leu Thr Leu Glu Asp Ser Ile Pro Gln Asn Gly Thr Leu Thr Leu Ser
    290                 295                 300

Ala Gln Gly Ala Glu Lys Thr Phe Lys Ala Gly Asp Lys Asp Asn Ser
305                 310                 315                 320

Leu Asn Thr Gly Lys Leu Lys Asn Asp Lys Ile Ser Arg Phe Asp Phe
                325                 330                 335

Val Gln Lys Ile Glu Val Asp Gly Gln Thr Ile Thr Leu Ala Ser Gly
            340                 345                 350

Glu Phe Gln Ile Tyr Lys Gln Asn His Ser Ala Val Val Ala Leu Gln
        355                 360                 365

Ile Glu Lys Ile Asn Asn Pro Asp Lys Thr Asp Ser Leu Ile Asn Gln
    370                 375                 380

Arg Ser Phe Leu Val Ser Gly Leu Gly Gly Glu His Thr Ala Phe Asn
385                 390                 395                 400

Gln Leu Pro Gly Gly Lys Ala Glu Tyr His Gly Lys Ala Phe Ser Ser
                405                 410                 415

Asp Asp Pro Asn Gly Arg Leu His Tyr Ser Ile Asp Phe Thr Lys Lys
            420                 425                 430

Gln Gly Tyr Gly Arg Ile Glu His Leu Lys Thr Leu Glu Gln Asn Val
        435                 440                 445

Glu Leu Ala Ala Ala Glu Leu Lys Ala Asp Glu Lys Ser His Ala Val
    450                 455                 460

Ile Leu Gly Asp Thr Arg Tyr Gly Ser Glu Glu Lys Gly Thr Tyr His
465                 470                 475                 480

Leu Ala Leu Phe Gly Asp Arg Ala Gln Glu Ile Ala Gly Ser Ala Thr
                485                 490                 495

Val Lys Ile Gly Glu Lys Val His Glu Ile Gly Ile Ala Gly Lys Gln
            500                 505                 510

Gly Lys Gly Pro Asp Ser Asp Arg Leu Gln Gln Arg Arg Val Ala Ala
        515                 520                 525

Asp Ile Gly Ala Gly Leu Ala Asp Ala Leu Thr Ala Pro Leu Asp His
    530                 535                 540

Lys Asp Lys Ser Leu Gln Ser Leu Thr Leu Asp Gln Ser Val Arg Lys
545                 550                 555                 560

Asn Glu Lys Leu Lys Leu Ala Ala Gln Gly Ala Glu Lys Thr Tyr Gly
                565                 570                 575

Asn Gly Asp Ser Leu Asn Thr Gly Lys Leu Lys Asn Asp Lys Val Ser
            580                 585                 590
```

Arg Phe Asp Phe Ile Arg Gln Ile Glu Val Asp Gly Gln Leu Ile Thr
595 600 605

Leu Glu Ser Gly Glu Phe Gln Ile Tyr Lys Gln Asp His Ser Ala Val
610 615 620

Val Ala Leu Gln Ile Glu Lys Ile Asn Asn Pro Asp Lys Ile Asp Ser
625 630 635 640

Leu Ile Asn Gln Arg Ser Phe Leu Val Ser Gly Leu Gly Gly Glu His
645 650 655

Thr Ala Phe Asn Gln Leu Pro Asp Gly Lys Ala Glu Tyr His Gly Lys
660 665 670

Ala Phe Ser Ser Asp Asp Ala Gly Gly Lys Leu Thr Tyr Thr Ile Asp
675 680 685

Phe Ala Ala Lys Gln Gly His Gly Lys Ile Glu His Leu Lys Thr Pro
690 695 700

Glu Gln Asn Val Glu Leu Ala Ala Ala Glu Leu Lys Ala Asp Glu Lys
705 710 715 720

Ser His Ala Val Ile Leu Gly Asp Thr Arg Tyr Gly Ser Glu Glu Lys
725 730 735

Gly Thr Tyr His Leu Ala Leu Phe Gly Asp Arg Ala Gln Glu Ile Ala
740 745 750

Gly Ser Ala Thr Val Lys Ile Gly Glu Lys Val His Glu Ile Gly Ile
755 760 765

Ala Gly Lys Gln
770

<210> SEQ ID NO 41
<211> LENGTH: 8
<212> TYPE: PRT
<213> ORGANISM: Neisseria meningitidis

<400> SEQUENCE: 41

Leu Glu His His His His His His
1 5

<210> SEQ ID NO 42
<211> LENGTH: 2
<212> TYPE: PRT
<213> ORGANISM: Neisseria meningitidis

<400> SEQUENCE: 42

Lys Leu
1

<210> SEQ ID NO 43
<211> LENGTH: 1
<212> TYPE: PRT
<213> ORGANISM: Neisseria meningitidis

<400> SEQUENCE: 43

Met
1

<210> SEQ ID NO 44
<211> LENGTH: 2
<212> TYPE: PRT
<213> ORGANISM: Neisseria meningitidis

<400> SEQUENCE: 44

Leu Glu
1

<210> SEQ ID NO 45
<211> LENGTH: 6
<212> TYPE: PRT
<213> ORGANISM: Neisseria meningitidis

<400> SEQUENCE: 45

```
Leu Glu Gly Gly Gly Gly
1               5
```

<210> SEQ ID NO 46
<211> LENGTH: 274
<212> TYPE: PRT
<213> ORGANISM: Neisseria meningitidis

<400> SEQUENCE: 46

```
Met Asn Arg Thr Ala Phe Cys Cys Leu Ser Leu Thr Thr Ala Leu Ile
1               5                   10                  15

Leu Thr Ser Cys Ser Ser Gly Gly Gly Gly Val Ala Ala Asp Ile Gly
            20                  25                  30

Ala Gly Leu Ala Asp Ala Leu Thr Ala Pro Leu Asp His Lys Asp Lys
        35                  40                  45

Gly Leu Gln Ser Leu Met Leu Asp Gln Ser Val Arg Lys Asn Glu Lys
    50                  55                  60

Leu Lys Leu Ala Ala Gln Gly Ala Glu Lys Thr Tyr Gly Asn Gly Asp
65                  70                  75                  80

Ser Leu Asn Thr Gly Lys Leu Lys Asn Asp Lys Val Ser Arg Phe Asp
                85                  90                  95

Phe Ile Arg Gln Ile Glu Val Asp Gly Gln Leu Ile Thr Leu Glu Ser
            100                 105                 110

Gly Glu Phe Gln Val Tyr Lys Gln Ser His Ser Ala Leu Thr Ala Leu
        115                 120                 125

Gln Thr Glu Gln Val Gln Asp Ser Glu His Ser Gly Arg Met Val Ala
    130                 135                 140

Lys Arg Gln Phe Arg Ile Gly Asp Ile Ala Gly Glu His Thr Ser Phe
145                 150                 155                 160

Asp Lys Leu Pro Glu Gly Gly Arg Ala Thr Tyr Arg Gly Thr Ala Phe
                165                 170                 175

Gly Ser Asp Asp Ala Gly Gly Lys Leu Ile Tyr Thr Ile Asp Phe Ala
            180                 185                 190

Ala Lys Gln Gly His Gly Lys Ile Glu His Leu Lys Ser Pro Glu Leu
        195                 200                 205

Asn Val Asp Leu Ala Ala Ala Tyr Ile Lys Pro Asp Glu Lys His His
    210                 215                 220

Ala Val Ile Ser Gly Ser Val Leu Tyr Asn Gln Ala Glu Lys Gly Ser
225                 230                 235                 240

Tyr Ser Leu Gly Ile Phe Gly Gly Lys Ala Gln Glu Val Ala Gly Ser
                245                 250                 255

Ala Glu Val Lys Thr Val Asn Gly Ile Arg His Ile Gly Leu Ala Ala
            260                 265                 270

Lys Gln
```

<210> SEQ ID NO 47
<211> LENGTH: 281
<212> TYPE: PRT
<213> ORGANISM: Neisseria meningitidis

<400> SEQUENCE: 47

```
Met Asn Arg Thr Thr Phe Cys Cys Leu Ser Leu Thr Thr Ala Leu Ile
1               5                   10                  15

Leu Thr Ala Cys Ser Ser Gly Gly Gly Gly Ser Gly Gly Gly Gly Val
            20                  25                  30

Ala Ala Asp Ile Gly Ala Gly Leu Ala Asp Ala Leu Thr Ala Pro Leu
        35                  40                  45

Asp His Lys Asp Lys Gly Leu Lys Ser Leu Thr Leu Glu Asp Ser Ile
    50                  55                  60

Pro Gln Asn Gly Thr Leu Thr Leu Ser Ala Gln Gly Ala Glu Lys Thr
65                  70                  75                  80

Phe Lys Ala Gly Gly Lys Asp Asn Ser Leu Asn Thr Gly Lys Leu Lys
                85                  90                  95

Asn Asp Lys Ile Ser Arg Phe Asp Phe Val Gln Lys Ile Glu Val Asp
            100                 105                 110

Gly Gln Thr Ile Thr Leu Ala Ser Gly Glu Phe Gln Ile Tyr Lys Gln
        115                 120                 125

Asn His Ser Ala Val Val Ala Leu Gln Ile Glu Lys Ile Asn Asn Pro
    130                 135                 140

Asp Lys Thr Asp Ser Leu Ile Asn Gln Arg Ser Phe Leu Val Ser Gly
145                 150                 155                 160

Leu Gly Gly Glu His Thr Ala Phe Asn Gln Leu Pro Gly Gly Lys Ala
                165                 170                 175

Glu Tyr His Gly Lys Ala Phe Ser Ser Asp Asp Pro Asn Gly Arg Leu
            180                 185                 190

His Tyr Thr Ile Asp Phe Thr Asn Lys Gln Gly Tyr Gly Arg Ile Glu
        195                 200                 205

His Leu Lys Thr Pro Glu Gln Asn Val Glu Leu Ala Ser Ala Glu Leu
    210                 215                 220

Lys Ala Asp Glu Lys Ser His Ala Val Ile Leu Gly Asp Thr Arg Tyr
225                 230                 235                 240

Gly Ser Glu Glu Lys Gly Thr Tyr His Leu Ala Leu Phe Gly Asp Arg
                245                 250                 255

Ala Gln Glu Ile Ala Gly Ser Ala Thr Val Lys Ile Gly Glu Lys Val
            260                 265                 270

His Glu Ile Gly Ile Ala Gly Lys Gln
        275                 280
```

<210> SEQ ID NO 48
<211> LENGTH: 279
<212> TYPE: PRT
<213> ORGANISM: Neisseria meningitidis

<400> SEQUENCE: 48

```
Met Asn Arg Thr Ala Phe Cys Cys Leu Ser Leu Thr Ala Ala Leu Ile
1               5                   10                  15

Leu Thr Ala Cys Ser Ser Gly Gly Gly Gly Ser Gly Gly Gly Gly Val
            20                  25                  30

Ala Ala Asp Ile Gly Ala Gly Leu Ala Asp Ala Leu Thr Ala Pro Leu
        35                  40                  45

Asp His Lys Asp Lys Gly Leu Gln Ser Leu Met Leu Asp Gln Ser Val
    50                  55                  60

Arg Lys Asn Glu Lys Leu Lys Leu Ala Ala Gln Gly Ala Glu Lys Thr
65                  70                  75                  80

Tyr Gly Asn Gly Asp Ser Leu Asn Thr Gly Lys Leu Lys Asn Asp Lys
                85                  90                  95
```

```
Val Ser Arg Phe Asp Phe Ile Arg Gln Ile Glu Val Asp Gly Arg Leu
            100                 105                 110

Ile Thr Leu Glu Ser Gly Glu Phe Gln Val Tyr Lys Gln Ser Tyr Ser
        115                 120                 125

Ala Leu Thr Ala Leu Gln Thr Glu Gln Val Gln Asp Ser Glu Asp Ser
    130                 135                 140

Arg Lys Met Val Ala Lys Arg Gln Phe Arg Ile Gly Asp Ile Ala Gly
145                 150                 155                 160

Glu His Thr Ser Phe Asp Lys Leu Pro Glu Ser Asp Arg Ala Thr Tyr
                165                 170                 175

Arg Gly Thr Ala Phe Ser Ser Asp Asp Ala Gly Gly Lys Leu Thr Tyr
            180                 185                 190

Thr Ile Asp Phe Ala Val Lys Gln Gly His Gly Lys Ile Glu His Leu
        195                 200                 205

Lys Ser Pro Glu Leu Asn Val Glu Leu Ala Thr Ala Tyr Ile Lys Pro
    210                 215                 220

Asp Glu Lys His His Ala Val Ile Ser Gly Ser Val Leu Tyr Asn Gln
225                 230                 235                 240

Asp Glu Lys Gly Ser Tyr Ser Leu Gly Ile Phe Gly Gly Gln Ala Gln
                245                 250                 255

Glu Val Ala Gly Ser Ala Glu Val Glu Thr Ala Asn Gly Ile His His
            260                 265                 270

Ile Gly Leu Ala Ala Lys Gln
        275


<210> SEQ ID NO 49
<211> LENGTH: 273
<212> TYPE: PRT
<213> ORGANISM: Neisseria meningitidis

<400> SEQUENCE: 49

Met Asn Arg Thr Ala Phe Cys Cys Phe Ser Leu Thr Ala Ala Leu Ile
1               5                   10                  15

Leu Thr Ala Cys Ser Ser Gly Gly Gly Gly Val Ala Ala Asp Ile Gly
            20                  25                  30

Ala Gly Leu Ala Asp Ala Leu Thr Ala Pro Leu Asp His Lys Asp Lys
        35                  40                  45

Ser Leu Gln Ser Leu Thr Leu Asp Gln Ser Val Arg Lys Asn Glu Lys
    50                  55                  60

Leu Lys Leu Ala Ala Gln Gly Ala Glu Lys Thr Tyr Gly Asn Gly Asp
65                  70                  75                  80

Ser Leu Asn Thr Gly Lys Leu Lys Asn Asp Lys Val Ser Arg Phe Asp
                85                  90                  95

Phe Ile Arg Gln Ile Glu Val Asp Gly Gln Thr Ile Thr Leu Ala Ser
            100                 105                 110

Gly Glu Phe Gln Ile Tyr Lys Gln Asn His Ser Ala Val Val Ala Leu
        115                 120                 125

Gln Ile Glu Lys Ile Asn Asn Pro Asp Lys Ile Asp Ser Leu Ile Asn
    130                 135                 140

Gln Arg Ser Phe Leu Val Ser Gly Leu Gly Gly Glu His Thr Ala Phe
145                 150                 155                 160

Asn Gln Leu Pro Asp Gly Lys Ala Glu Tyr His Gly Lys Ala Phe Ser
                165                 170                 175

Ser Asp Asp Pro Asn Gly Arg Leu His Tyr Ser Ile Asp Phe Thr Lys
            180                 185                 190
```

```
Lys Gln Gly Tyr Gly Arg Ile Glu His Leu Lys Thr Pro Glu Gln Asn
        195                 200                 205

Val Glu Leu Ala Ser Ala Glu Leu Lys Ala Asp Glu Lys Ser His Ala
    210                 215                 220

Val Ile Leu Gly Asp Thr Arg Tyr Gly Gly Glu Glu Lys Gly Thr Tyr
225                 230                 235                 240

His Leu Ala Leu Phe Gly Asp Arg Ala Gln Glu Ile Ala Gly Ser Ala
                245                 250                 255

Thr Val Lys Ile Arg Glu Lys Val His Glu Ile Gly Ile Ala Gly Lys
            260                 265                 270

Gln


<210> SEQ ID NO 50
<211> LENGTH: 273
<212> TYPE: PRT
<213> ORGANISM: Neisseria meningitidis

<400> SEQUENCE: 50

Met Asn Arg Thr Ala Phe Cys Cys Leu Ser Leu Thr Ala Ala Leu Ile
1               5                   10                  15

Leu Thr Ala Cys Ser Ser Gly Gly Gly Gly Val Ala Ala Asp Ile Gly
            20                  25                  30

Ala Gly Leu Ala Asp Ala Leu Thr Thr Pro Leu Asp His Lys Asp Lys
        35                  40                  45

Ser Leu Gln Ser Leu Thr Leu Asp Gln Ser Val Arg Lys Asn Glu Lys
    50                  55                  60

Leu Lys Leu Ala Ala Gln Gly Ala Glu Lys Thr Tyr Gly Asn Gly Asp
65                  70                  75                  80

Ser Leu Asn Thr Gly Lys Leu Lys Asn Asp Lys Val Ser Arg Phe Asp
                85                  90                  95

Phe Ile Arg Gln Ile Glu Val Asp Gly Gln Leu Ile Thr Leu Glu Ser
            100                 105                 110

Gly Glu Phe Gln Ile Tyr Lys Gln Asn His Ser Ala Val Val Ala Leu
        115                 120                 125

Gln Ile Glu Lys Ile Asn Asn Pro Asp Lys Ile Asp Ser Leu Ile Asn
    130                 135                 140

Gln Arg Ser Phe Leu Val Ser Gly Leu Gly Gly Glu His Thr Ala Phe
145                 150                 155                 160

Asn Gln Leu Pro Ser Gly Lys Ala Glu Tyr His Gly Lys Ala Phe Ser
                165                 170                 175

Ser Asp Asp Pro Asn Gly Arg Leu His Tyr Ser Ile Asp Phe Thr Lys
            180                 185                 190

Lys Gln Gly Tyr Gly Arg Ile Glu His Leu Lys Thr Pro Glu Gln Asn
        195                 200                 205

Val Glu Leu Ala Ser Ala Glu Leu Lys Ala Asp Glu Lys Ser His Ala
    210                 215                 220

Val Ile Leu Gly Asp Thr Arg Tyr Gly Gly Glu Glu Lys Gly Thr Tyr
225                 230                 235                 240

His Leu Ala Leu Phe Gly Asp Arg Ala Gln Glu Ile Ala Gly Ser Ala
                245                 250                 255

Thr Val Lys Ile Arg Glu Lys Val His Glu Ile Gly Ile Ala Gly Lys
            260                 265                 270

Gln
```

<210> SEQ ID NO 51
<211> LENGTH: 273
<212> TYPE: PRT
<213> ORGANISM: Neisseria meningitidis

<400> SEQUENCE: 51

```
Met Asn Arg Thr Ala Phe Cys Cys Leu Ser Leu Thr Thr Ala Leu Ile
1               5                   10                  15

Leu Thr Ala Cys Ser Ser Gly Gly Gly Gly Val Ala Ala Asp Ile Gly
            20                  25                  30

Ala Gly Leu Ala Asp Ala Leu Thr Ala Pro Leu Asp His Lys Asp Lys
        35                  40                  45

Gly Leu Gln Ser Leu Thr Leu Asp Gln Ser Val Arg Lys Asn Glu Lys
    50                  55                  60

Leu Lys Leu Ala Ala Gln Gly Ala Glu Lys Thr Tyr Gly Asn Gly Asp
65                  70                  75                  80

Ser Leu Asn Thr Gly Lys Leu Lys Asn Asp Lys Val Ser Arg Phe Asp
                85                  90                  95

Phe Ile Arg Gln Ile Glu Val Asp Gly Gln Thr Ile Thr Leu Ala Ser
            100                 105                 110

Gly Glu Phe Gln Ile Tyr Lys Gln Asn His Ser Ala Val Val Ala Leu
        115                 120                 125

Gln Ile Glu Lys Ile Asn Asn Pro Asp Lys Ile Asp Ser Leu Ile Asn
    130                 135                 140

Gln Arg Ser Phe Leu Val Ser Gly Leu Gly Gly Glu His Thr Ala Phe
145                 150                 155                 160

Asn Gln Leu Pro Asp Gly Lys Ala Glu Tyr His Gly Lys Ala Phe Ser
                165                 170                 175

Ser Asp Asp Pro Asn Gly Arg Leu His Tyr Ser Ile Asp Phe Thr Lys
            180                 185                 190

Lys Gln Gly Tyr Gly Arg Ile Glu His Leu Lys Thr Pro Glu Gln Asn
        195                 200                 205

Val Glu Leu Ala Ser Ala Glu Leu Lys Ala Asp Glu Lys Ser His Ala
    210                 215                 220

Val Ile Leu Gly Asp Thr Arg Tyr Gly Gly Glu Glu Lys Gly Thr Tyr
225                 230                 235                 240

His Leu Ala Leu Phe Gly Asp Arg Ala Gln Glu Ile Ala Gly Ser Ala
                245                 250                 255

Thr Val Lys Ile Gly Glu Lys Val His Glu Ile Gly Ile Ala Gly Lys
            260                 265                 270

Gln
```

<210> SEQ ID NO 52
<211> LENGTH: 273
<212> TYPE: PRT
<213> ORGANISM: Neisseria meningitidis

<400> SEQUENCE: 52

```
Met Asn Arg Thr Ala Phe Cys Cys Leu Ser Leu Thr Ala Ala Leu Ile
1               5                   10                  15

Leu Thr Ala Cys Ser Ser Gly Gly Gly Gly Val Ala Ala Asp Ile Gly
            20                  25                  30

Ala Gly Leu Ala Asp Ala Leu Thr Thr Pro Leu Asp His Lys Asp Lys
        35                  40                  45

Ser Leu Gln Ser Leu Thr Leu Asp Gln Ser Val Arg Lys Asn Glu Lys
    50                  55                  60
```

-continued

Leu Lys Leu Ala Ala Gln Gly Ala Glu Lys Thr Tyr Gly Asn Gly Asp
65 70 75 80

Ser Leu Asn Thr Gly Lys Leu Lys Asn Asp Lys Val Ser Arg Phe Asp
85 90 95

Phe Ile Arg Gln Ile Glu Val Asp Gly Gln Thr Ile Thr Leu Ala Ser
100 105 110

Gly Glu Phe Gln Ile Tyr Lys Gln Asn His Ser Ala Val Val Ala Leu
115 120 125

Gln Ile Glu Lys Ile Asn Asn Pro Asp Lys Ile Asp Ser Leu Ile Asn
130 135 140

Gln Arg Ser Phe Leu Val Ser Gly Leu Gly Gly Glu His Thr Ala Phe
145 150 155 160

Asn Gln Leu Pro Ser Gly Lys Ala Glu Tyr His Gly Lys Ala Phe Ser
165 170 175

Ser Asp Asp Pro Asn Gly Arg Leu His Tyr Ser Ile Asp Phe Thr Lys
180 185 190

Lys Gln Gly Tyr Gly Arg Ile Glu His Leu Lys Thr Pro Glu Gln Asn
195 200 205

Val Glu Leu Ala Ser Ala Glu Leu Lys Ala Asp Glu Lys Ser His Ala
210 215 220

Val Ile Leu Gly Asp Thr Arg Tyr Gly Gly Glu Glu Lys Gly Thr Tyr
225 230 235 240

His Leu Ala Leu Phe Gly Asp Arg Ala Gln Glu Ile Ala Gly Ser Ala
245 250 255

Thr Val Lys Ile Arg Glu Lys Val His Glu Ile Gly Ile Ala Gly Lys
260 265 270

Gln

<210> SEQ ID NO 53
<211> LENGTH: 274
<212> TYPE: PRT
<213> ORGANISM: Neisseria meningitidis

<400> SEQUENCE: 53

Met Asn Arg Thr Ala Phe Cys Cys Leu Ser Leu Thr Thr Ala Leu Ile
1 5 10 15

Leu Thr Ala Cys Ser Ser Gly Gly Gly Gly Val Ala Ala Asp Ile Gly
20 25 30

Ala Gly Leu Ala Asp Ala Leu Thr Ala Pro Leu Asp His Lys Asp Lys
35 40 45

Gly Leu Gln Ser Leu Thr Leu Asp Gln Ser Val Arg Lys Asn Glu Lys
50 55 60

Leu Lys Leu Ala Ala Gln Gly Ala Glu Lys Thr Tyr Gly Asn Gly Asp
65 70 75 80

Ser Leu Asn Thr Gly Lys Leu Lys Asn Asp Lys Ile Ser Arg Phe Asp
85 90 95

Phe Ile Arg Gln Ile Glu Val Asp Gly Gln Leu Ile Thr Leu Glu Ser
100 105 110

Gly Glu Phe Gln Val Tyr Lys Gln Ser His Ser Ala Leu Thr Ala Leu
115 120 125

Gln Thr Glu Gln Val Gln Asp Ser Glu Asp Ser Gly Lys Met Val Ala
130 135 140

Lys Arg Gln Phe Arg Ile Gly Asp Ile Ala Gly Glu His Thr Ser Phe
145 150 155 160

Asp Lys Leu Pro Lys Gly Gly Arg Ala Thr Tyr Arg Gly Thr Ala Phe

```
                165                 170                 175

Gly Ser Asp Asp Ala Gly Gly Lys Leu Thr Tyr Thr Ile Asp Phe Ala
            180                 185                 190

Ala Lys Gln Gly His Gly Lys Ile Glu His Leu Lys Ser Pro Glu Leu
        195                 200                 205

Asn Val Asp Leu Ala Ala Ala Tyr Ile Lys Pro Asp Glu Lys Arg His
    210                 215                 220

Ala Val Ile Ser Gly Ser Val Leu Tyr Asn Gln Asp Glu Lys Gly Ser
225                 230                 235                 240

Tyr Ser Leu Gly Ile Phe Gly Gly Gln Ala Gln Glu Val Ala Gly Ser
                245                 250                 255

Ala Glu Val Glu Thr Ala Asn Gly Ile Gln His Ile Gly Leu Ala Ala
            260                 265                 270

Lys Gln


<210> SEQ ID NO 54
<211> LENGTH: 274
<212> TYPE: PRT
<213> ORGANISM: Neisseria meningitidis

<400> SEQUENCE: 54

Met Asn Arg Thr Ala Phe Cys Cys Leu Phe Leu Thr Thr Thr Leu Ile
1               5                   10                  15

Leu Thr Ala Cys Ser Ser Gly Gly Gly Gly Val Ala Ala Asp Ile Gly
            20                  25                  30

Ala Gly Leu Ala Asp Ala Leu Thr Ala Pro Leu Asp His Lys Asp Lys
        35                  40                  45

Gly Leu Gln Ser Leu Met Leu Asp Gln Ser Val Arg Lys Asn Glu Lys
    50                  55                  60

Leu Lys Leu Ala Ala Gln Gly Ala Glu Lys Thr Tyr Gly Asn Gly Asp
65                  70                  75                  80

Ser Leu Asn Thr Gly Lys Leu Lys Asn Asp Lys Val Ser Arg Phe Asp
                85                  90                  95

Phe Ile Arg Gln Ile Glu Val Asp Gly Gln Leu Ile Thr Leu Glu Ser
            100                 105                 110

Gly Glu Phe Gln Val Tyr Lys Gln Ser His Ser Ala Leu Thr Ala Leu
        115                 120                 125

Gln Thr Glu Gln Glu Gln Asp Pro Glu His Ser Glu Lys Met Val Ala
    130                 135                 140

Lys Arg Arg Phe Lys Ile Gly Asp Ile Ala Gly Glu His Thr Ser Phe
145                 150                 155                 160

Asp Lys Leu Pro Lys Asp Val Met Ala Thr Tyr Arg Gly Thr Ala Phe
                165                 170                 175

Gly Ser Asp Asp Ala Gly Gly Lys Leu Thr Tyr Thr Ile Asp Phe Ala
            180                 185                 190

Ala Lys Gln Gly His Gly Lys Ile Glu His Leu Lys Ser Pro Glu Leu
        195                 200                 205

Asn Val Asp Leu Ala Val Ala Tyr Ile Lys Pro Asp Glu Lys His His
    210                 215                 220

Ala Val Ile Ser Gly Ser Val Leu Tyr Asn Gln Asp Glu Lys Gly Ser
225                 230                 235                 240

Tyr Ser Leu Gly Ile Phe Gly Glu Lys Ala Gln Glu Val Ala Gly Ser
                245                 250                 255

Ala Glu Val Lys Thr Ala Asn Gly Ile His His Ile Gly Leu Ala Ala
            260                 265                 270
```

Lys Gln

<210> SEQ ID NO 55
<211> LENGTH: 274
<212> TYPE: PRT
<213> ORGANISM: Neisseria meningitidis

<400> SEQUENCE: 55

Met Asn Arg Thr Ala Phe Cys Cys Leu Ser Leu Thr Ala Ala Leu Ile
1 5 10 15

Leu Thr Ala Cys Ser Ser Gly Gly Gly Gly Val Ala Ala Asp Ile Gly
20 25 30

Ala Gly Leu Ala Asp Ala Leu Thr Ala Pro Leu Asp His Lys Asp Lys
35 40 45

Gly Leu Gln Ser Leu Thr Leu Asp Gln Ser Val Arg Lys Asn Glu Lys
50 55 60

Leu Lys Leu Ala Ala Gln Gly Ala Glu Lys Thr Tyr Gly Asn Gly Asp
65 70 75 80

Ser Leu Asn Thr Gly Lys Leu Lys Asn Asp Lys Val Ser Arg Phe Asp
85 90 95

Phe Ile Arg Gln Ile Glu Val Asp Gly Gln Leu Ile Thr Leu Glu Ser
100 105 110

Gly Glu Phe Gln Val Tyr Lys Gln Ser His Ser Ala Leu Thr Ala Phe
115 120 125

Gln Thr Glu Gln Ile Gln Asp Ser Glu His Ser Gly Lys Met Val Ala
130 135 140

Lys Arg Arg Phe Arg Ile Gly Asp Ile Ala Gly Glu His Thr Ser Phe
145 150 155 160

Asp Lys Leu Pro Glu Gly Gly Arg Ala Thr Tyr Arg Gly Thr Ala Phe
165 170 175

Gly Ser Asp Asp Ala Gly Gly Lys Leu Thr Tyr Thr Ile Asp Phe Ala
180 185 190

Ala Lys Gln Gly His Gly Lys Ile Glu His Leu Lys Ser Pro Glu Leu
195 200 205

Asn Val Asp Leu Ala Ala Ala Asp Ile Lys Pro Asp Glu Lys His His
210 215 220

Ala Val Ile Ser Gly Ser Val Leu Tyr Asn Gln Asp Glu Lys Gly Ser
225 230 235 240

Tyr Ser Leu Gly Ile Phe Gly Gly Lys Ala Gln Glu Val Ala Gly Ser
245 250 255

Ala Glu Val Glu Thr Ala Asn Gly Ile His His Ile Gly Leu Ala Ala
260 265 270

Lys Gln

<210> SEQ ID NO 56
<211> LENGTH: 281
<212> TYPE: PRT
<213> ORGANISM: Neisseria meningitidis

<400> SEQUENCE: 56

Met Asn Arg Thr Ala Phe Cys Cys Leu Ser Leu Thr Thr Ala Leu Ile
1 5 10 15

Leu Thr Ala Cys Ser Ser Gly Gly Gly Gly Ser Gly Gly Gly Gly Val
20 25 30

Ala Ala Asp Ile Gly Thr Gly Leu Ala Asp Ala Leu Thr Ala Pro Leu
35 40 45

Asp His Lys Asp Lys Gly Leu Lys Ser Leu Thr Leu Glu Ala Ser Ile
50 55 60

Pro Gln Asn Gly Thr Leu Thr Leu Ser Ala Gln Gly Ala Glu Lys Thr
65 70 75 80

Phe Lys Ala Gly Gly Arg Asp Asn Ser Leu Asn Thr Gly Lys Leu Lys
85 90 95

Asn Asp Lys Val Ser Arg Phe Asp Phe Val Gln Lys Ile Glu Val Asp
100 105 110

Gly Gln Thr Ile Thr Leu Ala Ser Gly Glu Phe Gln Ile Tyr Lys Gln
115 120 125

Asp His Ser Ala Val Val Ala Leu Gln Ile Glu Lys Ile Asn Asn Pro
130 135 140

Asp Lys Ile Asp Ser Leu Ile Asn Gln Arg Ser Phe Leu Val Ser Gly
145 150 155 160

Leu Gly Gly Glu His Thr Ala Phe Asn Gln Leu Pro Gly Gly Lys Ala
165 170 175

Glu Tyr His Gly Lys Ala Phe Ser Ser Asp Asp Pro Asn Gly Arg Leu
180 185 190

His Tyr Ser Ile Asp Phe Thr Lys Lys Gln Gly Tyr Gly Arg Ile Glu
195 200 205

His Leu Lys Thr Pro Glu Gln Asn Val Glu Leu Ala Ala Ala Glu Leu
210 215 220

Lys Ala Asp Glu Lys Ser His Ala Val Ile Leu Gly Asp Thr Arg Tyr
225 230 235 240

Gly Ser Glu Glu Lys Gly Thr Tyr His Leu Ala Leu Phe Gly Asp Arg
245 250 255

Ala Gln Glu Ile Ala Gly Ser Ala Thr Val Lys Ile Gly Glu Lys Val
260 265 270

His Glu Ile Gly Ile Ala Gly Lys Gln
275 280

<210> SEQ ID NO 57
<211> LENGTH: 160
<212> TYPE: PRT
<213> ORGANISM: Neisseria meningitidis

<400> SEQUENCE: 57

Phe Gln Val Tyr Lys Gln Ser His Ser Ala Leu Thr Ala Phe Gln Thr
1 5 10 15

Glu Gln Ile Gln Asp Ser Glu His Ser Gly Lys Met Val Ala Lys Arg
20 25 30

Gln Phe Arg Ile Gly Asp Ile Ala Gly Glu His Thr Ser Phe Asp Lys
35 40 45

Leu Pro Glu Gly Gly Arg Ala Thr Tyr Arg Gly Thr Ala Phe Gly Ser
50 55 60

Asp Asp Ala Gly Gly Lys Leu Thr Tyr Thr Ile Asp Phe Ala Ala Lys
65 70 75 80

Gln Gly Asn Gly Lys Ile Glu His Leu Lys Ser Pro Glu Leu Asn Val
85 90 95

Asp Leu Ala Ala Ala Asp Ile Lys Pro Asp Gly Lys Arg His Ala Val
100 105 110

Ile Ser Gly Ser Val Leu Tyr Asn Gln Ala Glu Lys Gly Ser Tyr Ser
115 120 125

Leu Gly Ile Phe Gly Gly Lys Ala Gln Glu Val Ala Gly Ser Ala Glu
130 135 140

```
Val Lys Thr Val Asn Gly Ile Arg His Ile Gly Leu Ala Ala Lys Gln
145                 150                 155                 160
```

<210> SEQ ID NO 58
<211> LENGTH: 159
<212> TYPE: PRT
<213> ORGANISM: Neisseria meningitidis

<400> SEQUENCE: 58

```
Phe Gln Val Tyr Lys Gln Ser His Ser Ala Leu Thr Ala Leu Gln Ile
1               5                   10                  15

Glu Lys Ile Asn Asn Pro Asp Lys Ile Asp Ser Met Val Ala Gln Arg
            20                  25                  30

Ser Phe Leu Val Ser Asp Ile Ala Gly Glu His Thr Ser Phe Asp Gln
        35                  40                  45

Leu Pro Asp Gly Lys Ala Thr Tyr Arg Gly Thr Ala Phe Gly Ser Asp
    50                  55                  60

Asp Ala Gly Gly Lys Leu His Tyr Thr Ile Asp Phe Ala Lys Lys Gln
65                  70                  75                  80

Gly His Gly Arg Ile Glu His Leu Lys Ser Pro Glu Leu Asn Val Asp
                85                  90                  95

Leu Ala Ala Ala Asp Ile Lys Ala Asp Glu Lys Ser His Ala Val Ile
            100                 105                 110

Ser Gly Ser Val Arg Tyr Gly Ser Glu Glu Lys Gly Ser Tyr Ser Leu
        115                 120                 125

Gly Ile Phe Gly Gly Lys Ala Gln Glu Val Ala Gly Ser Ala Glu Val
    130                 135                 140

Lys Ile Gly Glu Lys Val His Glu Ile Gly Leu Ala Ala Lys Gln
145                 150                 155
```

<210> SEQ ID NO 59
<211> LENGTH: 273
<212> TYPE: PRT
<213> ORGANISM: Neisseria meningitidis

<400> SEQUENCE: 59

```
Met Asn Arg Thr Ala Phe Cys Cys Leu Ser Leu Thr Thr Ala Leu Ile
1               5                   10                  15

Leu Thr Ala Cys Ser Ser Gly Gly Gly Gly Val Ala Ala Asp Ile Gly
            20                  25                  30

Ala Gly Leu Ala Asp Ala Leu Thr Ala Pro Leu Asp His Lys Asp Lys
        35                  40                  45

Gly Leu Gln Ser Leu Thr Leu Asp Gln Ser Val Arg Lys Asn Glu Lys
    50                  55                  60

Leu Lys Leu Ala Ala Gln Gly Ala Glu Lys Thr Tyr Gly Asn Gly Asp
65                  70                  75                  80

Ser Leu Asn Thr Gly Lys Leu Lys Asn Asp Lys Val Ser Arg Phe Asp
                85                  90                  95

Phe Ile Arg Gln Ile Glu Val Asp Gly Gln Leu Ile Thr Leu Glu Ser
            100                 105                 110

Gly Glu Phe Gln Val Tyr Lys Gln Ser His Ser Ala Leu Thr Ala Phe
        115                 120                 125

Gln Thr Glu Gln Ile Asn Asn Pro Asp Lys Ile Asp Ser Met Val Ala
    130                 135                 140

Lys Arg Gln Phe Arg Ile Gly Asp Ile Ala Gly Glu His Thr Ser Phe
145                 150                 155                 160
```

-continued

Asp Gln Leu Pro Asp Gly Lys Ala Thr Tyr Arg Gly Thr Ala Phe Gly
165 170 175

Ser Asp Asp Pro Asn Gly Lys Leu Thr Tyr Thr Ile Asp Phe Ala Ala
180 185 190

Lys Gln Gly His Gly Lys Ile Glu His Leu Lys Ser Pro Glu Leu Asn
195 200 205

Val Asp Leu Ala Ala Ala Asp Ile Lys Ala Asp Glu Lys Ser His Ala
210 215 220

Val Ile Ser Gly Ser Val Leu Tyr Gly Ser Glu Glu Lys Gly Ser Tyr
225 230 235 240

Ser Leu Gly Ile Phe Gly Gly Lys Ala Gln Glu Val Ala Gly Ser Ala
245 250 255

Glu Val Lys Ile Gly Glu Lys Val His Glu Ile Gly Leu Ala Ala Lys
260 265 270

Gln

<210> SEQ ID NO 60
<211> LENGTH: 159
<212> TYPE: PRT
<213> ORGANISM: Neisseria meningitidis

<400> SEQUENCE: 60

Phe Gln Val Tyr Lys Gln Ser His Ser Ala Leu Thr Ala Phe Gln Thr
1 5 10 15

Glu Gln Ile Asn Asn Pro Asp Lys Ile Asp Ser Met Val Ala Lys Arg
20 25 30

Gln Phe Arg Ile Gly Asp Ile Ala Gly Glu His Thr Ser Phe Asp Gln
35 40 45

Leu Pro Asp Gly Lys Ala Thr Tyr Arg Gly Thr Ala Phe Gly Ser Asp
50 55 60

Asp Ala Gly Gly Lys Leu Thr Tyr Thr Ile Asp Phe Ala Ala Lys Gln
65 70 75 80

Gly Asn Gly Arg Ile Glu His Leu Lys Ser Pro Glu Leu Asn Val Glu
85 90 95

Leu Ala Ala Ala Asp Ile Lys Pro Asp Gly Lys Arg His Ala Val Ile
100 105 110

Ser Gly Asp Thr Arg Tyr Gly Gly Glu Glu Lys Gly Ser Tyr Ser Leu
115 120 125

Gly Ile Phe Gly Gly Lys Ala Gln Glu Val Ala Gly Ser Ala Glu Val
130 135 140

Lys Ile Arg Asn Gly Ile Arg His Ile Gly Leu Ala Ala Lys Gln
145 150 155

<210> SEQ ID NO 61
<211> LENGTH: 7
<212> TYPE: PRT
<213> ORGANISM: Neisseria meningitidis

<400> SEQUENCE: 61

Lys Leu Pro Glu Gly Gly Arg
1 5

<210> SEQ ID NO 62
<211> LENGTH: 6
<212> TYPE: PRT
<213> ORGANISM: Neisseria meningitidis

<400> SEQUENCE: 62

Gln Leu Pro Asp Gly Lys
1 5

<210> SEQ ID NO 63
<211> LENGTH: 274
<212> TYPE: PRT
<213> ORGANISM: Neisseria meningitidis

<400> SEQUENCE: 63

Met Asn Arg Thr Ala Phe Cys Cys Leu Ser Leu Thr Thr Ala Leu Ile
1 5 10 15

Leu Thr Ala Cys Ser Ser Gly Gly Gly Gly Val Ala Ala Asp Ile Gly
20 25 30

Ala Gly Leu Ala Asp Ala Leu Thr Ala Pro Leu Asp His Lys Asp Lys
35 40 45

Gly Leu Gln Ser Leu Met Leu Asp Gln Ser Val Arg Lys Asn Glu Lys
50 55 60

Leu Lys Leu Ala Ala Gln Gly Ala Glu Lys Thr Tyr Gly Asn Gly Asp
65 70 75 80

Ser Leu Asn Thr Gly Lys Leu Lys Asn Asp Lys Val Ser Arg Phe Asp
85 90 95

Phe Ile Arg Gln Ile Glu Val Asp Gly Gln Leu Ile Thr Leu Glu Ser
100 105 110

Gly Glu Phe Gln Val Tyr Lys Gln Ser His Ser Ala Leu Thr Ala Leu
115 120 125

Gln Thr Glu Gln Val Gln Asp Ser Glu Asp Ser Gly Lys Met Val Ala
130 135 140

Lys Arg Gln Phe Arg Ile Gly Asp Ile Ala Gly Glu His Thr Ser Phe
145 150 155 160

Asp Lys Leu Pro Lys Asp Val Met Ala Thr Tyr Arg Gly Thr Ala Phe
165 170 175

Gly Ser Asp Asp Ala Gly Gly Lys Leu Thr Tyr Thr Ile Asp Phe Ala
180 185 190

Ala Lys Gln Gly His Gly Lys Ile Glu His Leu Lys Ser Pro Glu Leu
195 200 205

Asn Val Asp Leu Ala Ala Ala Tyr Ile Lys Pro Asp Glu Lys His His
210 215 220

Ala Val Ile Ser Gly Ser Val Leu Tyr Asn Gln Ala Glu Lys Gly Ser
225 230 235 240

Tyr Ser Leu Gly Ile Phe Gly Gly Lys Ala Gln Glu Val Ala Gly Ser
245 250 255

Ala Glu Val Lys Thr Val Asn Gly Ile Arg His Ile Gly Leu Ala Ala
260 265 270

Lys Gln

<210> SEQ ID NO 64
<211> LENGTH: 273
<212> TYPE: PRT
<213> ORGANISM: Neisseria meningitidis

<400> SEQUENCE: 64

Met Asn Arg Thr Ala Phe Cys Cys Leu Ser Leu Thr Ala Ala Leu Ile
1 5 10 15

Leu Thr Ala Cys Ser Ser Gly Gly Gly Gly Val Ala Ala Asp Ile Gly
20 25 30

Ala Gly Leu Ala Asp Ala Leu Thr Ala Pro Leu Asp His Lys Asp Lys
35 40 45

```
Ser Leu Gln Ser Leu Thr Leu Asp Gln Ser Val Arg Lys Asn Glu Lys
    50                  55                  60

Leu Lys Leu Ala Ala Gln Gly Ala Glu Lys Thr Tyr Gly Asn Gly Asp
65                  70                  75                  80

Ser Leu Asn Thr Gly Lys Leu Lys Asn Asp Lys Val Ser Arg Phe Asp
                85                  90                  95

Phe Ile Arg Gln Ile Glu Val Asp Gly Gln Leu Ile Thr Leu Glu Ser
            100                 105                 110

Gly Glu Phe Gln Ile Tyr Lys Gln Asp His Ser Ala Val Val Ala Leu
        115                 120                 125

Gln Ile Glu Lys Ile Asn Asn Pro Asp Lys Ile Asp Ser Leu Ile Asn
    130                 135                 140

Gln Arg Ser Phe Leu Val Ser Gly Leu Gly Gly Glu His Thr Ala Phe
145                 150                 155                 160

Asn Gln Leu Pro Gly Gly Lys Ala Glu Tyr His Gly Lys Ala Phe Ser
                165                 170                 175

Ser Asp Asp Ala Gly Gly Lys Leu Thr Tyr Thr Ile Asp Phe Ala Ala
            180                 185                 190

Lys Gln Gly His Gly Lys Ile Glu His Leu Lys Thr Pro Glu Gln Asn
        195                 200                 205

Val Glu Leu Ala Ala Ala Glu Leu Lys Ala Asp Glu Lys Ser His Ala
    210                 215                 220

Val Ile Leu Gly Asp Thr Arg Tyr Gly Ser Glu Glu Lys Gly Thr Tyr
225                 230                 235                 240

His Leu Ala Leu Phe Gly Asp Arg Ala Gln Glu Ile Ala Gly Ser Ala
                245                 250                 255

Thr Val Lys Ile Gly Glu Lys Val His Glu Ile Gly Ile Ala Gly Lys
            260                 265                 270

Gln


<210> SEQ ID NO 65
<211> LENGTH: 274
<212> TYPE: PRT
<213> ORGANISM: Neisseria meningitidis

<400> SEQUENCE: 65

Met Asn Arg Thr Ala Phe Cys Cys Leu Phe Leu Thr Thr Ala Leu Ile
1               5                   10                  15

Leu Thr Ala Cys Ser Ser Gly Gly Gly Gly Val Ala Ala Asp Ile Gly
            20                  25                  30

Val Gly Leu Ala Asp Ala Leu Thr Thr Pro Leu Asp His Lys Asp Lys
        35                  40                  45

Gly Leu Gln Ser Leu Thr Leu Asp Gln Ser Val Arg Lys Asn Glu Lys
    50                  55                  60

Leu Lys Leu Ala Ala Gln Gly Ala Glu Lys Thr Tyr Gly Asn Gly Asp
65                  70                  75                  80

Ser Leu Asn Thr Gly Lys Leu Lys Asn Asp Lys Val Ser Arg Phe Asp
                85                  90                  95

Phe Ile Arg Gln Ile Glu Val Asp Gly Gln Thr Ile Thr Leu Ala Ser
            100                 105                 110

Gly Glu Phe Gln Ile Tyr Lys Gln Asn His Ser Ala Val Val Ala Leu
        115                 120                 125

Gln Ile Glu Lys Ile Asn Asn Pro Asp Lys Ile Asp Ser Leu Ile Asn
    130                 135                 140
```

```
Gln Arg Ser Phe Leu Val Ser Gly Leu Gly Gly Glu His Thr Ala Phe
145                 150                 155                 160

Asn Gln Leu Pro Asp Gly Lys Ala Glu Tyr His Gly Lys Ala Phe Phe
                165                 170                 175

Ser Ser Asp Asp Pro Asn Gly Arg Leu His Tyr Ser Ile Asp Phe Thr
            180                 185                 190

Lys Lys Gln Gly Tyr Gly Arg Ile Glu His Leu Lys Thr Pro Glu Gln
        195                 200                 205

Asn Val Glu Leu Ala Ser Ala Glu Leu Lys Ala Asp Glu Lys Ser His
    210                 215                 220

Ala Val Ile Leu Gly Asp Thr Arg Tyr Gly Gly Glu Glu Lys Gly Thr
225                 230                 235                 240

Tyr His Leu Ala Leu Phe Gly Asp Arg Ala Gln Glu Ile Ala Gly Ser
                245                 250                 255

Ala Thr Val Lys Ile Gly Glu Lys Val His Glu Ile Gly Ile Ala Gly
            260                 265                 270

Lys Gln


<210> SEQ ID NO 66
<211> LENGTH: 12
<212> TYPE: PRT
<213> ORGANISM: Neisseria meningitidis

<400> SEQUENCE: 66

Gly Pro Asp Ser Asp Arg Leu Gln Gln Arg Arg Gly
1               5                   10


<210> SEQ ID NO 67
<211> LENGTH: 31
<212> TYPE: DNA
<213> ORGANISM: Neisseria meningitidis

<400> SEQUENCE: 67

cgcggatccc atatggtcgc cgccgacatc g                                    31


<210> SEQ ID NO 68
<211> LENGTH: 28
<212> TYPE: DNA
<213> ORGANISM: Neisseria meningitidis

<400> SEQUENCE: 68

cccgctcgag ctgtttgccg gcgatgcc                                        28


<210> SEQ ID NO 69
<211> LENGTH: 65
<212> TYPE: DNA
<213> ORGANISM: Neisseria meningitidis

<400> SEQUENCE: 69

cgcggatccc atatgggccc tgattctgac cgcctgcagc agcggagggt cgccgccgac     60

atcgg                                                                 65


<210> SEQ ID NO 70
<211> LENGTH: 28
<212> TYPE: DNA
<213> ORGANISM: Neisseria meningitidis

<400> SEQUENCE: 70

cccgctcgag ctgtttgccg gcgatgcc                                        28
```

<210> SEQ ID NO 71
<211> LENGTH: 31
<212> TYPE: DNA
<213> ORGANISM: Neisseria meningitidis

<400> SEQUENCE: 71
cgcggatccc atatggtcgc cgccgacatc g 31

<210> SEQ ID NO 72
<211> LENGTH: 28
<212> TYPE: DNA
<213> ORGANISM: Neisseria meningitidis

<400> SEQUENCE: 72
cccgctcgag ctgtttgccg gcgatgcc 28

<210> SEQ ID NO 73
<211> LENGTH: 65
<212> TYPE: DNA
<213> ORGANISM: Neisseria meningitidis

<400> SEQUENCE: 73
cgcggatccc atatgggccc tgattctgac cgcctgcagc agcggagggt cgccgccgac 60
atcgg 65

<210> SEQ ID NO 74
<211> LENGTH: 28
<212> TYPE: DNA
<213> ORGANISM: Neisseria meningitidis

<400> SEQUENCE: 74
cccgctcgag ctgtttgccg gcgatgcc 28

<210> SEQ ID NO 75
<211> LENGTH: 31
<212> TYPE: DNA
<213> ORGANISM: Neisseria meningitidis

<400> SEQUENCE: 75
cgcggatccc atatggtcgc cgccgacatc g 31

<210> SEQ ID NO 76
<211> LENGTH: 28
<212> TYPE: DNA
<213> ORGANISM: Neisseria meningitidis

<400> SEQUENCE: 76
cccgctcgag ctgtttgccg gcgatgcc 28

<210> SEQ ID NO 77
<211> LENGTH: 65
<212> TYPE: DNA
<213> ORGANISM: Neisseria meningitidis

<400> SEQUENCE: 77
cgcggatccc atatgggccc tgattctgac cgcctgcagc agcggagggt cgccgccgac 60
atcgg 65

<210> SEQ ID NO 78
<211> LENGTH: 28
<212> TYPE: DNA
<213> ORGANISM: Neisseria meningitidis

<400> SEQUENCE: 78
cccgctcgag ctgtttgccg gcgatgcc 28

<210> SEQ ID NO 79
<211> LENGTH: 31
<212> TYPE: DNA
<213> ORGANISM: Neisseria meningitidis

<400> SEQUENCE: 79
cgcggatccc atatggtcgc cgccgacatc g 31

<210> SEQ ID NO 80
<211> LENGTH: 28
<212> TYPE: DNA
<213> ORGANISM: Neisseria meningitidis

<400> SEQUENCE: 80
cccgctcgag ctgtttgccg gcgatgcc 28

<210> SEQ ID NO 81
<211> LENGTH: 65
<212> TYPE: DNA
<213> ORGANISM: Neisseria meningitidis

<400> SEQUENCE: 81
cgcggatccc atatgggccc tgattctgac cgcctgcagc agcggagggt cgccgccgac 60
atcgg 65

<210> SEQ ID NO 82
<211> LENGTH: 28
<212> TYPE: DNA
<213> ORGANISM: Neisseria meningitidis

<400> SEQUENCE: 82
cccgctcgag ctgtttgccg gcgatgcc 28

<210> SEQ ID NO 83
<211> LENGTH: 31
<212> TYPE: DNA
<213> ORGANISM: Neisseria meningitidis

<400> SEQUENCE: 83
cgcggatccc atatggtcgc cgccgacatc g 31

<210> SEQ ID NO 84
<211> LENGTH: 28
<212> TYPE: DNA
<213> ORGANISM: Neisseria meningitidis

<400> SEQUENCE: 84
cccgctcgag ctgtttgccg gcgatgcc 28

<210> SEQ ID NO 85
<211> LENGTH: 65
<212> TYPE: DNA
<213> ORGANISM: Neisseria meningitidis

<400> SEQUENCE: 85
cgcggatccc atatgggccc tgattctgac cgcctgcagc agcggagggt cgccgccgac 60
atcgg 65

<210> SEQ ID NO 86
<211> LENGTH: 273

<212> TYPE: PRT
<213> ORGANISM: Neisseria meningitidis

<400> SEQUENCE: 86

Met Asn Arg Thr Ala Phe Cys Cys Leu Ser Leu Thr Ala Ala Leu Ile
1               5                   10                  15

Leu Thr Ala Cys Ser Ser Gly Gly Gly Gly Val Ala Ala Asp Ile Gly
            20                  25                  30

Ala Gly Leu Ala Asp Ala Leu Thr Ala Pro Leu Asp His Lys Asp Lys
        35                  40                  45

Ser Leu Gln Ser Leu Thr Leu Asp Gln Ser Val Arg Lys Asn Glu Lys
    50                  55                  60

Leu Lys Leu Ala Ala Gln Gly Ala Glu Lys Thr Tyr Gly Asn Gly Asp
65                  70                  75                  80

Ser Leu Asn Thr Gly Lys Leu Lys Asn Asp Lys Val Ser Arg Phe Asp
                85                  90                  95

Phe Ile Arg Gln Ile Glu Val Asp Gly Gln Leu Ile Thr Leu Glu Ser
            100                 105                 110

Gly Glu Phe Gln Ile Tyr Lys Gln Asp His Ser Ala Val Val Ala Leu
        115                 120                 125

Gln Ile Glu Lys Ile Asn Asn Pro Asp Lys Ile Asp Ser Leu Ile Asn
    130                 135                 140

Gln Arg Ser Phe Leu Val Ser Gly Leu Gly Gly Glu His Thr Ala Phe
145                 150                 155                 160

Asn Gln Leu Pro Ser Gly Lys Ala Glu Tyr His Gly Lys Ala Phe Ser
                165                 170                 175

Ser Asp Asp Ala Gly Gly Lys Leu Thr Tyr Thr Ile Asp Phe Ala Ala
            180                 185                 190

Lys Gln Gly His Gly Lys Ile Glu His Leu Lys Thr Pro Glu Gln Asn
        195                 200                 205

Val Glu Leu Ala Ser Ala Glu Leu Lys Ala Asp Glu Lys Ser His Ala
    210                 215                 220

Val Ile Leu Gly Asp Thr Arg Tyr Gly Gly Glu Glu Lys Gly Thr Tyr
225                 230                 235                 240

His Leu Ala Leu Phe Gly Asp Arg Ala Gln Glu Ile Ala Gly Ser Ala
                245                 250                 255

Thr Val Lys Ile Arg Glu Lys Val His Glu Ile Gly Ile Ala Gly Lys
            260                 265                 270

Gln

<210> SEQ ID NO 87
<211> LENGTH: 272
<212> TYPE: PRT
<213> ORGANISM: Neisseria meningitidis

<400> SEQUENCE: 87

Met Asn Arg Thr Ala Phe Cys Cys Leu Ser Leu Thr Thr Ala Leu Ile
1               5                   10                  15

Leu Thr Ala Cys Ser Ser Gly Gly Gly Gly Val Ala Ala Asp Ile Gly
            20                  25                  30

Thr Gly Leu Ala Asp Ala Leu Thr Ala Pro Leu Asp His Lys Asp Lys
        35                  40                  45

Gly Leu Gln Ser Leu Thr Leu Asp Gln Ser Val Arg Lys Asn Glu Lys
    50                  55                  60

Leu Lys Leu Ala Ala Gln Gly Ala Glu Lys Thr Tyr Gly Asn Gly Asp
65                  70                  75                  80

```
Ser Leu Asn Thr Gly Lys Leu Lys Asn Asp Lys Val Ser Arg Phe Asp
                85                  90                  95

Phe Ile Arg Gln Ile Glu Val Asp Gly Leu Ile Thr Leu Glu Ser Gly
            100                 105                 110

Glu Phe Gln Ile Tyr Lys Gln Asp His Ser Ala Val Val Ala Leu Gln
        115                 120                 125

Ile Glu Lys Ile Asn Asn Pro Asp Lys Ile Asp Ser Leu Ile Asn Gln
    130                 135                 140

Arg Ser Phe Leu Val Ser Gly Leu Gly Gly Glu His Thr Ala Phe Asn
145                 150                 155                 160

Gln Leu Pro Ser Gly Lys Ala Glu Tyr His Gly Lys Ala Phe Ser Ser
                165                 170                 175

Asp Asp Ala Gly Gly Lys Leu Thr Tyr Thr Ile Asp Phe Ala Ala Lys
            180                 185                 190

Gln Gly His Gly Lys Ile Glu His Leu Lys Thr Pro Glu Gln Asn Val
        195                 200                 205

Glu Leu Ala Ser Ala Glu Leu Lys Ala Asp Glu Lys Ser His Ala Val
    210                 215                 220

Ile Leu Gly Asp Thr Arg Tyr Gly Gly Glu Glu Lys Gly Thr Tyr His
225                 230                 235                 240

Leu Ala Leu Phe Gly Asp Arg Ala Gln Glu Ile Ala Gly Ser Ala Thr
                245                 250                 255

Val Lys Ile Arg Glu Lys Val His Glu Ile Gly Ile Ala Gly Lys Gln
            260                 265                 270


<210> SEQ ID NO 88
<211> LENGTH: 272
<212> TYPE: PRT
<213> ORGANISM: Neisseria meningitidis

<400> SEQUENCE: 88

Met Asn Arg Thr Ala Phe Cys Cys Leu Ser Leu Thr Ala Ala Leu Ile
1               5                   10                  15

Leu Thr Ala Cys Ser Ser Gly Gly Gly Gly Val Ala Ala Asp Ile Gly
            20                  25                  30

Ala Gly Leu Ala Asp Ala Leu Thr Ala Pro Leu Asp His Lys Asp Lys
        35                  40                  45

Ser Leu Gln Ser Leu Thr Leu Asp Gln Ser Val Arg Lys Asn Glu Lys
    50                  55                  60

Leu Lys Leu Ala Ala Gln Gly Ala Glu Lys Thr Tyr Gly Asn Gly Asp
65                  70                  75                  80

Ser Leu Asn Thr Gly Lys Leu Lys Asn Asp Lys Val Ser Arg Phe Asp
                85                  90                  95

Phe Ile Arg Gln Ile Glu Val Asp Gly Gln Thr Ile Thr Leu Ala Ser
            100                 105                 110

Gly Glu Phe Gln Ile Tyr Lys Gln Asn His Ser Ala Val Val Ala Leu
        115                 120                 125

Gln Ile Glu Lys Ile Asn Asn Pro Asp Lys Ile Asp Ser Leu Ile Asn
    130                 135                 140

Gln Arg Ser Phe Leu Val Ser Gly Leu Gly Gly Glu His Thr Ala Phe
145                 150                 155                 160

Asn Gln Leu Pro Asp Gly Lys Ala Glu Tyr His Gly Ala Phe Ser Ser
                165                 170                 175

Asp Asp Pro Asn Gly Arg Leu His Tyr Ser Ile Asp Phe Thr Lys Lys
            180                 185                 190
```

-continued

```
Gln Gly Tyr Gly Arg Ile Glu His Leu Lys Thr Pro Glu Gln Asn Val
        195                 200                 205

Glu Leu Ala Ser Ala Glu Leu Lys Ala Asp Glu Lys Ser His Ala Val
    210                 215                 220

Ile Leu Gly Asp Thr Arg Tyr Gly Gly Glu Glu Lys Gly Thr Tyr His
225                 230                 235                 240

Leu Ala Leu Phe Gly Asp Arg Ala Gln Glu Ile Ala Gly Ser Ala Thr
                245                 250                 255

Val Lys Ile Arg Glu Lys Val His Glu Ile Gly Ile Ala Gly Lys Gln
            260                 265                 270
```

<210> SEQ ID NO 89
<211> LENGTH: 281
<212> TYPE: PRT
<213> ORGANISM: Neisseria meningitidis

<400> SEQUENCE: 89

```
Met Asn Arg Thr Ala Phe Cys Cys Leu Phe Leu Thr Thr Ala Leu Ile
1               5                   10                  15

Leu Thr Ala Cys Ser Ser Gly Gly Gly Gly Ser Gly Ser Gly Gly Val
            20                  25                  30

Ala Ala Asp Ile Gly Thr Gly Leu Ala Asp Ala Leu Thr Thr Pro Leu
        35                  40                  45

Asp His Lys Asp Lys Gly Leu Lys Ser Leu Thr Leu Glu Asp Ser Ile
    50                  55                  60

Pro Gln Asn Gly Thr Leu Thr Leu Ser Ala Gln Gly Ala Glu Lys Thr
65                  70                  75                  80

Phe Lys Ala Gly Asp Lys Asp Asn Ser Leu Asn Thr Gly Lys Leu Lys
                85                  90                  95

Asn Asp Lys Ile Ser Arg Phe Asp Phe Val Gln Lys Ile Glu Val Asp
            100                 105                 110

Gly Gln Thr Ile Thr Leu Ala Ser Gly Glu Phe Gln Ile Tyr Lys Gln
        115                 120                 125

Asp His Ser Ala Val Val Ala Leu Gln Ile Glu Lys Ile Asn Asn Pro
    130                 135                 140

Asp Lys Ile Asp Ser Leu Ile Asn Gln Arg Ser Phe Leu Val Ser Gly
145                 150                 155                 160

Leu Gly Gly Glu His Thr Ala Phe Asn Gln Leu Pro Gly Gly Lys Ala
                165                 170                 175

Glu Tyr His Gly Lys Ala Phe Ser Ser Asp Asp Ala Gly Gly Lys Leu
            180                 185                 190

Thr Tyr Thr Ile Asp Phe Ala Ala Lys Gln Gly His Gly Lys Thr Glu
        195                 200                 205

His Leu Lys Thr Pro Glu Gln Asn Val Glu Leu Ala Ala Ala Glu Leu
    210                 215                 220

Lys Ala Asp Glu Lys Ser His Ala Val Ile Leu Gly Asp Thr Arg Tyr
225                 230                 235                 240

Gly Ser Glu Glu Lys Gly Thr Tyr His Leu Ala Leu Phe Gly Asp Arg
                245                 250                 255

Ala Gln Glu Ile Ala Gly Ser Ala Thr Val Lys Ile Gly Glu Lys Val
            260                 265                 270

His Glu Ile Gly Ile Ala Gly Lys Gln
        275                 280
```

<210> SEQ ID NO 90

<211> LENGTH: 273
<212> TYPE: PRT
<213> ORGANISM: Neisseria meningitidis

<400> SEQUENCE: 90

```
Met Asn Arg Thr Ala Phe Cys Cys Phe Ser Leu Thr Ala Ala Leu Ile
1               5                   10                  15

Leu Thr Ala Cys Ser Ser Gly Gly Gly Gly Val Ala Ala Asp Ile Gly
            20                  25                  30

Ala Gly Leu Ala Asp Ala Leu Thr Ala Pro Leu Asp His Lys Asp Lys
        35                  40                  45

Gly Leu Gln Ser Leu Thr Leu Asp Gln Ser Val Arg Lys Asn Glu Lys
    50                  55                  60

Leu Lys Leu Ala Ala Gln Gly Ala Glu Lys Thr Tyr Gly Asn Gly Asp
65                  70                  75                  80

Ser Leu Asn Thr Gly Lys Leu Lys Asn Asp Lys Val Ser Arg Phe Asp
                85                  90                  95

Phe Ile Arg Gln Ile Glu Val Asp Gly Lys Leu Ile Thr Leu Glu Ser
            100                 105                 110

Gly Glu Phe Gln Val Tyr Lys Gln Ser His Ser Ala Leu Thr Ala Leu
        115                 120                 125

Gln Thr Glu Gln Val Gln Asp Ser Glu Asp Ser Gly Met Val Ala Lys
    130                 135                 140

Arg Gln Phe Arg Ile Gly Asp Ile Ala Gly Glu His Thr Ser Phe Asp
145                 150                 155                 160

Lys Leu Pro Lys Gly Gly Ser Ala Thr Tyr Arg Gly Thr Ala Phe Gly
                165                 170                 175

Ser Asp Asp Ala Gly Gly Lys Leu Thr Tyr Thr Ile Asp Phe Ala Ala
            180                 185                 190

Lys Gln Gly His Gly Lys Ile Glu His Leu Lys Ser Pro Glu Leu Asn
        195                 200                 205

Val Glu Leu Ala Thr Ala Tyr Ile Lys Pro Asp Glu Lys Arg His Ala
    210                 215                 220

Val Ile Ser Gly Ser Val Leu Tyr Asn Gln Asp Glu Lys Gly Ser Tyr
225                 230                 235                 240

Ser Leu Gly Ile Phe Gly Gly Gln Ala Gln Glu Val Ala Gly Ser Ala
                245                 250                 255

Glu Val Glu Thr Ala Asn Gly Ile His His Ile Gly Leu Ala Ala Lys
            260                 265                 270

Gln
```

<210> SEQ ID NO 91
<211> LENGTH: 274
<212> TYPE: PRT
<213> ORGANISM: Neisseria meningitidis

<400> SEQUENCE: 91

```
Met Asn Arg Thr Ala Phe Cys Cys Leu Ser Leu Thr Ala Ala Leu Ile
1               5                   10                  15

Leu Thr Ala Cys Ser Ser Gly Gly Gly Gly Val Ala Ala Asp Ile Gly
            20                  25                  30

Ala Gly Leu Ala Asp Ala Leu Thr Ala Pro Leu Asp His Lys Asp Lys
        35                  40                  45

Gly Leu Gln Ser Leu Thr Leu Asp Gln Ser Val Arg Lys Asn Glu Lys
    50                  55                  60

Leu Lys Leu Ala Ala Gln Gly Ala Glu Lys Thr Tyr Gly Asn Gly Asp
```

```
65                  70                  75                  80

Ser Leu Asn Thr Gly Lys Leu Lys Asn Asp Lys Val Ser Arg Phe Asp
                85                  90                  95

Phe Ile Arg Gln Ile Glu Val Asp Gly Gln Leu Ile Thr Leu Glu Ser
            100                 105                 110

Gly Glu Phe Gln Val Tyr Lys Gln Ser His Ser Ala Leu Thr Ala Leu
        115                 120                 125

Gln Thr Glu Gln Val Gln Asp Ser Glu Asp Ser Gly Lys Met Val Ala
    130                 135                 140

Lys Arg Gln Phe Arg Ile Gly Asp Ile Ala Gly Glu His Thr Ser Phe
145                 150                 155                 160

Asp Lys Leu Pro Lys Gly Gly Ser Ala Thr Tyr Arg Gly Thr Ala Phe
                165                 170                 175

Ser Ser Asp Asp Ala Gly Gly Lys Leu Thr Tyr Thr Ile Asp Phe Ala
            180                 185                 190

Ala Lys Gln Gly His Gly Lys Ile Glu His Leu Lys Ser Pro Glu Leu
        195                 200                 205

Asn Val Glu Leu Ala Thr Ala Tyr Ile Lys Pro Asp Glu Lys Arg His
    210                 215                 220

Ala Val Ile Ser Gly Ser Val Leu Tyr Asn Gln Asp Glu Lys Gly Ser
225                 230                 235                 240

Tyr Ser Leu Gly Ile Phe Gly Gly Gln Ala Gln Glu Val Ala Gly Ser
                245                 250                 255

Ala Glu Val Glu Thr Ala Asn Gly Ile Gln His Ile Gly Leu Ala Ala
            260                 265                 270

Lys Gln


<210> SEQ ID NO 92
<211> LENGTH: 274
<212> TYPE: PRT
<213> ORGANISM: Neisseria meningitidis

<400> SEQUENCE: 92

Met Asn Arg Thr Ala Phe Cys Cys Leu Ser Leu Thr Thr Ala Leu Ile
1               5                   10                  15

Leu Thr Ala Cys Ser Ser Gly Gly Gly Gly Val Ala Ala Asp Ile Gly
            20                  25                  30

Ala Gly Leu Ala Asp Ala Leu Thr Ala Pro Leu Asp His Lys Asp Lys
        35                  40                  45

Gly Leu Gln Ser Leu Met Leu Asp Gln Ser Val Arg Lys Asn Glu Lys
    50                  55                  60

Leu Lys Leu Ala Ala Gln Gly Ala Glu Lys Thr Tyr Gly Asn Gly Asp
65                  70                  75                  80

Ser Leu Asn Thr Gly Lys Leu Lys Asn Asp Lys Val Ser Arg Phe Asp
                85                  90                  95

Phe Ile Arg Gln Ile Glu Val Asp Gly Gln Leu Ile Thr Leu Glu Ser
            100                 105                 110

Gly Glu Phe Gln Val Tyr Lys Gln Ser His Ser Ala Leu Thr Ala Leu
        115                 120                 125

Gln Thr Glu Gln Val Gln Asp Ser Glu His Ser Gly Lys Met Val Ala
    130                 135                 140

Lys Arg Gln Phe Arg Ile Gly Asp Ile Ala Gly Glu His Thr Ser Phe
145                 150                 155                 160

Asp Lys Leu Pro Glu Gly Gly Arg Ala Thr Tyr Arg Gly Thr Ala Phe
                165                 170                 175
```

-continued

```
Gly Ser Asp Asp Ala Gly Gly Lys Leu Ile Tyr Thr Ile Asp Phe Ala
            180                 185                 190

Ala Lys Gln Gly His Gly Lys Ile Glu His Leu Lys Ser Pro Glu Leu
        195                 200                 205

Asn Val Asp Leu Ala Ala Ala Tyr Ile Lys Pro Asp Glu Lys His His
    210                 215                 220

Ala Val Ile Ser Gly Ser Val Leu Tyr Asn Gln Ala Glu Lys Gly Ser
225                 230                 235                 240

Tyr Ser Leu Gly Ile Phe Gly Gly Lys Ala Gln Glu Val Ala Gly Ser
                245                 250                 255

Ala Glu Val Lys Thr Val Asn Gly Ile Arg His Ile Gly Leu Ala Ala
            260                 265                 270

Lys Gln


<210> SEQ ID NO 93
<211> LENGTH: 274
<212> TYPE: PRT
<213> ORGANISM: Neisseria meningitidis

<400> SEQUENCE: 93

Met Asn Arg Thr Ala Phe Cys Cys Leu Ser Leu Thr Ala Ala Leu Ile
1               5                   10                  15

Leu Thr Ala Cys Ser Ser Gly Gly Gly Gly Val Ala Ala Asp Ile Gly
            20                  25                  30

Ala Gly Leu Ala Asp Ala Leu Thr Ala Pro Leu Asp His Lys Asp Lys
        35                  40                  45

Ser Leu Gln Ser Leu Thr Leu Asp Gln Ser Val Arg Lys Asn Glu Lys
    50                  55                  60

Leu Lys Leu Ala Ala Gln Gly Ala Glu Lys Thr Tyr Gly Asn Gly Asp
65                  70                  75                  80

Ser Leu Asn Thr Gly Lys Leu Lys Asn Asp Lys Val Ser Arg Phe Asp
                85                  90                  95

Phe Ile Arg Gln Ile Glu Val Asp Gly Gln Leu Ile Thr Leu Glu Ser
            100                 105                 110

Gly Glu Phe Gln Val Tyr Lys Gln Ser His Ser Ala Leu Thr Ala Leu
        115                 120                 125

Gln Thr Glu Gln Val Gln Asp Ser Glu His Ser Gly Lys Met Val Ala
    130                 135                 140

Lys Arg Gln Phe Arg Ile Gly Asp Ile Ala Gly Glu His Thr Ser Phe
145                 150                 155                 160

Asp Lys Leu Pro Glu Gly Gly Arg Ala Thr Tyr Arg Gly Thr Ala Phe
                165                 170                 175

Gly Ser Asp Asp Ala Ser Gly Lys Leu Thr Tyr Thr Ile Asp Phe Ala
            180                 185                 190

Ala Lys Gln Gly His Gly Lys Ile Glu His Leu Lys Ser Pro Glu Leu
        195                 200                 205

Asn Val Asp Leu Ala Ala Ser Asp Ile Lys Pro Asp Lys Lys Arg His
    210                 215                 220

Ala Val Ile Ser Gly Ser Val Leu Tyr Asn Gln Ala Glu Lys Gly Ser
225                 230                 235                 240

Tyr Ser Leu Gly Ile Phe Gly Gly Gln Ala Gln Glu Val Ala Gly Ser
                245                 250                 255

Ala Glu Val Glu Thr Ala Asn Gly Ile Arg His Ile Gly Leu Ala Ala
            260                 265                 270
```

```
Lys Gln


<210> SEQ ID NO 94
<211> LENGTH: 280
<212> TYPE: PRT
<213> ORGANISM: Neisseria meningitidis

<400> SEQUENCE: 94

Met Asn Arg Thr Thr Phe Cys Cys Leu Ser Leu Thr Ala Ala Leu Ile
1               5                   10                  15

Leu Thr Ala Cys Ser Ser Gly Gly Gly Gly Ser Gly Gly Gly Gly Val
            20                  25                  30

Ala Ala Asp Ile Gly Ala Gly Leu Ala Asp Thr Ala Pro Leu Asp His
        35                  40                  45

Lys Asp Lys Gly Leu Lys Ser Leu Thr Leu Glu Asp Ser Ile Ser Gln
    50                  55                  60

Asn Gly Thr Leu Thr Leu Ser Ala Gln Gly Ala Glu Arg Thr Phe Lys
65                  70                  75                  80

Ala Gly Asp Lys Asp Asn Ser Leu Asn Thr Gly Lys Leu Lys Asn Asp
                85                  90                  95

Lys Ile Ser Arg Phe Asp Phe Ile Arg Gln Ile Glu Val Asp Gly Gln
            100                 105                 110

Leu Ile Thr Leu Glu Ser Gly Glu Phe Gln Val Tyr Lys Gln Ser His
        115                 120                 125

Ser Ala Leu Thr Ala Leu Gln Thr Glu Gln Val Gln Asp Ser Glu His
    130                 135                 140

Ser Gly Lys Met Val Ala Lys Arg Gln Phe Arg Ile Gly Asp Ile Val
145                 150                 155                 160

Gly Glu His Thr Ser Phe Gly Lys Leu Pro Lys Asp Val Met Ala Thr
                165                 170                 175

Tyr Arg Gly Thr Ala Phe Gly Ser Asp Asp Ala Gly Gly Lys Leu Thr
            180                 185                 190

Tyr Thr Ile Asp Phe Ala Ala Lys Gln Gly His Gly Lys Ile Glu His
        195                 200                 205

Leu Lys Ser Pro Glu Leu Asn Val Asp Leu Ala Ala Ala Asp Ile Lys
    210                 215                 220

Pro Asp Glu Lys His His Ala Val Ile Ser Gly Ser Val Leu Tyr Asn
225                 230                 235                 240

Gln Ala Glu Lys Gly Ser Tyr Ser Leu Gly Ile Phe Gly Gly Gln Ala
                245                 250                 255

Gln Glu Val Ala Gly Ser Ala Glu Val Glu Thr Ala Asn Gly Ile Arg
            260                 265                 270

His Ile Gly Leu Ala Ala Lys Gln
        275                 280


<210> SEQ ID NO 95
<211> LENGTH: 251
<212> TYPE: PRT
<213> ORGANISM: Neisseria meningitidis

<400> SEQUENCE: 95

Val Ala Ala Asp Ile Gly Ala Gly Leu Ala Asp Ala Leu Thr Ala Pro
1               5                   10                  15

Leu Asp His Lys Asp Lys Gly Leu Lys Ser Leu Thr Leu Glu Asp Ser
            20                  25                  30

Ile Ser Gln Asn Gly Thr Leu Thr Leu Ser Ala Gln Gly Ala Glu Arg
        35                  40                  45
```

-continued

```
Thr Phe Lys Ala Gly Asp Lys Asp Asn Ser Leu Asn Thr Gly Lys Leu
    50                  55                  60

Lys Asn Asp Lys Ile Ser Arg Phe Asp Phe Ile Arg Gln Ile Glu Val
65                  70                  75                  80

Asp Gly Gln Leu Ile Thr Leu Glu Ser Gly Glu Phe Gln Val Tyr Lys
                85                  90                  95

Gln Ser His Ser Ala Leu Thr Ala Leu Gln Thr Glu Gln Val Gln Asp
            100                 105                 110

Ser Glu His Ser Gly Lys Met Val Ala Lys Arg Gln Phe Arg Ile Gly
        115                 120                 125

Asp Ile Val Gly Glu His Thr Ser Phe Gly Lys Leu Pro Lys Asp Val
    130                 135                 140

Met Ala Thr Tyr Arg Gly Thr Ala Phe Gly Ser Asp Asp Ala Gly Gly
145                 150                 155                 160

Lys Leu Thr Tyr Thr Ile Asp Phe Ala Ala Lys Gln Gly His Gly Lys
                165                 170                 175

Ile Glu His Leu Lys Ser Pro Glu Leu Asn Val Asp Leu Ala Ala Ala
            180                 185                 190

Asp Ile Lys Pro Asp Glu Lys His His Ala Val Ile Ser Gly Ser Val
        195                 200                 205

Leu Tyr Asn Gln Ala Glu Lys Gly Ser Tyr Ser Leu Gly Ile Phe Gly
    210                 215                 220

Gly Gln Ala Gln Glu Val Ala Gly Ser Ala Glu Val Glu Thr Ala Asn
225                 230                 235                 240

Gly Ile Arg His Ile Gly Leu Ala Ala Lys Gln
                245                 250
```